(12) United States Patent
Anazawa et al.

(10) Patent No.: US 9,921,160 B2
(45) Date of Patent: Mar. 20, 2018

(54) MULTICHANNEL ANALYSIS DEVICE

(71) Applicant: HITACHI HIGH-TECHNOLOGIES CORPORATION, Minato-ku, Tokyo (JP)

(72) Inventors: Takashi Anazawa, Tokyo (JP); Yoshitaka Kodama, Tokyo (JP); Motohiro Yamazaki, Tokyo (JP); Kunio Harada, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 15/324,149

(22) PCT Filed: Jun. 23, 2015

(86) PCT No.: PCT/JP2015/068048
§ 371 (c)(1),
(2) Date: Jan. 5, 2017

(87) PCT Pub. No.: WO2016/009796
PCT Pub. Date: Jan. 21, 2016

(65) Prior Publication Data
US 2017/0212052 A1    Jul. 27, 2017

(30) Foreign Application Priority Data

Jul. 14, 2014    (JP) .................. PCT/JP2014/068657

(51) Int. Cl.
*G01N 21/64*    (2006.01)
*G01N 21/01*    (2006.01)
(52) U.S. Cl.
CPC ......... *G01N 21/6454* (2013.01); *G01N 21/01* (2013.01); *G01N 2201/06113* (2013.01)

(58) Field of Classification Search
CPC ............... G01N 33/583; G01N 29/022; G01N 27/44719
See application file for complete search history.

(56) References Cited

U.S. PATENT DOCUMENTS 5,938,904 A    8/1999   Bader et al.
6,192,168 B1*  2/2001   Feldstein ............ G01N 21/552
                                                        385/12

(Continued)

FOREIGN PATENT DOCUMENTS

JP    2000-507695 A    6/2000
JP    2002-022654 A    1/2002

(Continued)

OTHER PUBLICATIONS

Tsupryk A., et al.; Novel Design of Multicapillary Arrays for High-Throughout DNA Sequencing, Electrophoresis Jul. 2006; vol. 27; No. 14; pp. 2869-2879.

(Continued)

*Primary Examiner* — Kiho Kim
(74) *Attorney, Agent, or Firm* — Miles & Stockbridge P.C.

(57) ABSTRACT

A laser beam 6 irradiated from a side face of a microchip 1 in which plural channels 2 fill ed with a member of a refractive index $n_2$ in an inner portion of a member of a refractive index $n_1$ ($n_2 < n_1$) are arranged in parallel with the same plane, along the same plane is refracted in a direction of being directed from an upper base to a lower base in a case where a section of the channel 2 is configured by a trapezoidal shape of upper base>lower base, and is deviated swiftly from a channel array. Hence, the laser beam 6 is made to be deviated gradually from the channel array by irradiating the laser beam 6 from the side face of the microchip 1 by being inclined relative to the same plane in a direction of being directed from the lower base to the upper (Continued)

base. As a result, a larger number of the channels 2 can efficiently be subjected to laser beam irradiation.

26 Claims, 48 Drawing Sheets

(56) References Cited

U.S. PATENT DOCUMENTS

| | | | |
|---|---|---|---|
| 7,189,361 B2* | 3/2007 | Carson | G01N 21/0303 356/300 |
| 2002/0005953 A1 | 1/2002 | Negami et al. | |
| 2003/0040010 A1 | 2/2003 | Grossman et al. | |
| 2003/0113935 A1 | 6/2003 | Carson et al. | |
| 2005/0140971 A1 | 6/2005 | Yamaguchi et al. | |
| 2011/0036992 A1 | 2/2011 | Fukumoto et al. | |
| 2011/0305898 A1* | 12/2011 | Zhang | A61L 27/34 428/336 |
| 2012/0138461 A1 | 6/2012 | Sugiyama et al. | |
| 2012/0163403 A1* | 6/2012 | Essaian | H01S 3/109 372/10 |
| 2012/0307244 A1* | 12/2012 | Sharpe | G01N 15/1012 356/338 |

FOREIGN PATENT DOCUMENTS

| | | |
|---|---|---|
| JP | 2003-279471 A | 10/2003 |
| JP | 2005-501249 A | 1/2005 |
| JP | 2005-091168 A | 4/2005 |
| JP | 2005-514591 A | 5/2005 |
| JP | 2011-59095 A | 3/2011 |
| JP | 2012-132894 A | 7/2012 |
| JP | 2013-108994 A | 6/2013 |

OTHER PUBLICATIONS

Emory J. M., et al.; "Charge-Coupled Device Operated in a Time-Delayed Integration Mode as an Approach to High-Throughput Flow-Based Single Molecule Anaylysis"; May 15, 2008; vol. 80; No. 10; pp. 3897-3903.

* cited by examiner

ELECTROPHORESIS

WAVELENGTH
DISPERSION DIRECTION

CHANNEL ARRAY DIRECTION

ELECTROPHORESIS 20

WAVELENGTH DISPERSION DIRECTION

CHANNEL ARRAY DIRECTION

R=37mm

R=46mm

R=55mm

R=68mm

R=110mm

CHANNEL NUMBER

FIG. 34
| | SURFACE OBSERVATION IMAGE BY LASER MICROSCOPE | SURFACE ROUGHNESS RMS |
|---|---|---|
| SIDE FACE | 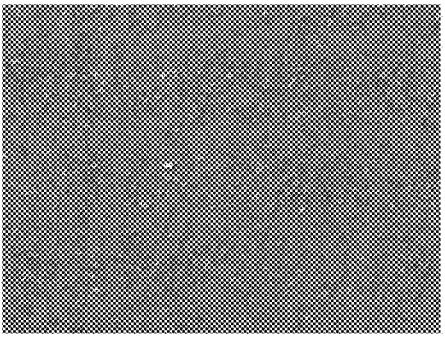 | 0.44 μm |
| FRONT FACE | 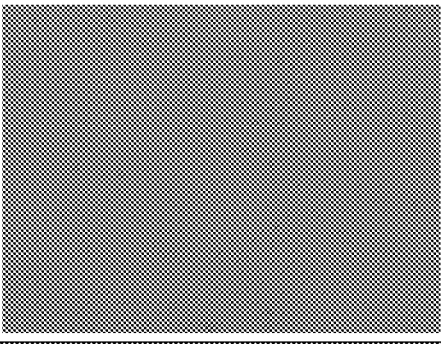 | 0.07 μm |

FIG. 35
| STATE OF SIDE FACE | SURFACE OBSERVATION IMAGE BY LASER MICROSCOPE | SURFACE ROUGHNESS RMS |
|---|---|---|
| UNTREATED | 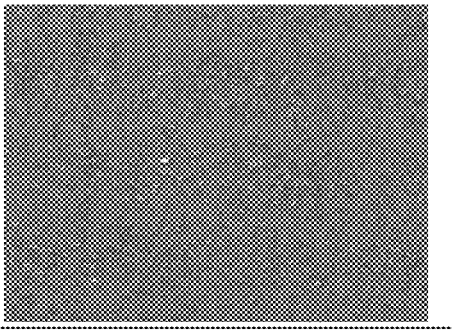 | 0.44 μm |
| EMERY PAPER GRINDING | 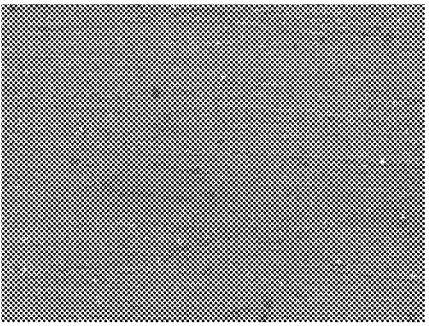 | 0.24 μm |
| DIAMOND PASTE GRINDING | 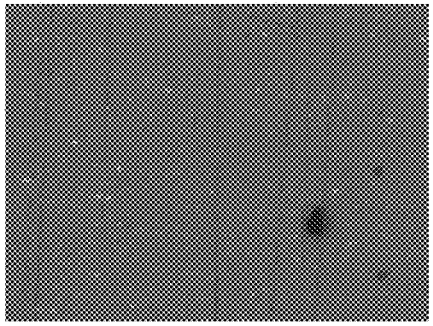 | 0.14 μm |
| GLASS WINDOW | 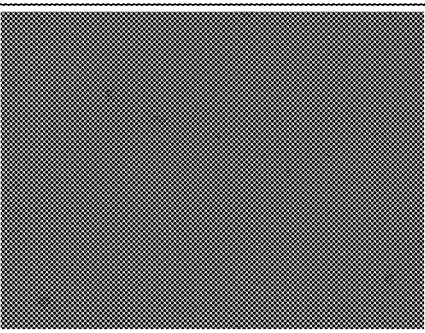 | 0.06 μm |

FIG. 36
| STATE OF SIDE FACE | LASER BEAM TRANSMISSION IMAGE @ MICROCHIP | LASER BEAM SPOT IMAGE @ SCREEN | LASER INTENSITY @ SCREEN |
|---|---|---|---|
| UNTREATED | 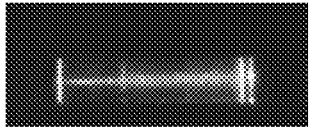 | 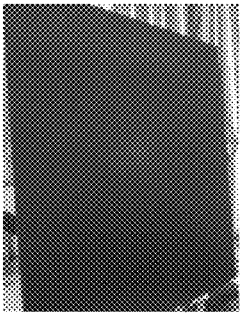 | 0.17mW (1%) |
| EMERY PAPER GRINDING | 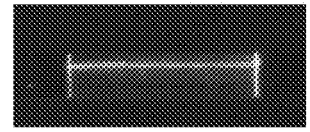 |  | 0.44mW (3%) |
| DIAMOND PASTE GRINDING | 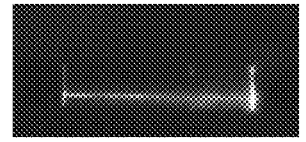 | 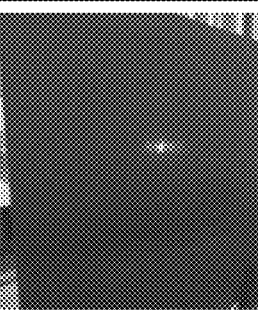 | 5.70mW (38%) |
| GLASS WINDOW | 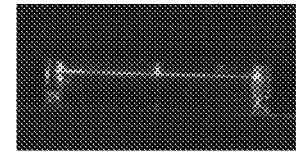 | 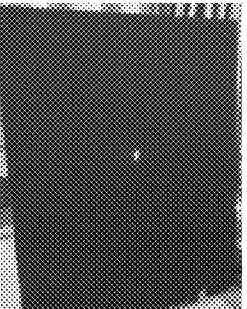 | 10.64mW (72%) |

MULTICHANNEL ANALYSIS DEVICE

TECHNICAL FIELD

The present invention relates to a microchip for analyzing a substance present at an inner portion thereof by subjecting the substance to florescence detection, or scattered light detection or the like highly sensitively by irradiating light of a laser beam or the like to plural channels provided at the inner portion and its fabricating method, a laser beam irradiating method, and a multichannel analyzer for analyzing a sample by using the microchip.

BACKGROUND ART

Research and development of a microchip for analyzing a sample of an organism substance or the like by fabricating a channel of a micrometer size or a channel which is a reaction tank on a chip have energetically been carried out over 20 years, and practical application is being progressed. There are a number of cases where a member of a microchip is configured by a transparent glass or resin, an outer dimension thereof variously ranges from several mm through several tens cm, and a thickness thereof is smaller than the size described above. A small amount of a sample can be analyzed simply and conveniently in a short time on the spot by a microchip. As examples of microchips which have already been put into practice, there are PCR, real time PCR, digital PCR, electrophoresis analysis, immunity analysis (immunoassay), flow cytometer (cell sorter), single cell analysis, microreactor, and so on. A microchip integrated with steps of analysis including introduction, extraction, mixing with a reagent, and reaction of a sample is referred to as a micro TAS (Total Analysis System) or Lab on a Chip, and research and development for resolving various problems toward practical application is successively and intensively carried out. As measuring means of a microchip, there are a number of cases where light measurement which can measure a substance present at an inner portion of the channel in noncontact. For example, a fluorescent substance is labeled on an organism substance in a channel, an unlabeled fluorescent substance is removed, then, fluorescence emitted by irradiating a laser beam is measured. Or an organism substance is observed by an optical microscope, and the shape or the number thereof is measured, and so on.

A microchip made of resin can be fabricated by a fabrication technology of injection molding, nanoimprinting or the like, and can be mass-produced at low cost, and therefore, the microchip is also disposable. Such a disposable microchip is particularly important in a field in which it is strongly requested to avoid contamination other than a sample to be analyzed such as medical diagnosis, food inspection or the like. It is important to configure a number of channels on a single chip, and measure the channels in parallel in a case where a number of items are analyzed in parallel concerning a single example, in a case where plural kinds of samples are measured in parallel, and in view of reducing cost per single analysis by improving a throughput of measurement thereby. Or a time-sequential change of a reaction or a separation can be analyzed by measuring plural portions of a single channel in parallel.

Here, it is a big problem how efficiently a laser beam is irradiated to plural channels provided on a microchip to thereby carry out an analysis by fluorescence measurement, scattered light measurement, transmitted light measurement or the like, and conventional methods are classified to following (1) through (5). A description will be given by taking an example or fluorescence measurement as follows. In any of the methods, laser beam irradiating portions of plural channels are arranged in parallel on the same plane in a chip. Hereinafter, the plane is referred to as an array plane. In a case where plural portions of a single channel are measured in parallel, portions of the channel which are intended to measure are arranged in parallel on the same plane in a chip by turning back the channel by plural times.

(1) Bean enlarging system: enlarging a laser beam to spread over plural channels to simultaneously irradiate and simultaneous detecting of fluorescence from the plural channels There are a case of enlarging a laser beam in a shape of a line and simultaneously irradiating plural channels and a case of enlarging a laser beam in a circular shape or an elliptical shape and simultaneously irradiating plural channels. In comparison with a case of irradiating a laser beam by focusing the laser beam to a single channel, in a case of simultaneously irradiating N channels, a laser beam intensity per single channel is reduced to $(1/N)$ or less when enlarged in the shape of the line, and to $(1/N^2)$ or less when enlarged in the shape of the circle. Therefore, fluorescence detection sensitivity of each channel is reduced. Although there is also conceivable a case of dividing a laser beam into plural pieces thereof and irradiating the respective laser beams to respective channels as one mode of the beam enlarging system, a problem similar to the above-described is posed.

(2) Beam scan system: when a system of focusing a laser beam to irradiate to a single channel and detecting fluorescence from the same channel is scanned with respect to plural channels When compared with a case where a laser beam is focused to a single channel and is not scanned, in a case of irradiating N channels serially by scanning, effective density of a laser beam intensity per single channel is reduced to $(1/N)$ or less, and fluorescence detection sensitivity of each channel is reduced. Further, also a time resolution of each channel is reduced to $(1/N)$ or less, which maybe disadvantageous in view of measurement. Further, a scanning mechanism is needed, and therefore, there is also a drawback that a device is large-sized, and requires high cost, and a failure is increased.

(3) Independent beam irradiation and detection system: systems of focusing a laser beam to irradiate a single channel, and detecting fluorescence from the same channel are installed by as many as plural channels Although when an optimum laser or an optimum detector can be used for each channel, high fluorescence detection sensitivity can be obtained for any channel, in this case, cost of the device is very high. On the other hand, plural channels which can be laid out on the same chip are obliged to be proximate to each other, and therefore, it is physically difficult to provide a highly sensitive laser irradiation fluorescence detection system for each channel. Therefore, it is necessary to adopt a small-sized laser irradiation fluorescence detection system at low cost in which sensitivity is not comparatively high.

(4) Beam waveguide system: irradiation of plural channels by an evanescent wave bypassing a laser beam to a light waveguide contiguous to plural channels, and simultaneous detection of fluorescence from plural channels A laser beam irradiation volume can be made to be very small by an evanescent wave, and therefore, the system is advantageous in a case where fluorescence originated from, for example, a single fluorescence molecule is detected highly sensitively by reducing background light originated from a solution in the channel. However, in many cases, an object substance detected by a microchip is not such a small number molecule but a large number molecule. In such a case, when a laser beam irradiation volume is excessively reduced, sensitivity is reduced.

(5) Beam side-entry system: irradiation of a laser beam to traverse plural channels vertically to long axes of respective channels along an array plane from a side face of a chip, and simultaneous detection of fluorescence from plural channels from a direction vertical to the array plane Although the highest sensitivity can be expected by the simplest and the most convenient configuration, a laser beam is refracted at an interface of each channel, and therefore, it is difficult to efficiently irradiate plural channels. Center positions of respective channels subjected to laser beam irradiation are arranged on the same linear line by the beam side-entry system. Hereinafter, the linear line is referred to as a beam side-entry axis. The beam side-entry axis is disposed on the array plane, and is vertical to long axes of respective channels. Here, the long axes of the respective channels are linear lines or curves passing centers in longitudinal directions of respective channels or gravitational centers of sections. In Patent Literature 1, a laser beam is irradiated by aligning the laser beam with the beam side-entry axis, and plural channels can be penetrated without deviating from beam side-entry axis by condensing a laser beam refracted by respective channels by inserting lenses or mirrors among the channels, and highly sensitive fluorescence detection can be carried out. On the other hand, in Nonpatent Literature 1, a laser beam is aligned with abeam side-entry axis, the irradiation is carried out by enlarging a width of the laser beam more than a channel width, and plural channels are simultaneously irradiated. In a case of irradiating by enlarging a laser beam width more than a channel width, a laser beam intensity density is reduced and fluorescence detection sensitivity is reduced.

CITATION LIST

Patent Literature

Patent Literature 1: JP 2011-59095 A

Nonpatent Literature

Nonpatent Literature 1: Anal. Chem., 2008, 80, 3897-3903

SUMMARY OF INVENTION

Technical Problem

The beam side-entry system in which a laser beam is irradiated simultaneously by penetrating plural channels by introducing the laser beam vertically to the long axes of the respective channels along the array plane of arranging the long axes of the plural channels in parallel in a focused state, for example, in a state of focusing a laser beam width to a degree equal to the channel width or less, is the most efficient laser irradiation fluorescence detection method, and a method enabling the highest sensitivity. In other words, the beam side-entry system is a system in which a laser beam irradiating one channel to pass therethrough also contributes to an irradiation of other channel. Here, a center axis of a laser beam in a case where the introduced laser beam straightly advances without being refracted in plural channels agrees with a beam side-entry axis that is defined previously. In comparison with other conventional system, the beam side-entry system has merits of an extremely high efficiency of utilizing a laser beam, a very small rate of advancing a laser beam into a detector directly or indirectly by reflection or the like, a very small rate of mixing Rayleigh scattering, Raman scattering, fluorescence or the like emitted by a member of a microchip by laser beam irradiation and the like with fluorescence which is a measurement object emitted from channels. Any of the merits contributes to realize highly sensitive fluorescence detection by a simple and convenient configuration.

According to Patent Literature, 1, a beam side-entry system is realized by inserting lenses or mirrors between channels, condensing a laser beam which is going to be deviated from a beam side-entry axis by being refracted in passing through a channel, passing a successive channel by returning the laser beam to the beam side-entry axis, and repeating the steps. However, it is difficult to actually arrange lenses or the like between channels. First, it is necessary to form spaces for inserting lenses or the like to a microchip. For example, it is necessary to machine holes of a size penetrating a microchip and capable of accommodating lenses or the like after fabricating a microchip including plural channels. Next, it is necessary to insert lenses or the like into the spaces and fix optical center axes of the lenses or the like in a state of being aligned with the beam side-entry axis. Here, the center axes of optical system of the lens or the like need to be positioned to both of long axis directions of the channels, and direction vertical to the array plane of the channels with an accuracy of a micrometer level. Further, the high accuracy positioning needs to be carried out for all of plural lenses or the like arranged between channels. Such a positioning accuracy is extremely difficult to be obtained only by machine accuracy in fitting each lens or the like to each hole provided at the microchip, and therefore, for example, after inserting individual lenses or the like among channels it is necessary to finely adjust to fix positions thereof. When center axis of each lens or the like is deviated from the beam side-entry axis, the laser beam is refracted from the beam side-entry axis, and therefore, plural channels cannot be irradiated simultaneously. The positioning described above takes labor and time and a mechanism for finely adjusting the positioning is separately needed, which amounts to an increase in a fabrication cost of a microchip. This is particularly disadvantageous in a case of using a microchip disposably.

Further, according to Patent Literature 1, positions of respective lenses or the like are fixed to a microchip while aligning a center axis of an introduced laser beam and center axes of respective lenses or the like, and therefore, the center axis of the introduced laser beam cannot freely be moved in long axes directions of respective channels. This is because, when the laser beam is away from the center axis of each lens or the like, the laser beam is refracted from the beam side-entry axis. It signifies that, for example it is impossible to set the beam side-entry axis where a flaw or a dirt in channels is not present and obtain high detection sensitivity. Similarly, it is impossible to enlarge a laser beam in long axes directions of respective channels to be horizontally incident thereon, or set plural beam side-entry axes positions of which are deviated in long axes directions of respective channels, and irradiate plural different laser beams to the respective ones. These signify that it is impossible to grasp behaviors of fluorescent substances present at the respective channels by two-dimensional images, and detect emittances of fluorescence of a number of different kinds of fluorescent substances respectively independently and highly sensitively.

Further, according to Patent Literature 1, lenses or the like are inserted between channels, and the lenses or the like are positioned highly accurately, and therefore, it is necessary to enlarge distances between contiguous channels, and there poses a problem that the number of channels which can be provided in a single microchip is made to be smaller than that of (1) beam enlarging system or (2) beam scan system of conventional examples.

On the other hand, according to Nonpatent Literature 1, in addition to a problem that a laser beam intensity density is reduced by carrying out irradiation by enlarging a laser beam width more than a channel width, there poses a problem that a laser beam is refracted in one direction by respective channels, and therefore, the laser beam is rapidly deviated from a beam side-entry axis in accordance with an increase in the number of channels through which the laser beam passes, and therefore, plural channels cannot be simultaneously irradiated efficiently. This is a problem which is newly found in the present invention, and a detailed description will be given in [Description of Embodiments].

The present invention presents a method of simultaneously irradiating a laser beam to plural channels provided at a single microchip by a beam side-entry system, and detecting fluorescence highly sensitively by a simple convenient configuration. This was achieved by resolving the problem described above involved in the conventional method of a beam side-entry system. At the same time, there will be shown a method of enabling to move an irradiating position and a beam side-entry axis of a laser beam in long axes directions of respective channels, and enabling to enlarge a laser beam in long axes directions of respective channels to irradiate, or irradiate plural different laser beams by deviating beam side-entry axes in long axes directions of respective channels. As a member of a microchip, an object thereof is made by not only glass but a resin having inexpensive unit cost. As a method of fabricating a microchip, an object is made not only by a method requiring time and cost of machining, stereo lithography, a semiconductor process working, but a method excellent in low cost performance and mass production performance of injection molding or nanoimprinting. For example, an injection molding using a resin member is excellent in low cost performance and mass production performance, and a method of realizing a beam side-entry system while using a microchip which can disposably be utilized will be presented.

Solution to Problem

A multichannel analyzer according to the present invention includes a microchip in which plural channel filled with a member of a refractive index $n_2$ at an inner portion of a transparent solid member of a refractive index $n_1$ are arranged such that long axes of the respective channels are substantially in parallel with each other at at least a portion of an area, and on the same plane or on the same circular cylinder face, a laser light source, an irradiation optical system for making a laser beam generated from a laser light source incident from a side face of the microchip substantially vertically to the long axes of the plural channels that is arranged substantially in parallel with each other, and a light detection optical system for respectively separating and detecting light emission from the plural channels by irradiating the laser beam, in which unlike a conventional beam side-entry system, a direction of the laser beam approaching the channel irradiated first is not made to be in parallel with a plane including both of the long axis of the channel irradiated first and the long axis of the channel irradiated last, but is made to a constant angle. Or, in a section including a center axis of the laser beam vertical to the respective channels, the direction of the laser beam approaching the channel irradiated first is not made to be in parallel with a linear line connecting a center of the channel irradiated first and a center of the channel irradiated last, but is made to have a constant angle.

In a case where the respective channels are arranged on the same plane, the plane coincides with an array plane, and in the section described above, in a case where the centers of the respective channels are arranged on the same linear line, the linear line described coincides with the beam side-entry axis. At this time, a direction of the laser beam approaching the channel irradiated first is made to be in a direction opposed to a direction in which the laser beam is refracted by the respective channels. Or, a direction of the constant angle described above is made to be a direction opposed to a direction of an angle by which the laser beam is refracted by the respective channels. As an example, when channel sections vertical to the long axes of the plural channels are in a tapered shape and $n_1 > n_2$, in a section of the channel irradiated first, if the laser beam is directed in a direction of widening a width of the tapered shape, a sign of a constant angle described above is made to be positive. Thereby, a distance until the laser beam is deviated from the channel array by refractions provided by the respective channels is increased, and more channels can be irradiated efficiently and simultaneously. Further, plural laser beams may be provided, and the plural laser beams may be made to be incident on different positions in long axes directions of the plural channels.

As an example, there is constructed a configuration in which a fluorescent material to be detected is a fluorescent material which is labeled to a sample originated from an organism, and fluorescence emitted from plural channels by irradiating a laser beam is detected simultaneously from a direction substantially vertical to an upper face or a lower face of a microchip.

Further, a method of fabricating a microchip according to the present invention is, as an example, a method of fabricating a microchip in which at an inner portion of a transparent solid member, plural channels are arranged such that long axes of the respective channels are in parallel with each other on the same plane or on the same circular cylinder face at at least a portion of an area, the method including a step of fabricating a first plate shape transparent solid member of a refractive index $n_1$ formed such that plural grooves having a sectional shape in a trapezoidal shape are in parallel with each other at at least a portion of the area by the injection molding, and a step of configuring the plural channels by the plural grooves by pasting a second plate shape transparent solid member of a refractive index $n_1$ onto the first plate shape transparent solid member.

Advantageous Effects of Invention

According to the present invention, a laser beam can efficiently and simultaneously be irradiated to plural channels provided in a single microchip by a beam side-entry system. Thereby, a system of realizing highly sensitive fluorescence detection of plural channels can be fabricated by exciting a fluorescence substance present at inner portions of respective channels, and simultaneously measuring emitted fluorescence from a direction vertical to an array plane of the respective channels or to an upper face or a lower face of the microchip. The microchip used to at this time can be fabricated inexpensively by a fabricating method having mass production performance of the injection molding or the like, and the microchip can be made to be disposable. Further, an optical system used in detection can be made to be simple and convenient, and a total of a system can be made to be small-sized at low cost.

A problem, a configuration, and an effect other than the above-described will be made to be apparent by a description of following embodiments.

BRIEF DESCRIPTION OF DRAWINGS

FIG. 34 shows diagrams indicating laser microscope images of a side face and a front face of a microchip and surface roughness.

FIG. 35 shows diagrams indicating measurement results of relationship between smoothing and surface roughness of side faces of microchips.

FIG. 36 shows diagrams indicating measurement results of smoothing of side faces of microchips and transmission performance of side-entry laser beams.

DESCRIPTION OF EMBODIMENTS

Figure 1:
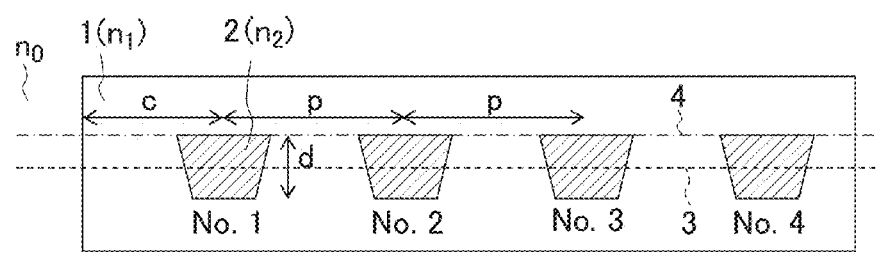
FIGS. 1(a) to 1(c) are explanatory views of a problem and a solution scheme of the present invention using a sectional view of a microchip including plural channels.
Figure 1:
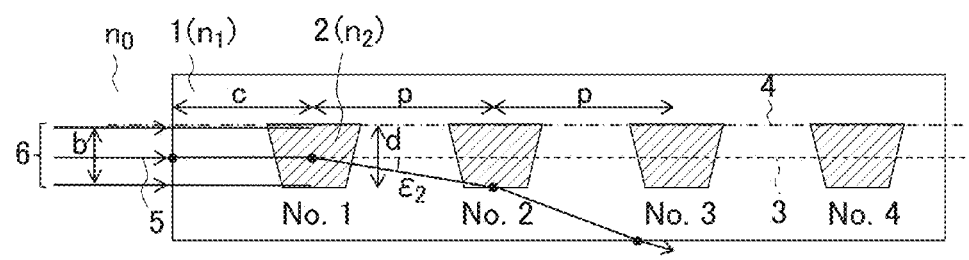
Figure 1:
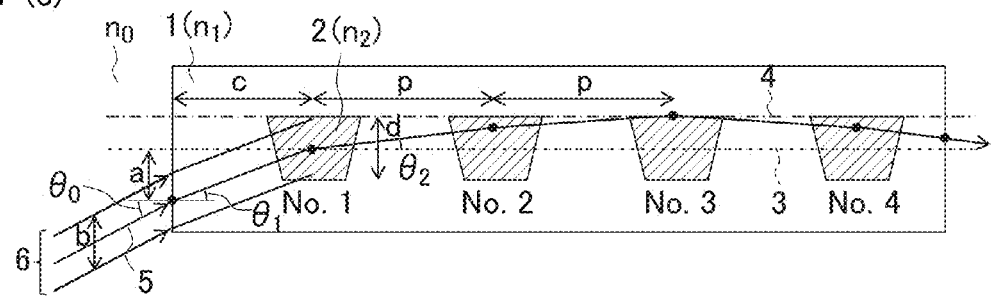

FIG. 1(a) shows schematic sectional views indicating a representative example of a microchip 1 having an array of plural channels 2 (hereinafter, referred to as channel array). This is a sectional view including a beam side-entry axis 3 (indicated by a dotted line in FIGS. 1(a) to 1(c)) of a microchip 1 and vertical to long axes of plural channels 2. A section of the microchip 1 is made by a rectangular shape, and a long side of the rectangle is in parallel with the beam side-entry axis 3 and the channel array. Long axes of the respective channels 2 are arranged in parallel with each other, on the same plane, and at a constant interval p. Center points of sections of the respective channels 2 in FIGS. 1(a) to 1(c) which are disposed on the long axes of the respective channels 2 are aligned on a linear line, and the linear line is aligned with the beam side-entry axis 3. The respective channels 2 are attached with numbers of No. 1, 2, 3, . . . in this order from a left side at which a laser beam is introduced to a right side. FIGS. 1(a) to 1(c) show Nos. 1 through 4. A distance between No. 1 channel and a left side face of the microchip 1 is c. Sections of the respective channels 2 are formed by a tapered shape, here, isosceles trapezoidal shape. A width in a direction vertical to the beam side-entry axis 3 of each channel 2, that is, a height of isosceles trapezoidal shape is d. The microchip 1 is placed in a medium of a refractive index $n_0$. Here, $n_0=1.00$ since the microchip is placed in air. A member of the microchip 1 is a transparent solid member of glass, resin or the like, and its refractive index is $n_1$. In contrast thereto, a member filled in the respective channels 2 is a liquid of an aqueous solution or the like or a gel state material, a refractive index thereof is $n_2$, and $n_2<n_1$.

As shown in FIGS. 1(a) to 1(c), the microchip 1 having the channel 2 with the section of isosceles trapezoidal shape can be fabricated by using a fabricating method excellent in mass production performance as the injection molding. The microchip 1 is composed of upper and lower parts which boundary is a lamination surface 4 (indicated in FIGS. 1(a) to 1(c) by a one-dotted chain line) including upper end faces of the respective channels 2. The microchip 1 is fabricated by laminating the upper part on the lower part through a method of thermocompression or the like. It is even better when the lamination surface 4 is made to be optically transparent, and does not include a layer of air or an adhering agent. The lamination surface 4 of the lower part before the lamination is provided with plural grooves, and the lamination surface 4 of the upper side before the lamination is a plane which is not provided with a groove. Therefore, even when a position of pasting together the upper and lower parts is deviated, shapes or the positions of the respective channels 2 are not influenced thereby. In the injection molding, there is needed a process of making a member of a resin or the like flow to a mold to solidify and thereafter drawing out the mold, and therefore, a sectional shape of the groove which can be formed needs to be a tapered shape in which a width is widened from a bottom of the groove toward the lamination surface 4. That is, when an upper base of isosceles trapezoidal shape is made to be a portion of the lamination surface 4, and a lower base thereof is made to be a bottom of the groove provided in the lower part, in a case of the microchip 1 in which width of upper base>width of lower base as in FIGS. 1(a) to 1(c), the process of drawing out the mold in the fabricating method of injection molding or the like is facilitated, and the mass production performance can be made to be high. A portion of a lower base angle of isosceles trapezoidal shape exceeding 90° is referred to as a draft angle. That is, when the draft angle is made to be D, the lower base angle of isosceles trapezoidal shape becomes 90°+ D. Although the draft angle D is 0°<D<90°, the larger the D, the more facilitated the process of drawing the mold, it is preferable that sectional shapes of the respective channels are uniform, and the smaller the D, the more preferable. In consideration of a working accuracy, it is preferable that the draft angle is made to be D>2°.

FIGS. 1(b) and 1(c) schematically show optical paths in cases of irradiating laser beams 6 to the microchip 1 of FIG. 1(a) by respectively different conditions. A configuration of the microchip 1 and conditions of irradiating the laser beams 6 shown herein are only representative examples for explaining a basic idea of the present invention, and other configurations and irradiation conditions based on a similar idea become naturally an object of the present invention. For example, the sectional shapes of the respective channels 2 may not be isosceles trapezoidal shape, and an array interval may not be constant.

As shown in FIG. 1(b), the laser beam 6 is irradiated from a left side face of the microchip 1 in a state of making a center axis 5 thereof is made to align with the beam side-entry axis 3 or in parallel therewith. A width of the laser beam 6 in a direction vertical to the array plane before being incident on the microchip 1, and until reaching No. 1 channel after having been incident on the microchip 1, that is, a width in a direction vertical to the beam side-entry axis 3 in FIG. 1(b) is b. The laser beam 6 is considered to be configured by a number of beam elements having an infinitesimal width. The laser beam 6 is made to irradiate the microchip 1 after having been collimated such that the respective beam elements are substantially in parallel with each other. Although in the beam elements, concerning the laser beam 6 on a left side of No. 1, beam elements of the center axis 5 and upper and lower ends are drawn, concerning the laser beam 6 on a right side of No. 1, only the center axis 5 is drawn as a representative, in FIG. 1(b).

As shown in FIG. 1(b), at every time of passing the respective channels 2, the laser beam 6 is refracted from the beam side-entry axis 3 to a side opposed to the lamination surface 4, or to a lower side from the beam side-entry axis 3, and is deviated from the channel array, and therefore, a number of the channels cannot be irradiated efficiently and simultaneously. The phenomenon can be explained as follows. An isosceles trapezoidal shape which is a sectional shape of each channel 2 can be regarded as a portion of a section of a prism of an isosceles triangle, a refractive index of the prism, that is, a refractive index $n_2$ of a member filled in the respective channels 2 is smaller than a refractive index of a surrounding of the prism, that is, the refractive index $n_1$ of the member of the microchip 1, and therefore, the laser beam incident on the prism is refracted to a side opposed to a bottom base of the isosceles triangle, that is, to a side of an apex angle. The problem was found first in the present invention.

Figure 2:
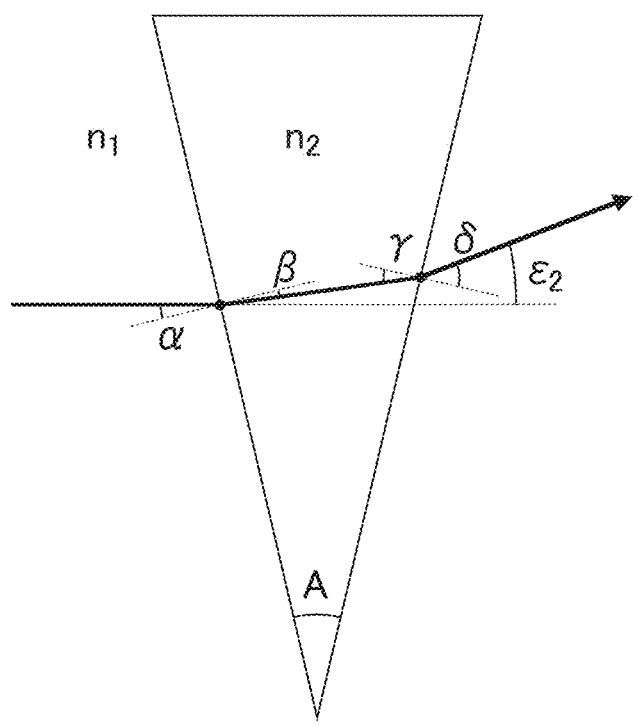
FIG. 2 is a view indicating a definition of a refraction angle of a laser beam incident on an isosceles triangular prism.

FIG. 2 is a view showing a definition of a refraction angle of a laser beam incident on an isosceles triangle prism, and the phenomenon is schematized to be easy to understand. A section of an isosceles triangle prism of an apex angle A comprising a member of the refractive index $n_2$ is disposed in a member of the refractive index $n_1$ by making a bottom side horizontal and making the apex angle direct downward. As is defined in FIG. 2, an incidence angle at an incidence face when a laser beam of a 0 width is assumedly made to be incident on the prism horizontally is made to be $\alpha$, a refraction angle is made to be $\beta$, an incidence angle at an outgoing face is made to be $\gamma$, a refraction angle is made to be $\delta$, and a net refraction angle when a laser beam passes through the prism is made to be $\epsilon_2$. Although all of $\alpha$, $\beta$, $\gamma$, and $\delta$ take a positive value between 0° and 90°, $\epsilon_2$ ranges $-90° < \epsilon_2 < 90°$, and a sign thereof is made to be positive in a case of refracting the laser beam to a bottom base side as shown in FIG. 2, and conversely, a case of refracting to an apex side is made to be negative. $\epsilon_2$ signifies a refraction angle when the laser beam 6 passes through the channel 2 in reference to FIGS. 1(a) to 1(c). Here, the following is established from the Snell's law and a geometrical relationship.

$$n_1 \times \sin \alpha = n_2 \times \sin \beta \quad (1)$$

$$n_2 \times \sin \gamma = n_1 \times \sin \delta \quad (2)$$

$$\gamma = A - \beta \quad (3)$$

$$\epsilon = \alpha + \delta - A \quad (4)$$

Further, when a draft angle of the injection molding is designated as D, $$A = 2D \quad (5)$$

is established, and an incident laser beam and a bottom base are in parallel with each other, and therefore, $$\alpha = D \quad (6)$$

is established. From the above-described, $$\epsilon_2 = \sin^{-1}[\sin\{2D - \sin^{-1}(\sin D \times n_1/n_2)\} \times n_2/n_1] - D \quad (7)$$

is expressed. Here, $n_2 > n_1$, and therefore, the refraction angle becomes as $\epsilon_2 < 0$. Therefore, in FIG. 2, the laser beam is refracted to an apex angle side when the laser beam passes through the prism, and in FIG. 1(b), the laser beam 6 is refracted in a direction of being remote from the beam side-entry axis 3, and in a direction opposed to the lamination surface 4 in passing through the channel 2. Further, in passing through the plural channels 2, the refraction angles described above are summed up, and therefore, the laser beam 6 is rapidly deviated from the channel array. Therefore, according to the configuration of FIG. 1(b), the efficiency is not necessarily excellent for simultaneously irradiating plural channels 2 by making the laser beam 6 aligning with the beam side-entry axis 3.

Hence, as shown in FIG. 1(c), the center axis 5 of the laser beam 6 is not made to align with the beam side-entry axis 3 or not made to be in parallel therewith, but is inclined to the beam side-entry axis 3 by $\theta_0$ (>0) and is introduced from a left side face of the microchip 1, and is inclined to the beam side-entry axis 3 by $\theta_1$ (>0) to irradiate No. 1, channel. Also in this case, the laser beam 6 is irradiated to the microchip 1 after having been collimated such that the respective beam elements are substantially in parallel with each other. Here, the left side face of the microchip 1 is made to be vertical to the beam side-entry axis 3, and therefore, $$\theta_1 = \sin^{-1}(1/n_1 \times \sin \theta_0) \quad (8)$$

Both of the signs of the angles $\theta_c$ and $\theta_1$ are made to be positive in a case where the laser beam 6 advances in a direction of being directed from the beam side-entry axis 3 to the lamination surface 4, that is, in a right upper direction of FIGS. 1(a) to 1(c) similarly to the case of the angle $\epsilon_2$. In other words, the signs of the angles $\theta_0$ and $\theta_1$ are made to be positive when the laser beam 6 is directed from a lower part of the microchip 1 provided with grooves to an upper part without the grooves. Or the sign of the angle $\theta_1$ is made to be positive when the laser beam 6 is directed in a direction of widening a width of the tapered shape in a section of No. 1 channel, that is, in approaching to No. 1 channel from a narrow width side to a wide width side of the tapered shape.

At this time, a distance in a direction of the beam side-entry axis 3 until the laser beam 6 is deviated by the refraction angle $\epsilon_2$ (<0) from the channel array to a side opposed to the lamination surface 4 is increased thanks to $\theta_0 > 0$ and $\theta_1 > 0$, and more number of channels 2 can simultaneously be irradiated by the beam side-entry system. Here, No. 1 channel is made to be able to be irradiated excellently by controlling a distance between the laser beam 6 (or, the center axis 5) and the beam side-entry axis 3 at the left side of the microchip 1 as a (>0). In order to efficiently realize the beam side-entry system, a magnitude of $\theta_1$ may not be excessively large or excessively small, and it is important that the magnitude is in a pertinent range.

First, consider an upper limit of $\theta_1$. For example, when $\theta_1 = 90°$, that is, in a case where the laser beam 6 is irradiated from a lower side of the microchip 1 to an upper side vertically to the beam side-entry axis 3, the laser beam 6 passing through No. 1 channel 2 cannot irradiate channels of No. 2 and thereafter, and therefore, the beam side-entry system cannot be carried out, and the plural channels cannot be irradiated efficiently and simultaneously. In order to realize the efficient beam side-entry system, it is necessary that the laser beam 6 irradiated and passed through No. 1 channel irradiates at least No. 2 channel. For that purpose, a beam element which is incident on a lower end of No. 1 channel may be incident on a lower position than an upper position of No. 2 channel, and the condition is as follows.

$$p \times \tan \theta_2 < d \quad (9)$$

Here, as shown in FIG. 1(c), $\theta_2$ is an angle of a beam element being directed from No. 1 channel to No. 2 channel to the beam side-entry axis 3 and is given as follows.

$$\theta_2 = \theta_1 + \epsilon_2 \quad (10)$$

Similarly, an angle $\theta_3$ made by a beam element directed from No. 2 to No. 3 and the beam side-entry axis 3, an angle $\theta_4$ made by a beam element directed from No. 3 to No. 4 and the beam side-entry axis 3, further, an angle $\theta-$, made by a beam element directed from No. (L-1) to No. L and the beam side-entry axis 3 are given as follows.

$$\theta_3 = \theta_2 + \epsilon_2 = \theta_1 + 2\epsilon_2 \quad (11)$$

$$\theta_4 = \theta_3 + \epsilon_2 = \theta_1 + 3\epsilon_2 \quad (12)$$

. . .

$$\theta_L = \theta_{L1} + \epsilon_2 = \theta_1 + (L-1)\epsilon_2 \quad (13)$$

Here, L indicates the total number of channels which are simultaneously irradiated. A way of attaching the signs of $\theta_2$, $\theta_3, \theta_4, \ldots, \theta_L$ is the same as that in the case of $\theta_1$ and $\epsilon_2$. $\theta_1, \theta_2, \theta_3, \theta_4, \ldots \theta_L$ start from positive values and are converted into negative values in the middle. In the example of FIG. 1(c), although $\theta_1$ through $\theta_3$ are positive values, $\theta_4$ and thereafter are converted into negative values, and therefore, a light ray of the center axis 5 is refracted to an upper direction until No. 3 channel, whereas thereafter, the light ray is refracted in a lower direction. Generally, when the positive value is converted into the negative value at $\theta_{M|1}$, No. M channel immediately therebefore is expressed as follows.

$$M = \text{int}(-\theta_1/\epsilon_2 + 1) \quad (14)$$

Here, int(X) is a function of deriving an integer portion of X. In order to realize the beam side-entry system more efficiently than in Equation (9), a beam element incident on a lower end of No. 1 channel may be incident on a lower position than an upper end of No. M channel, and the condition thereof is as follows.

$$p \times \tan \theta_2 + p \times \tan \theta_3 + \ldots + p \times \tan \theta_M < d \quad (15)$$

Next, consider a lower limit of $\theta_1$. In a case of $\theta = 0°$, the case is as shown by FIG. 1(b), and the efficiency of the beam side-entry system is poor. That is, a minimum condition is as follows.

$$\theta_1 > 0 \quad (16)$$

In order to realize a further efficient beam side-entry system, it is necessary that the laser beam 6 which has irradiated and passed through No. 1 channel at least irradiates No. 2 channel. For that purpose, an angle $\theta_2$ of a beam element which has passed through No. 1 channel relative to the beam side-entry axis 3 may be a positive value, and its condition is as follows from Equation (10).

$$\theta_2 = \theta_1 + \epsilon_2 > 0 \quad (17)$$

According to the present invention, as shown in FIG. 1(c), the laser beam 6 is irradiated from the side of the microchip 1. On the other hand, consider a case of irradiating the laser beam 6 from a lower face of the microchip 1. The angle $\theta_1$ of the laser beam 6 irradiating No. 1 channel relative to a lower face direction, or the beam side-entry axis 3, and is expressed as follows, unlike Equation (8). As described later, $\theta_1$ by Equation (18) is very large in comparison with $\theta_1$ by Equation (8), and therefore, by $\theta_1$ Equation (18) compatible with Equation (9) or Equation (15) is not present.

Therefore, according to the present invention, the configuration of irradiating the laser beam 6 from the side face of the microchip 1 is a necessity, and the present invention is not applicable to a case of irradiating the laser beam 6 from a lower face or an upper face of the microchip 1. It is a point in which the configuration basically differs from (1) beam enlarging system, and (2) beam scan system which are conventional methods.

Successively, a description will be given of a method of simultaneously irradiating a number of the channels 2 further efficiently by the beam side-entry system by enlarging the width b in a direction vertical to the beam side-entry axis 3 of the laser beam 6. According to the configuration of FIG. 1(c), in comparison with the configuration of FIG. 1(b), more numbers of channel 2 can simultaneously irradiated by the beam side-entry system. However, the number of the channels 2 which individual beam elements can simultaneously irradiate by the configuration of FIG. 1(c) is about 2 through 3 times as much as that in the case of the configuration of FIG. 1(b). Here, when the width b of the laser beam 6 is enlarged more than the width d of the respective channels 2, in addition to the fact that the beam element which irradiates the No. 1 channel 2 first irradiates the channel 2 of No. 2 and thereafter as shown in FIG. 1(c), a beam element which irradiates the channel 2 of No. 2 and thereafter first is present, such a beam element can further irradiate the channel 2 thereafter, as a whole, more channels 2 can be irradiated further uniformly. Here, an enlargement of the width b of the laser beam 6 brings about a reduction in a beam intensity density, and therefore, a balance therebetween is important. However, at least, in comparison with (1) beam enlarging system which is a conventional method, owing to the beam side-entry system, that is, since the specific beam element contributes to irradiation of plural channels, and therefore, efficient simultaneous irradiation can be carried out.

The width b of the laser beam 6 which is suitable for realizing the efficient beam side-entry system depends on the total number L of the channel 2 to be irradiated simultaneously. Here, L does not necessarily agree with the total number of the channel 2 included in the microchip 1. When the beam element which irradiates first the respective L channel 2 is present, all of L channels 2 can simultaneously be irradiated. For that purpose, a width in a direction of the beam side-entry axis 3 of the laser beam 6 incident from the left side face of the microchip 1 may be larger than a distance between No. 1 channel 2 and No. L channel 2: p X (L-1), and its condition is as follows.

$$b > p(L-1)\tan \theta_1 \quad (19)$$

Next, consider a condition of simultaneously irradiating all of the L channels 2 further efficiently while reducing a magnitude of b less than that in Equation (19). When the number of the channels 2 which individual beam elements can simultaneously irradiate by the configuration of FIG. 1(c) is twice as much as that in the case of the configuration of FIG. 1(b) as a typical example, the number can be expressed as 2×M−1 by using Equation (14). Here, in FIG. 1(c), it is assumed that both of the number of channels in which the laser beam 6 is traveled in the upper direction and converted into a lower direction, and the number of channels in which the laser beam 6 is traveled in the lower direction and is deviated from the channel array are assumed as M. That is, when a beam element irradiating first L−(2M−1) channels 2 is present, the beam element can simultaneously irradiate all of the L channels 2. For that purpose, a width of the laser beam incident on the left side of the microchip 1 in a direction of the beam side-entry axis 3 may be larger than the distance between No. 1 channel and No. {L−(2×M−1)}:p×[{L−(2M−1)}−1]=p(L−2M), and a condition thereof is as follows.

$$b > p(L-2M)\tan\theta_1 \tag{20}$$

As described above, the description has been given of an effect of enlarging the width b of the laser beam 6 in the direction vertical to the array plane, that is, the width b in the direction vertical to the beam side-entry axis 3 in FIG. 1(b) and FIG. 1(c) more than the width d of the channel 2 in the direction vertical to the beam side-entry axis 3. On the other hand, there is frequently a case where a similar enlargement is not carried out concerning a width of the laser beam 6 in a direction in parallel with the array plane, that is, a width in a long axis direction of each channel 2, for example, the width is made to be to a degree the same as that of the width d of the channel 2. There are two reasons therefor. One is that in a case where a substance subjected to electrophoresis is analyzed by the laser beam irradiation and fluorescence detection at an inner portion of each channel 2, when a laser beam width in a long axis direction of each channel 2 is larger than the width of each channel 2, an electrophoresis resolution is reduced. The other is that when the laser beam 6 is enlarged not only in the direction orthogonal to the array plane, but in the direction in parallel therewith, the laser beam intensity density is reduced by that amount, and therefore, the irradiation efficiency and the fluorescence detection sensitivity of each channel 2 are reduced. Therefore, it is preferable to enlarge the laser beam only in a direction vertical to the array plane by using a cylindrical lens or the like, that is, to irradiate the microchip 1 and each channel 2 by shaping a section of the laser beam 6 to be in an elliptical shape, or a line shape.

A direction of measuring scattered light or fluorescence from each channel 2 by irradiating the laser beam 6 may be an upper direction or a lower direction of the microchip 1 in FIG. 1(c). That is, even when FIGS. 1(a) to 1(c) are inverted, a content of the invention described above is not influenced thereby. However, it is preferable for improving fluorescence detection sensitivity of each channel 2 and reducing dispersion that a center axis of a light detection system is made to be vertical to an array of the channel 2, at least either of the upper face or the lower face of the microchip 1 as described later in reference to FIGS. 5(a) to 5(c). Therefore, although as described above, $\theta_0, \theta_1, \theta_2, \ldots, \theta_L$ are defined as angles made by the beam side-entry axis 3 of the laser beam 6 or the array plane, these angles maybe defined as angles relative to a plane vertical to the center axis of the light detection system.

On the other hand, it is effective in view of irradiating more channels 2 to subject a lower base face and an upper base face of each channel 2 to a modification of coating or the like such that the laser beam 6 is made to be easy to be reflected. Naturally, only one of the lower base face or the upper base face may be coated. In subjecting the upper base face to the coating, the coating may be provided to a total of the lamination surface 4 of an upper part of the microchip 1.

Figure 3:
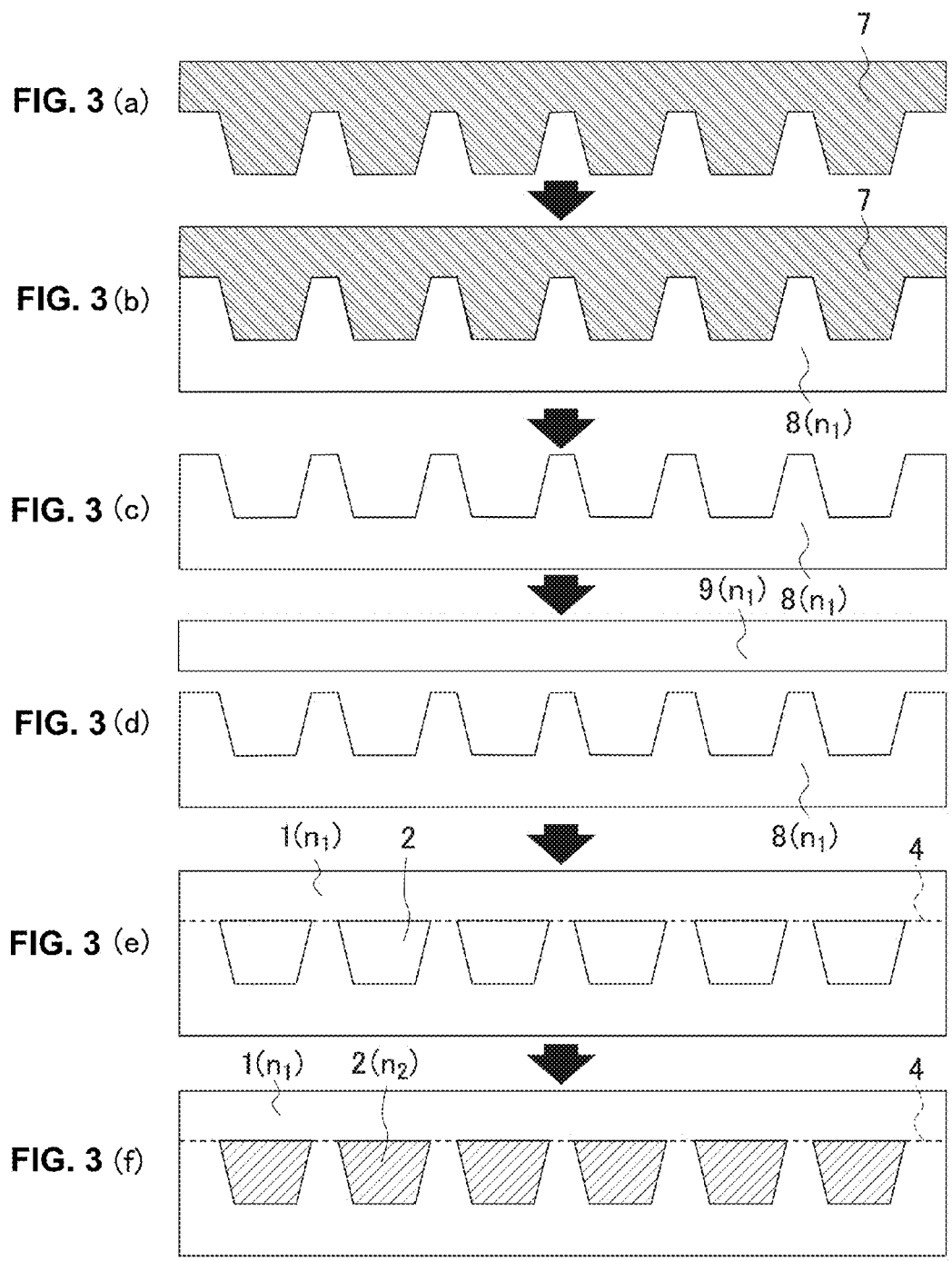
FIGS. 3(a) to 3(f) show step diagrams indicating a fabrication process of a microchip.

FIGS. 3(a) to 3(f) show step diagrams indicating a process of fabricating the microchip 1 shown in FIGS. 1(a) to 1(c) by the injection molding by schematic views of sections. To a mold 7 shown in FIG. 3(a), a member heated to melt a transparent resin is injected as in FIG. 3(b) to cool and solidify. Next, by drawing the mold 7, a part 8 having plural grooves which becomes the channels 2 of the microchip 1, that is, the lower part of the microchip 1 is obtained as shown in FIG. 3(c). The member of the part 8 is a transparent solid member having a refractive index $n_1$. The part 8 is formed with plural grooves having a trapezoidal sectional shape on a surface of a plate shape transparent solid member. The grooves are arranged in parallel with each other at least a portion of an area.

On the other hand, as shown in FIG. 3(d), a transparent solid member having a refractive index $n_1$ in a plate shape is separately fabricated as a part 9 which does not have the grooves, that is, the upper part of the microchip 1, pasted together with the part 8 at the lamination surface 4 by thermocompression bonding or the like, and as shown in FIG. 3(e), the microchip 1 having the refractive index $n_1$ is obtained. That is, by the step, the plural channels 2 are configured at an inner portion of the microchip 1 by plural grooves formed on the surface of the part 8. In such a state, the inner portion of any channel 2 is also filled with air. Finally, as shown in FIG. 3(f), the channel 2 is fabricated by filling a medium of a refractive index $n_z$ used for analysis to the plural channels 2. The microchip 1 is distributed to a user in a state of, for example, FIGS. 3(e) or 3(f). The part 9 may be of a shape of a thin sheet having flexibility since a surface thereof is a plane, for example, a thickness thereof may be about 100 μm. Fabrication of the part 9 in a thin sheet shape in this way contributes to reduce a fabrication cost of the microchip 1. According to the present embodiment, a direction of refracting the laser beam 6 is in a direction of being remote from the lamination surface 4, and therefore, a problem by thinning the thickness of the part 9 is not particularly posed.

Although in the above-described, a consideration has been given of a case where a sectional shape of the channel 2 is the shape of isosceles trapezoid, a consideration can similarly be given to a case of a shape of a trapezoid which is not isosceles. When two base angles of the trapezoidal shape are made to be $90°+D_L$ ( $0°<D_L<90°$) and $90°=D_3$ ( $0°<D_R<90°$), when $D=(D_L+D_R)/2$, relationships of Equations (5) through (7) may be applied as they are proximately. Further, even when sectional shapes of plural channels are configured by trapezoidal shapes which are not the same, it may be considered that the above-described relationships are established similarly when $D_L$, $D_R$, and D of averages of these are used.

Further, a similar effect can be achieved even when a sectional shape of the channel 2 is other than a trapezoidal shape. A sectional shape of the channel 2 which can be fabricated by a fabricating method of at least injection molding or nanoimprinting becomes an object. For example, the similar effect can be achieved even in a trapezoidal shape which is not isosceles, a triangular shape, or even when respective sizes are not configured by linear lines but a circular arc shapes, or even when corners of a trapezoidal shape or a triangular shape is rounded. In a case of such a general sectional shape, the above-described relationship may be considered to be established by calculating D as follows.

A minimum value of a width of a sectional shape of each channel in parallel with the beam side-entry axis is $W_{min}$, and a maximum value thereof is $W_{max}$, and a maximum value of a width vertical to the beam side-entry axis is d. Here, since a sectional shape is made to be a tapered shape, $W_{min}$ is obtained at a position the remotest from the lamination surface, and $W_{max}$ is obtained at a position the nearest to the lamination surface. When an average inclination of the tapered shape is considered, it is established that $D=90-\tan^{-1}\{2d/(W_{max}-W_{min})\}$. In a case where sectional shapes of plural channels are not the same, an average value of D calculated in this way may be used. Further, although the respective channels are arranged at equal intervals, the similar effect is achieved even when the respective channels are not arranged at equal intervals in this way. In such a case, an average value of the interval may be made to be p.

Another resolution scheme is shown as follows for a new problem which has been found first by the present invention, that is, a problem in which as shown in FIG. 1(b), when the laser beam 6 is made to be horizontally incident by aligning with the beam side-entry axis 3, the laser beam 6 is deviated from the beam side-entry axis 3 and the array of the channels 2 by refraction provided by the channels 2, and a number of the channels 2 cannot efficiently be irradiated.

Figure 4:
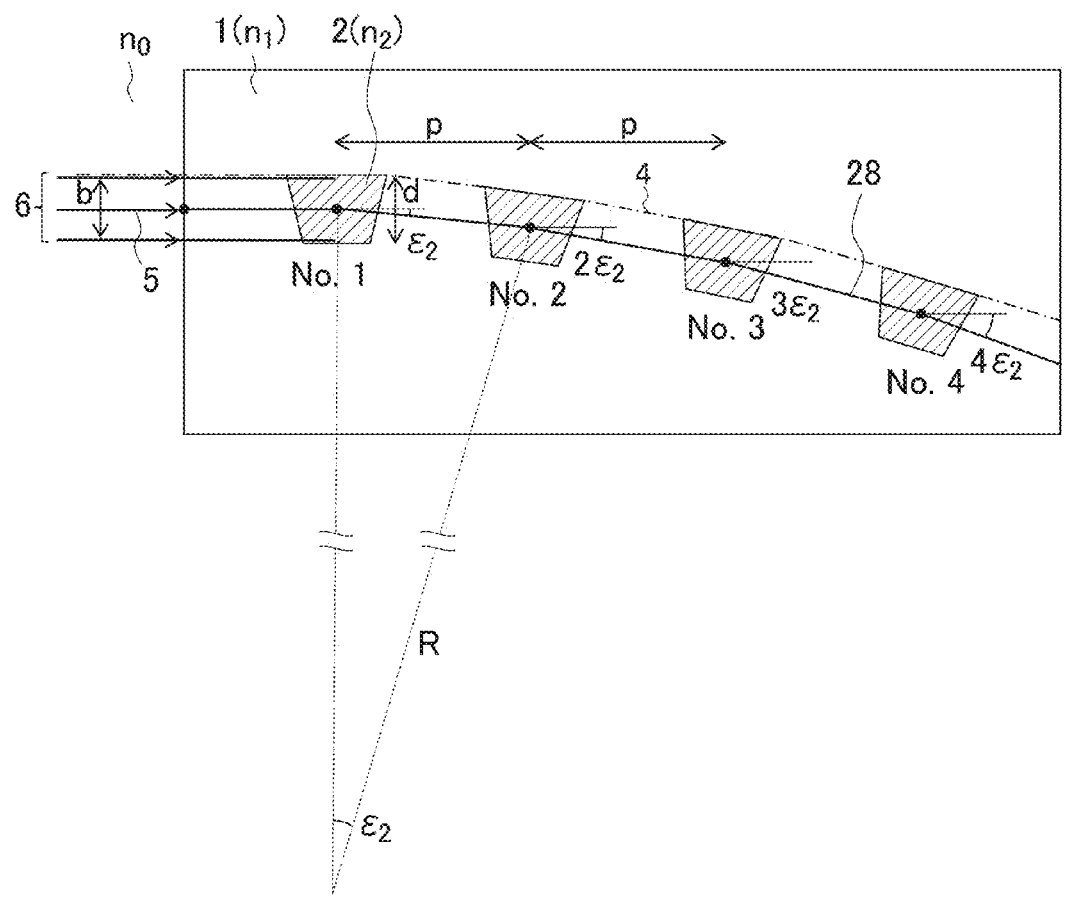
FIG. 4 shows schematic views of a section of a microchip including plural channels indicating a solution scheme of the present invention.

FIG. 4 is a schematic sectional view of a microchip including plural channels showing the other resolution scheme. As shown in FIG. 4, center positions of the respective channels 2 irradiated with the laser beam are not aligned on the same linear line, that is, on the beam side-entry axis 3, but are aligned on a curve, that is, on a beam side-entry curve 28. Also the channel array is mounted not on a plane including the beam side-entry axis 3 but on a curved surface including the beam side-entry curve 28. That is, the long axes of the plural channel 2 are aligned on a cylindrical face having a radius of curvature R. Sections vertical to long axes of the plural channels are in a tapered shape (here, isosceles trapezoidal shape). No. 1 channel is irradiated by the laser beam 6 such that the center axis 5 is in parallel with an upper base and a lower base of the isosceles trapezoidal shape configuring a section of No. 1 channel 2, that is, $\theta_1=0°$ similar to FIG. 1(b), and the center axis 5 passes through a center of No. 1 channel 2. At this time, the laser beam 6 transmitted through No. 1 channel 2 advances by configuring an angle of $\epsilon_2$ relative to the laser beam 6 before being incident on No. 1 channel 2 by refraction by No. 1 channel 2. Hence, an arrangement of No. 2 channel 2 is adjusted such that the center axis 5 is in parallel with an upper base and a lower base of an isosceles trapezoidal shape configuring a section of No. 2 channel 2, and passes through a center of No. 2 channel 2. Then, the laser beam 6 which has transmitted through No. 2 channel 2 advances by configuring an angle of $2\times\epsilon_2$ relative to the laser beam 6 before being incident on No. 1 channel 2 by refraction by No. 2 channel 2. The laser beam 6 advances along the beam side-entry curve 28 by arranging centers of the respective channels 2 of No. 1, No. 2, No. 3, ... on the beam side-entry curve 28 such that the above-described is repeated, and is not deviated from the channel array on the circular cylindrical face, and therefore, a number of the channels 2 can efficiently be irradiated simultaneously.

At this time, also the lamination surface 4 is curved similarly to the beam side-entry curve 28. The beam side-entry curve 28 is curved in a direction the same as a direction of propagation of the laser beam 6 curved by refraction by the respective channels 2. That is, the beam side-entry curve 28 is curved in a direction of being directed from an upper base to a lower base when upper base>lower base in an isosceles trapezoidal shape of a section of the channel 2. Or, the beam side-entry curve 28 is curved in a direction inverse to a direction of being directed to the lamination surface 4 of the microchip 1 from a center of the channel 2. At this time, it is preferable that the radius of curvature R indicating a degree of curving is made to be constant in any position in the microchip 1 when the array interval p of the channel 2 is constant. That is, it is preferable to curve the arrangement positions of the channels 2 by a constant radius of curvature R over an area of arranging the plural channels 2 which are going to be measured. An ideal radius of curvature R is expressed as follows.

$$R=p/|\epsilon_2| \tag{21}$$

In a case where the array intervals of the plural channels 2 are not constant, an average value of the array intervals is made to be p. At this time, in principle, however large the number of the channels 2 is increased, the laser beam 6 is not deviated from the channel array, ideal beam side-entry irradiation can be realized. Actually, efficient beam side-entry irradiation can be realized even in being deviated from the ideal value described above, and a condition thereof satisfies at least the following equation.

$$p/|2\epsilon_2|<R<p/|\epsilon_2/2| \tag{22}$$

Further, a condition of increasing an efficiency satisfies the following equation.

$$p/|1.2\epsilon_1|<R<p/|0.8\epsilon_2| \tag{23}$$

A detailed description will be given of grounds and effectiveness of Equation (21), Equation (22), and Equation (23) described above in fourth embodiment.

Although in FIG. 4, the upper face and the lower face of the microchip 1 are in parallel with the direction of the laser beam 6 before being incident on No. 1 channel 2, and a left side face and a right side face of the microchip 1 are drawn vertically to the direction of the laser beam before being incident on No. 1 channel 2, it is apparent that these are not necessary configurations. Further, a direction of measuring scattered light or fluorescence from each channel 2 by irradiating the laser beam 6 may be from an upper direction or from a lower direction of the microchip 1. That is, even when FIG. 4 is inverted to make upside down, a content of the invention described above is not influenced thereby. In a case of irradiating a total of L channels 2 of No. 1, through No. L by the laser beam 6 to detect light in accordance with FIG. 4, it is preferable in view of improving light detection sensitivity and reducing dispersion to make a center axis of a light detection system vertical to a plane including both of the long axis of No. 1 channel 2 and the long axis of No. L channel 2.

Further, an array of the plural channels 2 and the laser beam 6 provided at the microchip shown in FIG. 4 is an arrangement in which $\theta_1$ made by a laser beam approaching No. 1 channel relative to a plane including respective long axes of No. 1 channel irradiated first by the laser beam and No. L channel finally irradiated by the laser beam is made to be $\theta_1>0$.

A description will be given of embodiments of the present invention as follows.

[First Embodiment]

FIGS. 5(a) to 5(c) are outline explanatory views showing an example of a multichannel analyzer according to the present invention. The present embodiment shows a system of carrying out electrophoresis analysis of DNA included in an organism sample, FIG. 5(a) is a bird's eye view of a microchip 1, FIG. 5(b) shows a section including the beam side-entry axis 3 of the laser beam 6 for the microchip 1 configuring the system, a section of a fluorescence detection optical system 13 through 16, and a data analyzing device 17, and FIG. 5(c) shows a two-dimensional fluorescence image 18 provided by the two-dimensional sensor 16. Wavelength dispersion images 19 of a laser scattered light and fluorescence from respective channels 2 excited by the laser beam 6 are measured independently from each other. By the above-described configuration, the number of kinds of fluorescence which can be detected simultaneously by the respective channels 2 can be increased, and a small amount of fluorescence can be identified by separating and detecting different kinds of fluorescence accurately. According to the present embodiment, a throughput is improved by labeling different samples by respectively different fluorescent materials and simultaneously analyzing by the same channel.

Figure 5:
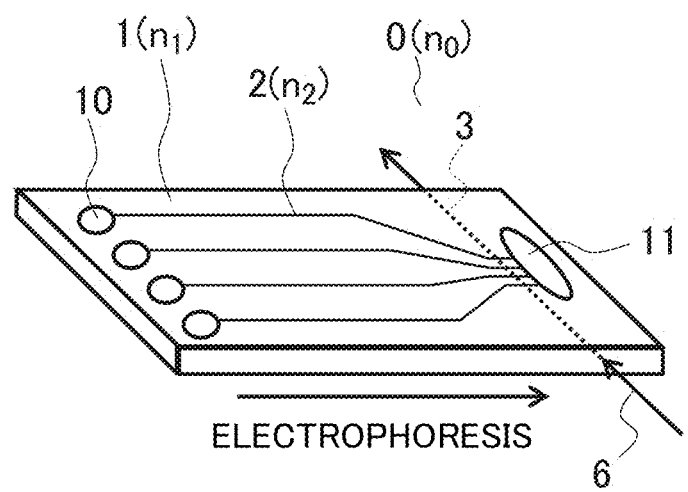
FIGS. 5(a) to 5(c) are outline explanatory views showing an example of a multichannel analyzer according to the present invention.
Figure 5:
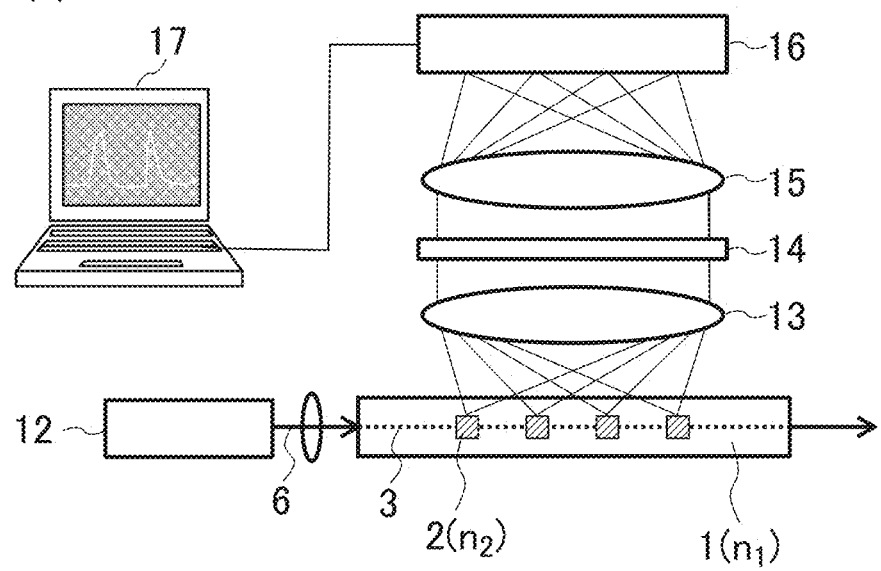
Figure 5:
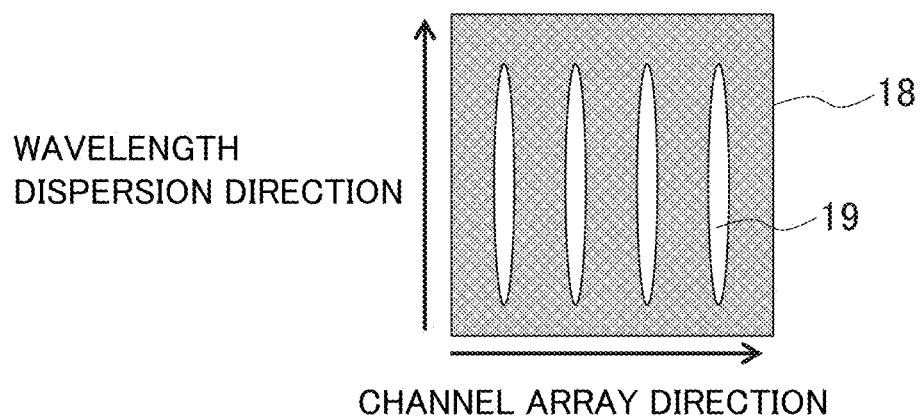

As shown in FIG. 5(*a*), the microchip 1 configured by a member of a refractive index $n_1$ is arranged in a medium 0 of a refractive index $n_0$, and plural channels 2 filled with a member of a refractive index $n_2$ are aligned in the microchip 1. Inlet ports 10 are provided to the respective channels 2, and an outlet port 11 common to the respective channels 2 is provided. Although cross injection units or double T injection units are provided at the respective channels 2 at vicinities of the inlet ports 10, the units are omitted in FIGS. 5(*a*) to 5(*c*). In DNA in the sample, an interested segment is previously amplified, and a fluorescent material is labeled. After introducing the sample, DNA labeled by the fluorescent material included in the sample is separated by electrophoresis from the inlet port 10 to the outlet port 11 by applying a voltage on both ends of each channel 2 by connecting a negative electrode to the inlet port 10 and connecting a positive electrode to the outlet port 11. According to the plural channels 2, long axes of the respective channels are arranged substantially in parallel with each other at least a portion of an area. A laser beam which is generated from a laser light source and incident from a side face of the microchip is made to be irradiated on the plural channels substantially vertically to long axes of the plural channels.

As shown in FIG. 5(*b*), the laser beam 6 emitted from the laser light source 12 is focused by an irradiation optical system including a lens, introduced from the side face of the microchip 1, and irradiates the respective channels 2. Although FIGS. 5(*a*) and(*b*), for simplicity, the center axis 5 of the laser beam 6 introduced to the microchip 1 and the beam side-entry axis 3 are expressed to align with each other or to be in parallel with each other, accurately, as described above, or as is described later in reference to FIG. 21, these have significant angles. DNA labeled by fluorescent material subjected to electrophoresis in the respective channels 2 is excited by the laser beam 6 in traversing a position of being irradiated by the laser beam 6, and emits fluorescence. The fluorescence emitted from the respective channels 2 are detected by a fluorescence detection optical system. That is, fluxes of the fluorescence are made to be parallel light flux by a common condensing lens 13, transmit through a filter and a diffraction grating 14, and imaged on a sensor face of a two-dimensional sensor 16 by an imaging lens 15. The filter is provided for cutting off a wavelength of the laser beam 6 which becomes background light in detecting fluorescence, and the diffraction grating is provided for detecting multiple colors by dispersing the wavelength of the fluorescence. Further, a section of the channel 2 is configured by the same shape with regard to a long axis direction of the channel 2, and therefore, even when a position of the laser beam 6 incident on the microchip 1 is more or less deviated in the long axis direction of the channel 2, the similar effect is achieved, and the fluorescence detection sensitivity is not influenced thereby.

FIG. 5(*c*) is a schematic view showing a two-dimensional fluorescence image 18 provided by the two-dimensional sensor 16. A direction of wavelength dispersion is parallel to a long axis direction of each channel 2 (a direction vertical to a sectional view of FIG. 5(*b*)), that is, vertical to an array direction of the plural channels 2, and therefore, the wavelength dispersion images of emitted fluorescence from the respective channels 2 do not overlap each other, and are measured independently from each other. Here, wavelength dispersion images 19 of laser beam scattering and fluorescence which cannot be removed by the filter are obtained from the respective channels 2. Signals of the fluorescence measured in this way are analyzed by the data analyzing device 17, and samples introduced to the respective channels 2 are analyzed.

Figure 21:
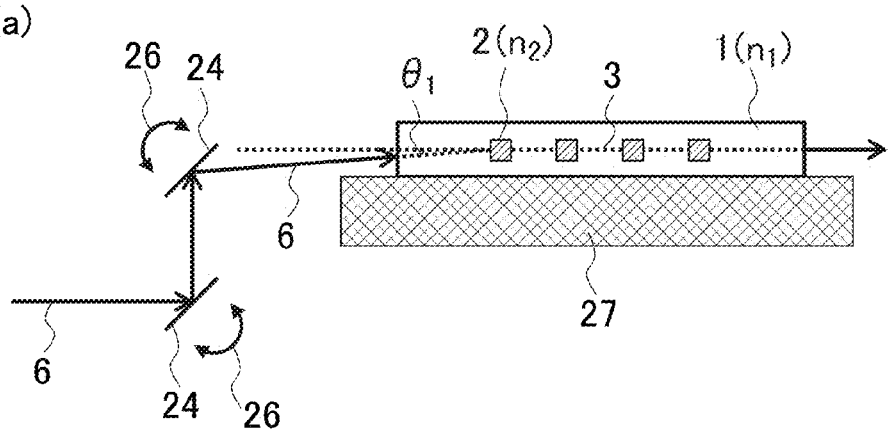
FIGS. 21(a) and 21(b) show explanatory views indicating a mechanism of controlling an angle made by a laser beam and a beam side-entry axis.
Figure 21:
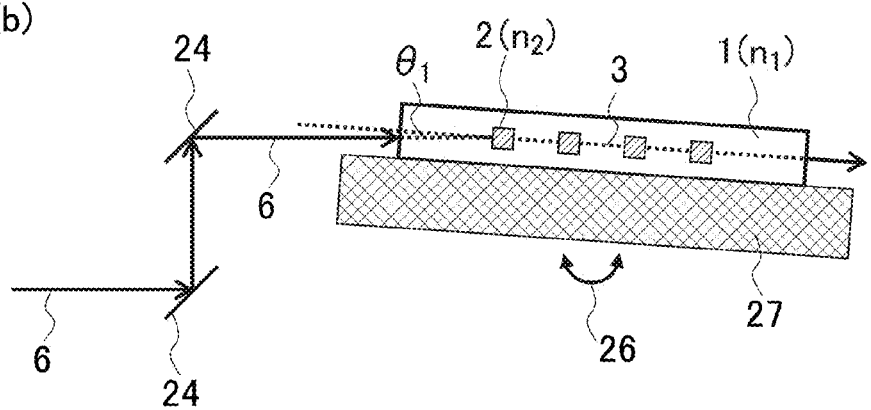

FIGS. 21(*a*) and 21(*b*) are schematic sectional views showing, in details, portions of the laser beam 6, the microchip 1, and the plural channels 2 shown in FIGS. 5(*a*) to 5(*c*), and is an explanatory view showing a mechanism for controlling an angle made by the laser beam and the beam side-entry axis. It is preferable that the microchip 1 and the analyzer are designed such that parameters prescribed as described above of the angle $\theta_1$ of the laser beam 6 irradiated to No. 1 channel 2 relative to the beam side-entry axis 3 and the like become desired values by only installing the microchip 1 on a stage 27 of the analyzer. However, it is assumed that $\theta_1$ or the like is deviated from a designed value by being caused by dispersion of a working accuracy of the microchip 1, a deformation by deterioration or the like, or a deformation by an environmental factor of the analyzer or the like. Hence, it is effective that the analyzer is provided with a calibration mechanism by which $\theta_1$ or the like can be made to be near a design value by an adjustment. FIG. 21(*a*) shows an example of a calibration mechanism, and an irradiation angle of the laser beam 6 to the microchip 1 is made to be a desired angle $\theta_1$ by controlling positions and angles of plural mirrors 24 by an adjusting mechanism 26. Or, as shown in FIG. 21(*b*), the desired angle $\theta_1$ is made to be able to be obtained by controlling the position and the angle of the stage 27 by the adjusting mechanism 26. Naturally, both of the adjusting mechanism of FIG. 21(*a*) and the adjusting mechanism of FIG. 21(*b*) may be used.

Figure 24:
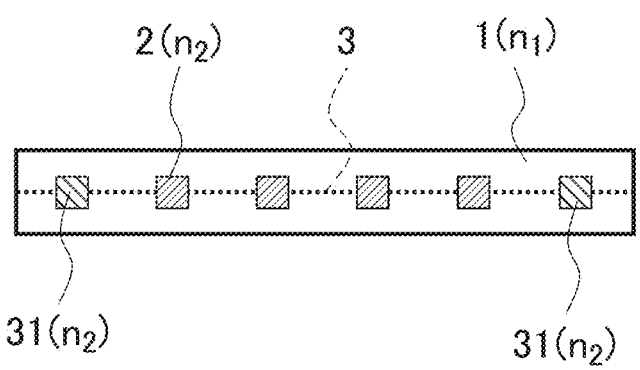
FIGS. 24(a) and 24(b) show schematic views of sections of microchips including markers for calibration.
Figure 24:
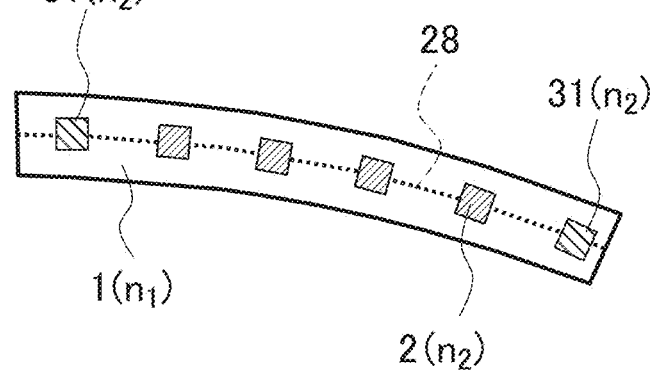

For example, it is effective to adjust a signal intensity to be near a design value by changing a relative angle between the laser beam 6 and the microchip 1 by the adjusting mechanism 26 of FIG. 21(*a*) or FIG. 21(*b*) while monitoring the signal intensity from each channel 2. As the signal intensity, it is convenient to utilize a Raman scattering intensity of water obtained from each channel 2. It is also effective to previously incorporate a marker for calibration other than the channel 2 which is used for analyzing a sample at an inner portion of the microchip 1. For example, as shown in FIG. 24(*a*), channels 31 for calibration are provided at both sides of the array of the channels 2 used for analysis. An inner portion of the channel 31 is filled with a medium of a refractive index $n_z$ which can obtain a comparatively strong Raman scattering. A pertinent relative angle is obtained by controlling the adjusting mechanism 26 of FIG. 21(*a*) or FIG. 21(*b*) while monitoring the Raman scattering intensity obtained from the channel 31. Further, emission from the channel 31 can be measured simultaneously with and independently from emission from the channel 2 by the fluorescence detection optical system shown in FIG. 5(*b*), and therefore, the adjusting mechanism 26 can be controlled in real time while carrying out an analysis. This is effective as a method of dealing with a case where the microchip is deformed by, for example, a temperature rise or the like in the midst of the analysis.

According to the present embodiment, in order to verify its effect, there was carried out a light ray trace simulation of the laser beam 6 which was made to be horizontally incident on the plural channels 2 provided at the microchip 1, a rate of an intensity of the laser beam 6 passing through the inner portion of each channel 2 relative to a total intensity of the laser beam 6 before being made to be horizontally incident, that is, an irradiation efficiency of the laser beam for each channel 2 was calculated, and it was evaluated to what degree of the channel number could be made to be irradiated by what degree of efficiency. It is verified that the laser beam irradiation efficiency of each channel 2 calculated from the light ray trace simulation excellently agrees with the fluorescence intensity rate of each channel 2 provided by an experiment as shown in a publicly-known literature, and it is an extremely reliable evaluation method. According to the present embodiment, as a three-dimensional light ray trace simulator, an illumination design analyzing software Lightlool™ (Synopsys' Optical Solutions Group) was used.

FIGS. 6(a) to 6(c), FIGS. 8(a) to 8(c), FIGS. 10(a) to 10(c), FIGS. 12(a) to 12(c), FIGS. 14(a) to 14(c), and FIGS. 16(a) to 16(c) show results of the light ray trace simulation. First, a content common to these diagrams will be explained. The diagrams show sections including the beam side-entry axis 3 and vertical to long axes of the respective channels 2. A wavelength of the laser beam 6 is 505 nm. (a), (b), and (c) in the respective diagrams respectively show results in a case where widths of the laser beam 6 incident on the microchip 1 in a direction vertical to the array plane and the beam side-entry axis 3 are b=5 µm, 50 µm, and 300 µm, respectively. In the microchip 1, a total of 24 channels 2 from No. 1 through No. 24 are arranged on the same plane. That is, L=24. Here, No. 1 shows the number of the channel 2 which is disposed at an end of a side of introducing the laser beam 6 and is irradiated first with the laser beam 6. Hereinafter, the respective channels 2 are attached with numbers of No. 2, No. 3, . . . , No. 24 in turn along an advancing direction of the laser beam 6. Each diagram is expressed by a yz plane comprising a y axis, and a z axis, and its origin is made to agree with a center of No. 1 channel, and the z axis is made to agree with the beam side-entry axis 3.

A surrounding of the microchip 1 is made to be air, that is, $n_0$=1.00. A member of the microchip 1 is ZEONOR™ (ZEONOR, Nippon Zeon). ZEONOR is a cycloolefin polymer (COP) resin, and is excellently used for a member of the microchip because of characteristics of high transparency, and low hygroscopic property. A refractive index of ZEONOR is $n_1$=1.53. A right upper side of each diagram describes conditions of a distance a between a position at which the center axis 5 of the laser beam 6 is incident on the side face of the microchip 1 and the beam side-entry axis 3, a width b of the laser beam 6 in a direction vertical to the array plane and the beam side-entry axis 3, an angle $\theta_1$ of the laser beam 6 irradiated to No. 1 channel relative to the beam side-entry axis, a refractive index $n_1$ of a member of the microchip 1, and a refractive index $n_2$ of a member filled in an inner portion of each channel 2. A sectional shape of each channel 2 was made to be isosceles trapezoidal shape. The isosceles trapezoidal shape was configured by a lower base of 50 µm a height of 50 µm, and a base angle of 92°, and an upper base is therefore made to be about 53.5 µm. That is, a draft angle in the injection molding is D=2°. The sectional shape of the channel 2 was made to be the isosceles trapezoidal shape, for improving a mass production property of the microchip 1 as described above. Although not illustrated in the respective diagrams, a face including the upper base of each isosceles trapezoidal shape is made to be the lamination surface 4. 24 channels 2 are arranged on the same plane at constant intervals p=300 µm. That is, a distance between a center of No. 1 channel and a center of No. 24 is 6.9 mm. b=5 µm is sufficiently smaller than d=50 µm which is a width of the channel 2, and therefore, the laser beam 6 can be regarded as a beam element of an infinitesimal width.

The laser beam 6 was configured by 300 beam elements having an infinitesimal width, and positions of the beam elements were arranged uniformly and at random at inner portions of respective diameters of (a), (b), and (c) of the respective diagrams. Further, a total intensity of the laser beam 6 before being incident on the microchip 1 is made to be 100%, the respective beam elements were equally and respectively provided with intensities of 1/300 (0.33%). In the light ray trace simulation, Snell's law and Fresnel's law were applied to positions at which a refractive index is changed, or an incidence face to the microchip 1, an incident face to each channel 2, and an outgoing face from each channel 2 or the like for each beam element and at each time, and advancing directions and intensity of refracted lights were tracked. However, in a case total reflection is occurred at positions at which the refractive index of the beam element is changed, advancing directions and intensity of refracted lights were tracked. The respective diagrams show optical paths of 300 beam elements calculated in this way.

Although the above-described light ray trace simulation was executed on three-dimensional models in the respective diagrams, the simulation results were indicated by two-dimensional images projected to planes vertical to the long axes of the respective channels 2 to be easy to see. Although the condition of b=5 µm at (a) of each diagram is not actually easy to realize, the condition was set to be easy to understand what behavior was shown by refraction of light rays of the beam elements by each channel 2. Next, beam elements transmitting an inner portion of each channel 2 were extracted for each channel 2 in 300 beam elements calculated in this way, and a total of the intensities of the beam elements at each channel 2 was calculated as the laser beam irradiation efficiency for each channel 2. FIGS. 7(a) to 7(c), FIGS. 9(a) to 9(c), FIGS. 11(a) to 11(c), FIGS. 13(a) to 13(c), FIGS. 15(a) to 15(c), and FIGS. 17(a) to 17(c) show calculation results of the laser beam irradiation efficiency of the respective channels 2 for (a), (b), and (c) in FIGS. 6(a) to 6(c), FIGS. 8(a) to 8(c), FIGS. 10(a) to 10(c), FIGS. 12(a) to 12(c), FIGS. 14(a) to 14(c), and FIGS. 16(a) to 16(c), respectively. The calculation results are results of calculations on the three-dimensional model.

FIG. 6(a), 6(b), or 6(c) respectively show a diagram showing a result of the light ray trace simulation in a case of irradiating the laser beam 6 from a side face of the microchip 1 by aligning with the beam side-entry axis 3 in accordance with FIG. 1(b). That is, a distance between a position at which the center axis 5 of the laser beam 6 is incident on the side face of the microchip 1 and the beam side-entry axis 3 is a=0 µm, and an angle of the laser beam 6 irradiated to No. 1 channel 2 relative to the beam side-entry axis 3 is $\theta_1$=0°. That is, Equation (16) is not satisfied. According to the present embodiment, a buffer solution was filled at an inner portion of each channel 2. A refractive index of the aqueous solution is not different from that of pure water, and $n_2$=1.33. At this time, a refraction angle of the laser beam 6 by the channel 2 is calculated as $\epsilon_2$=−0.52° by Equation (7).

In the condition of b=5 µm of FIG. 6(a), $\epsilon_2$=−0.52° (<0°), and therefore, the laser beam 6 is refracted from the beam side-entry axis 3 to a lower direction, and is completely deviated at the channel 2 of No. 5 and thereafter. As a result, as shown in FIG. 7(a), although the laser beam irradiation efficiencies of No. 1, through No. 4 channels 2 are as high as 90% or more, the laser beam irradiation efficiency becomes 0 in the channels 2 at No. 5 and thereafter. A condition of b=50 µm of FIG. 6(b) shows a case where diameters of the laser beam 6 and the channel 2 are made to be equal, and this is a typical example of a case of narrowing the laser beam 6 to be incident horizontally. The result of FIG. 7(b) dulls a change of the laser beam irradiation efficiency of FIG. 7(a). Although the laser beam irradiation efficiency of FIG. 7(b) was equivalent to that of FIG. 7(a) at No. 1, channel 2, the laser beam irradiation efficiency was monotonously reduced at the channels 2 of No. 2 and thereafter, and became zero at the channels 2 of No. 7 and thereafter. A condition of b=300 μm of FIG. 6(c) shows a typical example of a case where the laser beam 6 is enlarged more than the diameter of the channel 2 to be horizontally incident. A large number of the beam elements did not contribute to irradiation at all of the channels 2 and in turn, an effective laser beam intensity was reduced by just as much, and therefore, the laser beam irradiation efficiency of FIG. 7(c) was reduced a degree of one fifth of a case of FIG. 7(b) in all the channels 2, and became zero at the channel 2 of No. 7 and thereafter. In FIG. 6(c), there is a behavior in which the beam elements incident on No. 1 channel 2 are deviated from the array of the channel 2 by refraction similar to FIG. 6(b), and the other beam elements advance straight since the beam elements are not refracted. However, the straight advancing beam elements do not contribute to irradiation of the channel 2 at all, and therefore, the laser beam irradiation efficiency is reduced as shown in FIG. 7(c).

In FIGS. 8(a) to 8(c) and FIGS. 9(a) to 9(c), each result of the light ray trace simulation is shown in a case where the laser beam 6 is irradiated from the side face of the microchip 1 by inclining the laser beam 6 by $\theta_1=4°$ (>0°) to the beam side-entry axis 3 in accordance with FIG. 1(c). At this time, Equation (16) is satisfied. Further, the condition of satisfying Equation (17) is $\theta_1>0.52°$, and also Equation (17) is satisfied. Further, a condition of satisfying Equation (9) is $\theta_1<10.0°$, and Equation (9) is also satisfied. On the other hand, the condition of satisfying Equation (15) is $\theta_1<3.46°$, and Equation (15) is not satisfied. Concerning FIGS. 8(a), 8(b), and 8(c), positions at which the center axis 5 of the laser beam 6 is incident on the side face of the microchip 1 are positions at which the center axis 5 is remote from the beam side-entry axis 3 to a lower side from the beam side-entry axis 3, that is, in a direction of being remote from the lamination surface 4, by distances of a=60 μm, 60 μm, and 180 μm, respectively. Thereby, the center axis 5 of the laser beam 6 irradiates substantially a center of No. 1 channel 2 concerning FIG. 8(a) and FIG. 8(b), and a vicinity of an upper end of the laser beam 6 irradiates No. 1 channel 2 concerning FIG. 8(c). The other condition, its display method and the like of FIGS. 8(a) to 8(c) and FIGS. 9(a) to 9(c) are similar to those of FIGS. 6(a) to 6(c) and FIGS. 7(a) to 7(c).

Figure 7:
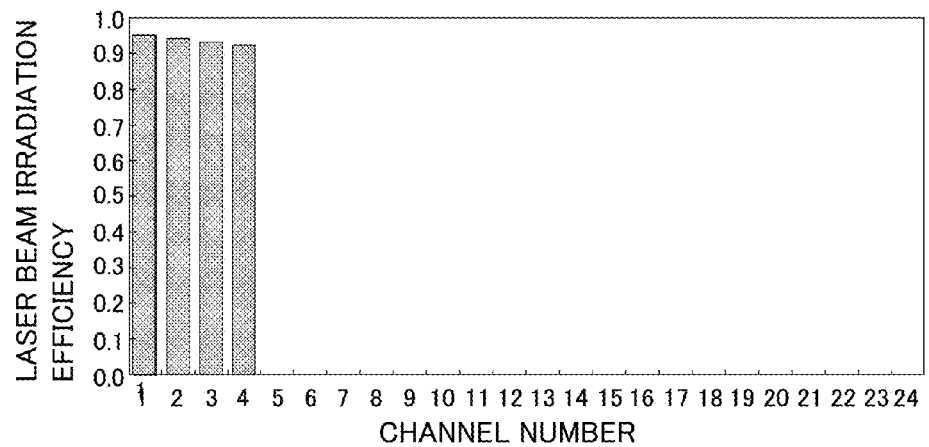
FIGS. 7(a) to 7(c) show diagrams indicating calculation results of irradiation efficiency of side-entry laser beams in microchips where $\theta_1=0°$, $n_2=1.33$, 24 channels.
Figure 7:
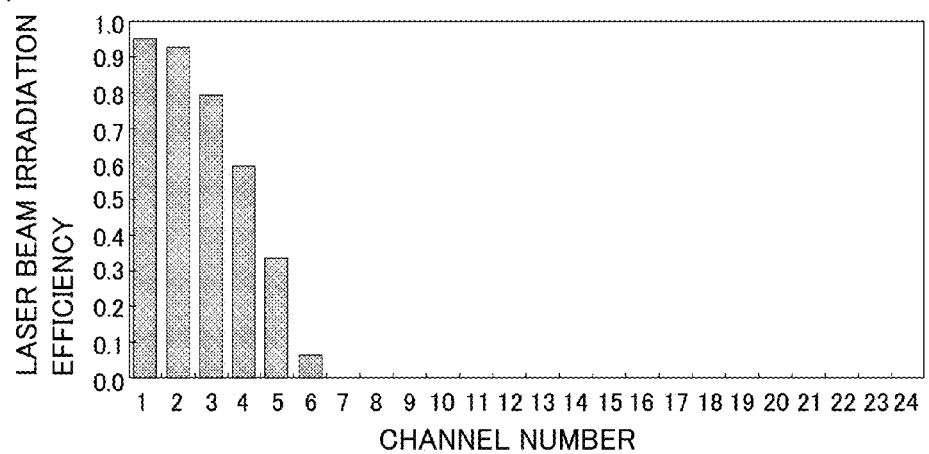
Figure 7:
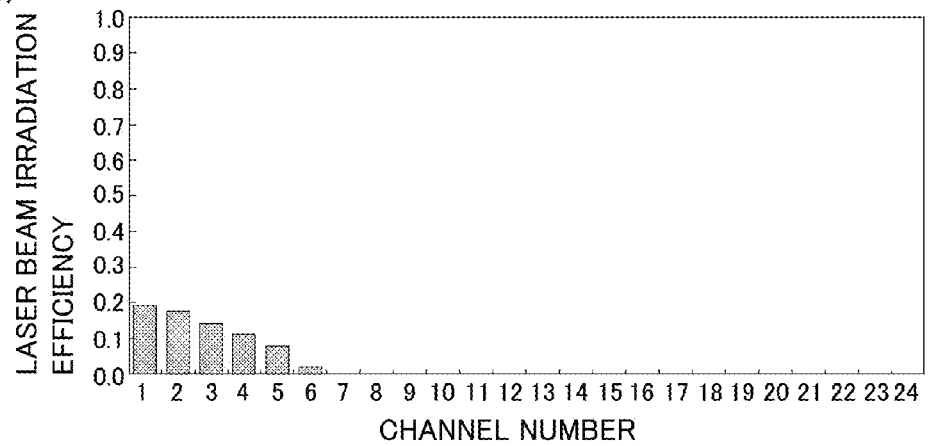
Figure 8A:
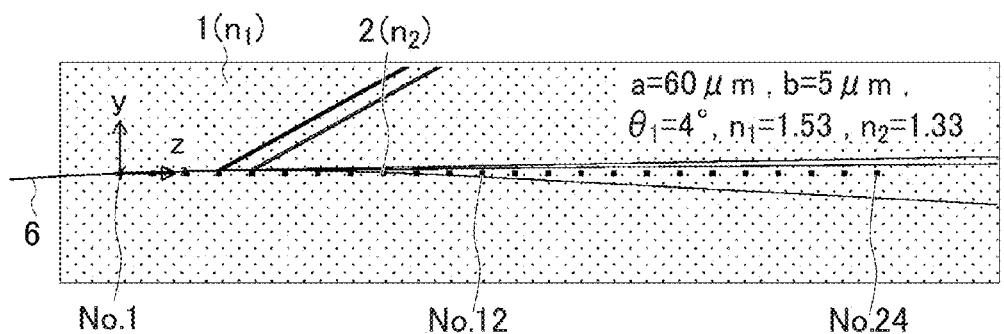
FIGS. 8(a) to 8(c) show diagrams indicating light ray trace simulation results of side-entry laser beams in microchips where $\theta_1=4°$, $n_2=1.33$, 24 channels.
Figure 8B:
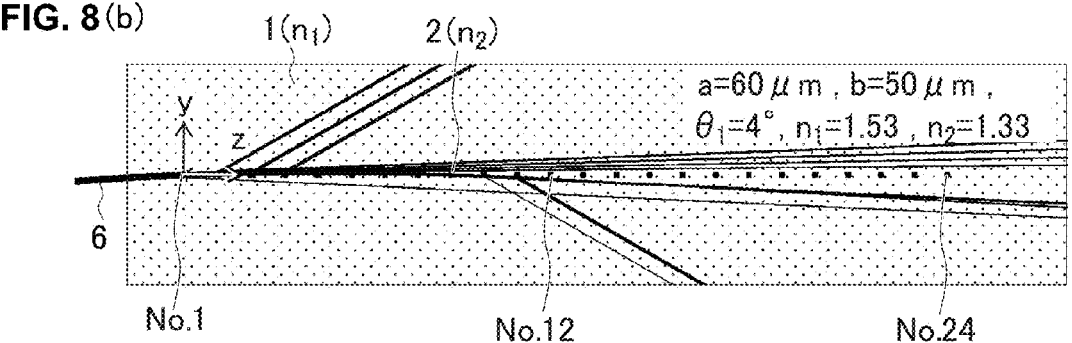
Figure 8C:
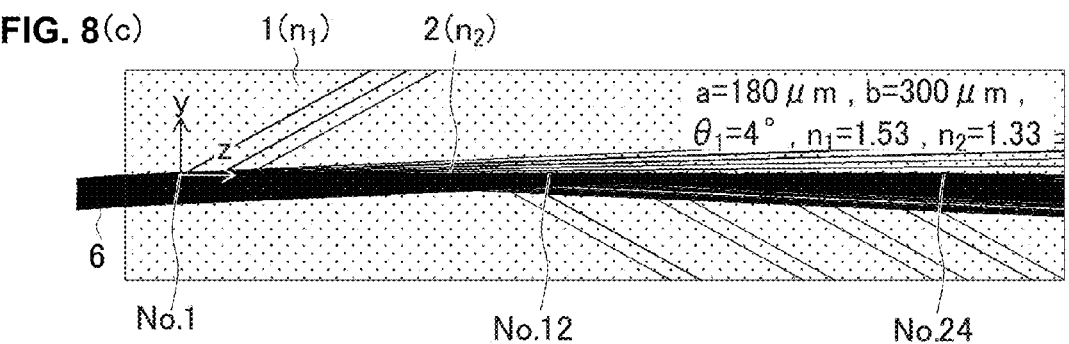
Figure 9:
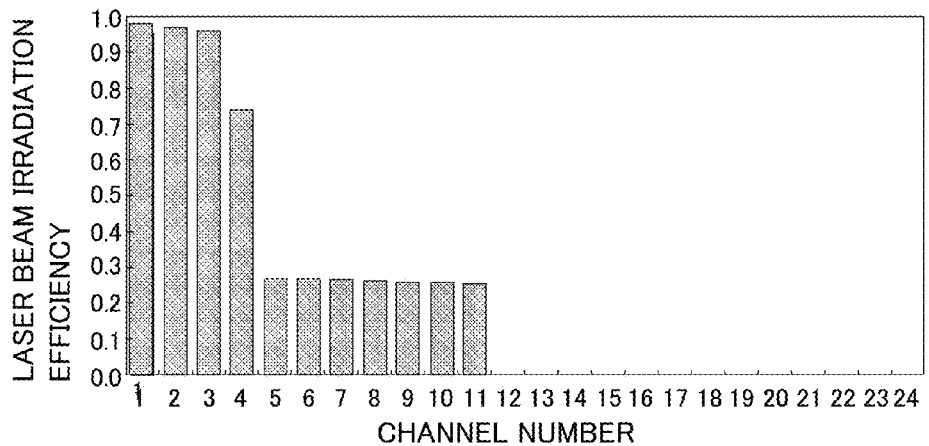
FIGS. 9(a) to 9(c) show diagrams indicating calculation results of irradiation efficiency of side-entry laser beams in microchips where $\theta_1=4°$, $n_2=1.33$, 24 channels.
Figure 9:
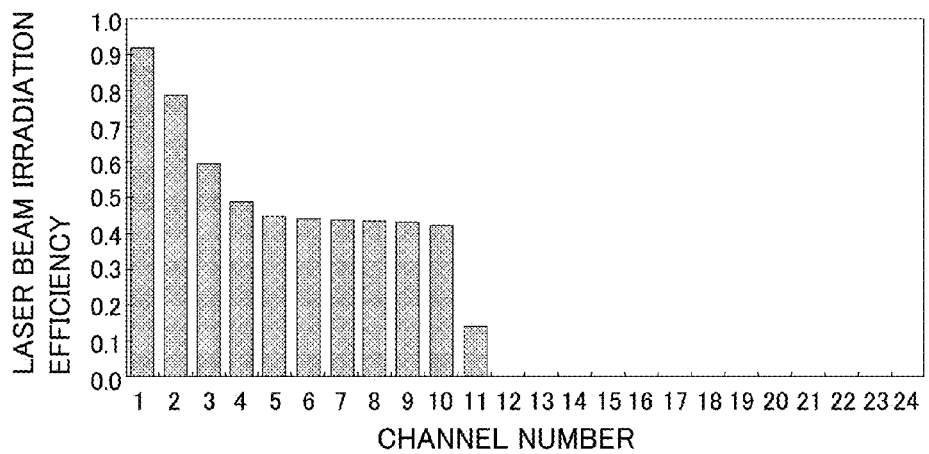
Figure 9:
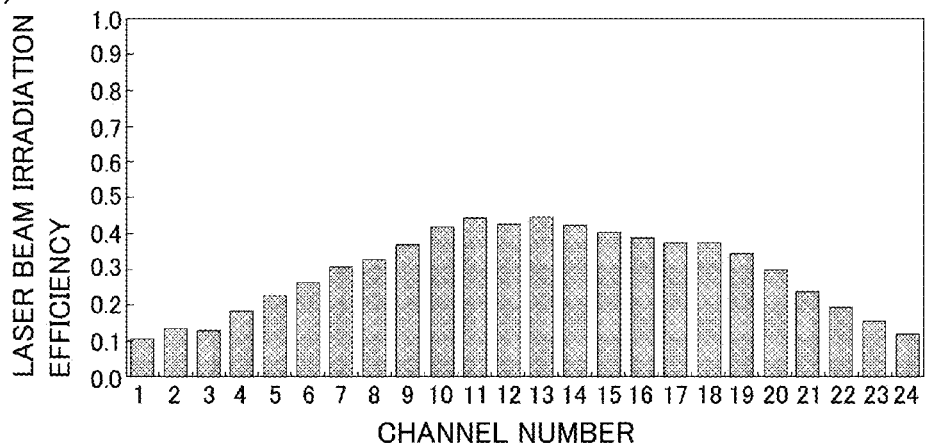
Figure 10:
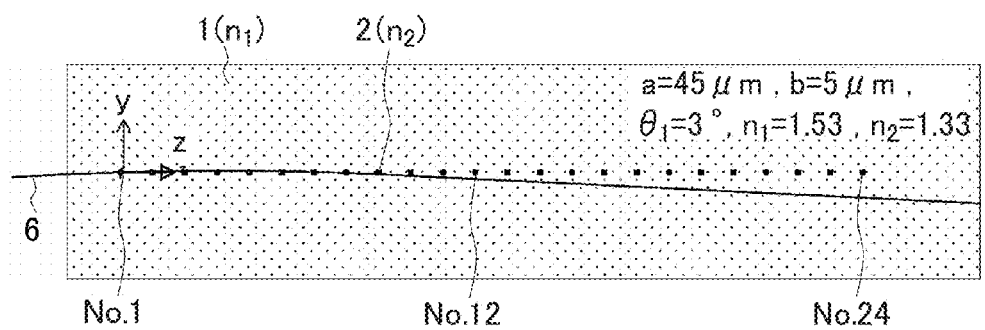
FIGS. 10(a) to 10(c) show diagrams indicating light ray trace simulation results of side-entry laser beams in microchips where $\theta_1=3°$, $n_2=1.33$, 24 channels.
Figure 10:
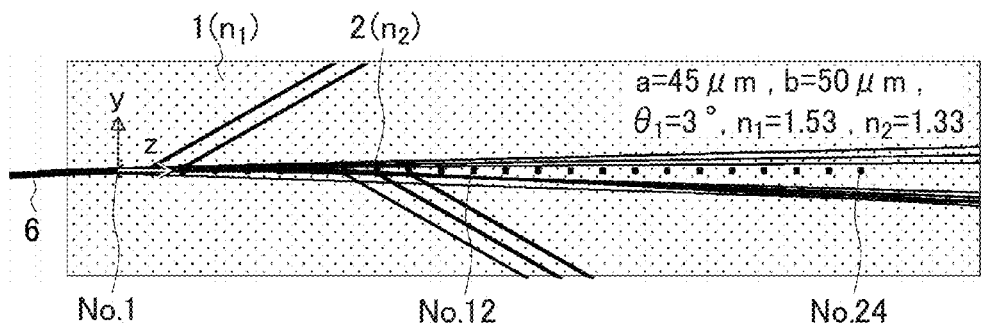
Figure 10:
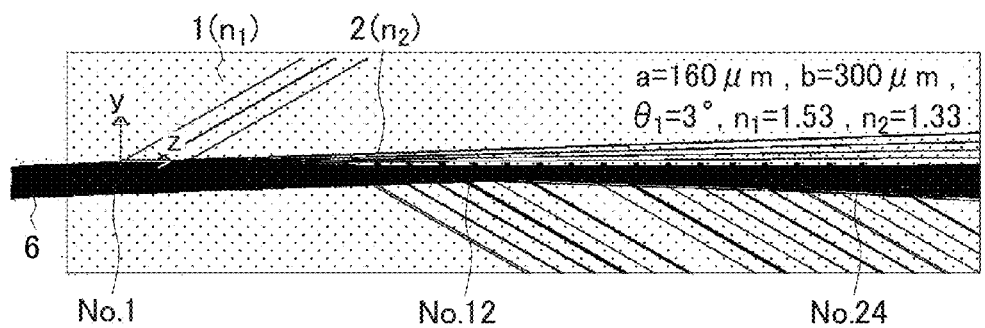

FIG. 8(a) shows that as a result of increasing a distance of the laser beam in the microchip in a direction of the beam side-entry axis 3 until the laser beam 6 is deviated from the array of the channels 2, the configuration of FIG. 8(a) contributes to irradiate the more channels 2 in comparison with the configuration of FIG. 6(a). As shown in FIG. 9(a), 11 channels 2 of Nos. 1 through 11 can be irradiated, and in comparison with 4 channels 2 in FIG. 7(a), the number of channels which can simultaneously be irradiated is significantly increased. However, an average value of the laser beam irradiation efficiency is reduced, and dispersion thereof is increased. FIG. 8(b) and FIG. 9(b) show that in comparison with FIG. 6(b) and FIG. 7(b), the number of the channels which can simultaneously be irradiated is increased from 6 to 11 by the similar effect. Particularly high effect is shown by a point that the number of channels which can acquire the laser bean irradiation efficiency of 30% or more is increased from 5 to 10. In FIG. 8(c) and FIG. 9(c), in addition to a similar reason, the number of the channels 2 which are irradiated by any beam element first is increased by configuring b=300 μm and $\theta_1=4°$, and therefore, in comparison with FIG. 6(c) and FIG. 7(c), FIG. 8(c) and FIG. 9(c) show that the number of the channels which can simultaneously be irradiated is increased from 6 to 24. A particularly high effect is that the number of the channels which can achieve the laser beam irradiation efficiency of 30% or more is increased from 0 to 13. Here, when $\theta_1=4°$, M=8 by Equation (14), a condition of satisfying Equation (20) becomes b >168 μm, and Equation (20) is satisfied. On the other hand, a condition of satisfying Equation (19) becomes b >482 μm, and Equation (19) is not satisfied.

In FIGS. 10(a) to 10(c) and FIGS. 11(a) to 11(c), each result of the light ray trace simulation is shown in a case where the laser beam 6 is irradiated from the side face of the microchip 1 by being inclined by $\theta_1=3°$ (>0°) to the beam side-entry axis 3 in accordance with FIG. 1(c). At this time, $\theta_1<3.46°$ of Equation (15), in addition thereto, $\theta_1>0.0°$ 0° of Equation (16), $\theta 0_1>0.52°$ of Equation (17), and $\theta_1<10.0°$ 0° of Equation (9) are all satisfied. Thereby, in comparison with the case of FIGS. 8(a) to 8(c) and FIGS. 9(a) to 9(c), a more efficient laser beam irradiation can be realized. Concerning FIGS. 10(a), 10(b), and 10(c), positions at which the center axis 5 of the laser beam 6 is incident on the side face of the microchip 1 are positions at which the distance is remote by the distance of a=45 μm, 45 μm, and 160 μm, respectively, to a lower side of the beam side-entry axis 3, that is, in a direction of being remote from the lamination surface 4. Thereby, concerning FIG. 10(a) and FIG. 10(b), the center axis 5 of the laser beam 6 was made to irradiate substantially a center of No. 1 channel 2, and concerning FIG. 10(c), a vicinity of an upper end of the laser beam 6 irradiated No. 1 channel 2. The other condition, displaying method and the like of FIGS. 10(a) to 10(c) and FIGS. 11(a) to 11(c) are similar to those in the case of FIGS. 8(a) to 8(c) and FIGS. 9(a) to 9(c).

Figure 11A:
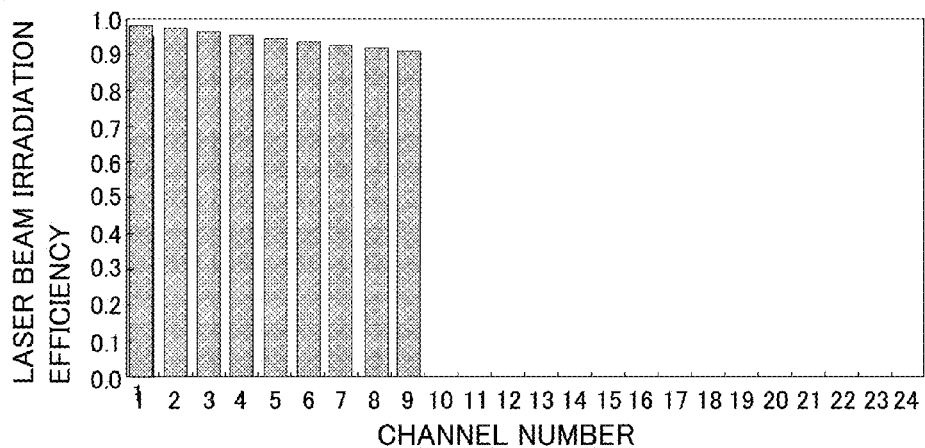
FIGS. 11(a) to 11(c) show diagrams indicating calculation results of irradiation efficiency of side-entry laser beams in microchips where $\theta_1=3°$, $n_2=1.33$, 24 channels.
Figure 11B:
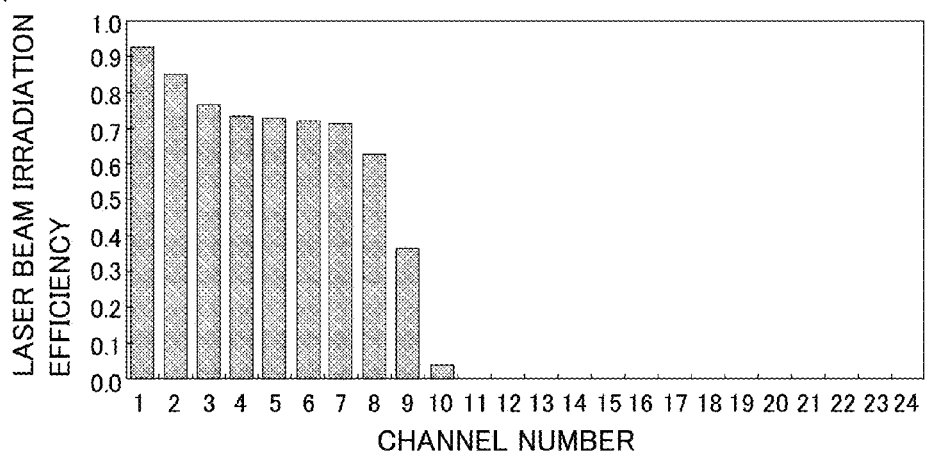
Figure 11C:
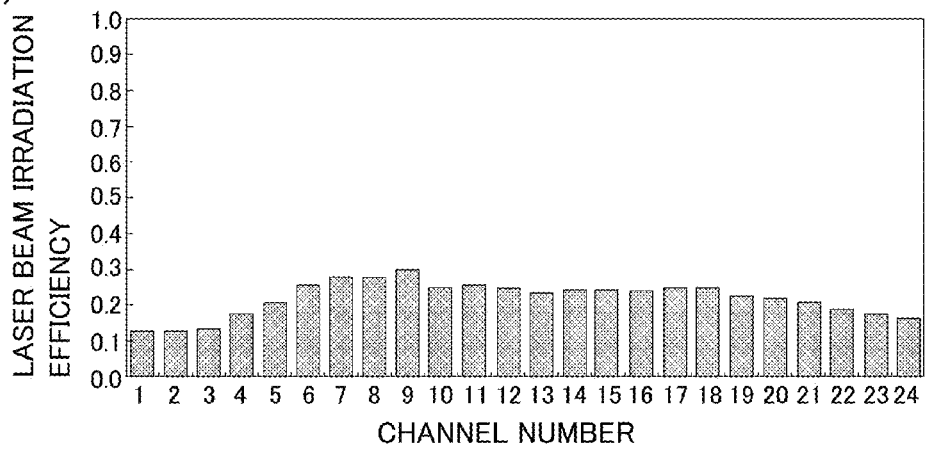

In FIG. 10(a) and FIG. 11(a), in comparison with FIG. 8(a) and FIG. 9(a), a condition of being further suitable for beam side-entry is configured by satisfying also Equation (15), and although the number of channels which can simultaneously be irradiated is reduced from 11 to 9, an average value of the laser beam irradiation efficiencies is significantly improved and at the same time, the dispersion is significantly reduced. In FIG. 10(b) and FIG. 11(b), by a similar effect, in comparison with FIG. 8(b) and FIG. 9(b), the number of channels achieving the laser beam irradiation efficiency of 70% or more is increased from 2 to 7. This is important performance in executing a highly sensitive analysis by a number of channels. FIG. 10(c) and FIG. 11(c) show that in comparison with FIG. 8(c) and FIG. 9(c), although an average value of the laser beam irradiation efficiencies concerning 24 channels 2 is reduced from 29% to 22%, an effect of reducing a CV value indicating dispersion thereof from 40% to 22% is achieved. This is important performance in executing a stable analysis by a number of channels. Here, when $\theta_1=3°$, M=6 by Equation (14), a condition of satisfying Equation (20) becomes b>189 μm, and Equation (20) is satisfied. On the other hand, a condition of satisfying Equation (19) becomes b>362 μm, and Equation (19) is not satisfied.

According to the present embodiment, it was shown that by irradiating the laser beam to the side face of the microchip by inclining the laser beam by $\theta_1>0$ to the beam side-entry axis 3 by using a microchip provided with plural channels sections of which vertical to long axes were configured by an isosceles trapezoidal shape, more channels than channels irradiated by $\theta_1=0°$ could effectively be irradiated, and the configuration could contribute to increase an efficiency of analysis and improve a throughput. Although according to the present embodiment, the description has been given by taking an example of the channel a sectional shape vertical to a long axis of which is configured by an isosceles trapezoidal shape, a similar effect can be achieved naturally in a trapezoidal shape which is not isosceles, and even when a section is configured by a triangular shape, or respective sides are not linear lines but in a circular arc shape, or even when a corner of a trapezoidal shape or a triangular shape is rounded. Generally, a similar effect can be achieved for a microchip provided with plural channels having a section vertical to a long axis in a tapered shape.

Here, consider a case of introducing the laser beam 6 from a lower face of the microchip 1. By Equation (18), an angle of the laser beam 6 irradiated to No. 1 channel 2 relative to the beam side-entry axis 3 becomes $\theta_1 > 50°$ for a $\theta_0$. Therefore, both of $\theta_1 < 10.0°$ of Equation (9) and $\theta_1 < 3.46°$ of Equation (15) cannot be satisfied, and the efficient beam side-entry system cannot be realized. Therefore, according to the present embodiment, it is a necessary configuration that the laser beam 6 is not introduced from an upper face or a lower face of the microchip 1, but is introduced from the side face of the microchip 1.

[Second Embodiment]

According to the present embodiment, a description will be given centering on a difference from the first embodiment, and in a case where a description is not particularly given, it may be considered that a description similar to that of the first embodiment is established. According to the present embodiment, a member filled in an inner portion of each channel 2 was changed from a buffer solution to 3500/3500×L POP-7™ polymer solution (Life Technologies). POP-7 is an aqueous solution including 8 M urea and a polymer which becomes an electrophoresis separation medium, and is used in DNA sequencing. A refractive index of the solution is $n_2=1.41$ by an influence of 8 M of urea. At this time, the refraction angle of the laser beam 6 by the channel 2 is calculated as $\epsilon_2=-0.31°$ by Equation (7).

FIGS. 12(a) to 12(c) and FIGS. 13(a) to 13(c) are diagrams showing each result of the light ray trace simulation in a case where the laser beam 6 is irradiated by aligning with the beam side-entry axis 3 from the side face of the microchip 1 in accordance with FIG. 1(b), similarly to FIGS. 6(a) to 6(c) and FIGS. 7(a) to 7(c). That is, a distance between a position at which the center axis 5 of the laser beam 6 on the side face of the microchip 1 and the beam side-entry axis 3 is $a=0$ μm, and an angle of the laser beam 6 irradiated to No. 1 channel relative the beam side-entry axis 3 is $\theta_1=0°$. That is, Equation (16) is not satisfied.

Figure 6:
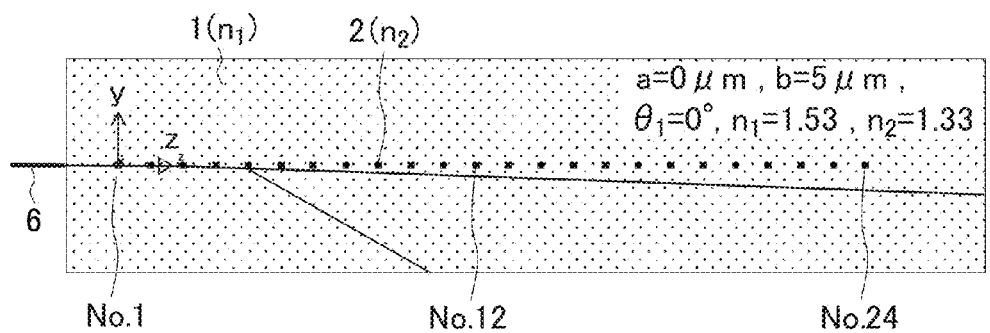
FIGS. 6(a) to 6(c) show diagrams indicating light ray trace simulation results of side-entry laser beams in microchips where $\theta_1=0°$, $n_2=1.33$, 24 channels.
Figure 6:
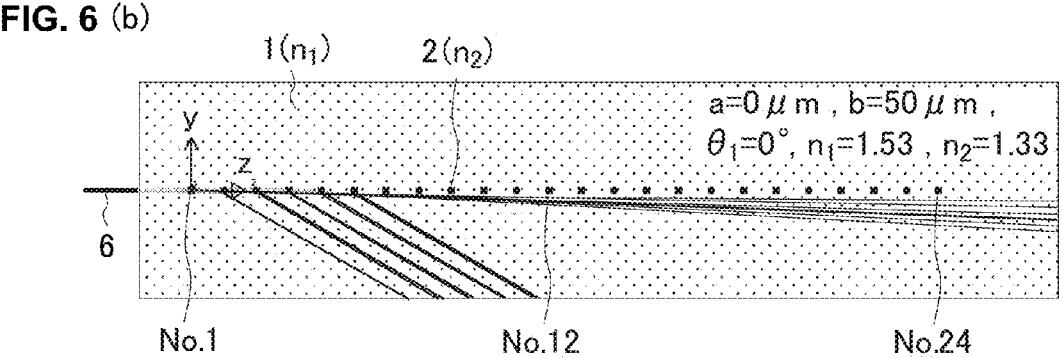
Figure 6:
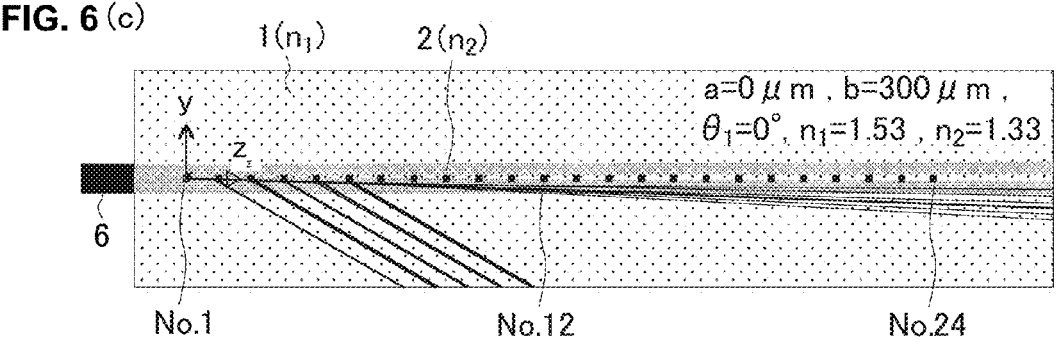
Figure 12:
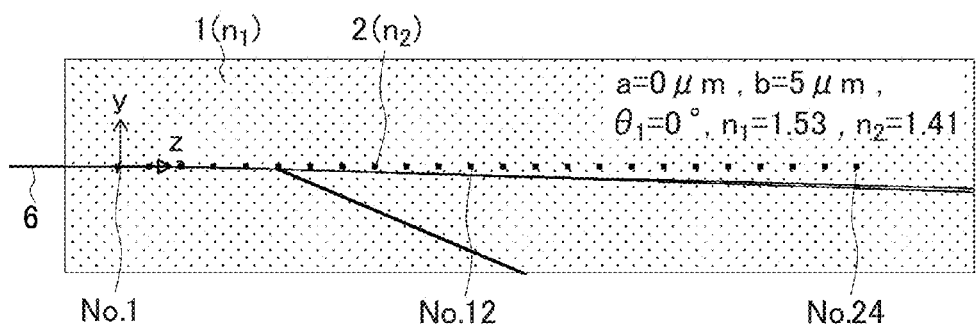
FIGS. 12(a) to 12(c) show diagrams indicating light ray trace simulation results of side-entry laser beams in microchips where $\theta_1=0°$, $n_2=1.41$, 24 channels.
Figure 12:
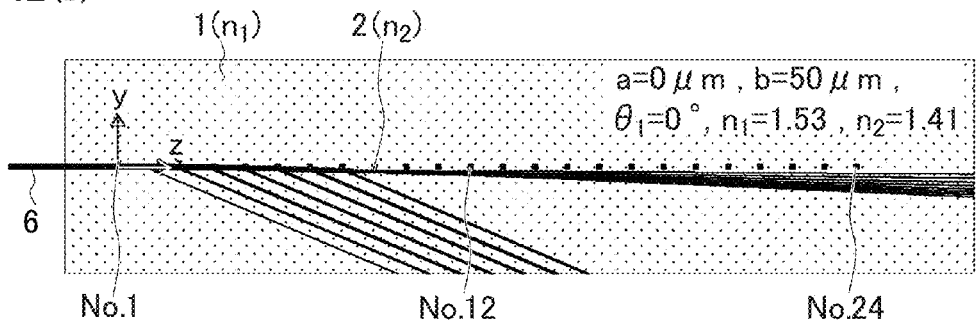
Figure 12:
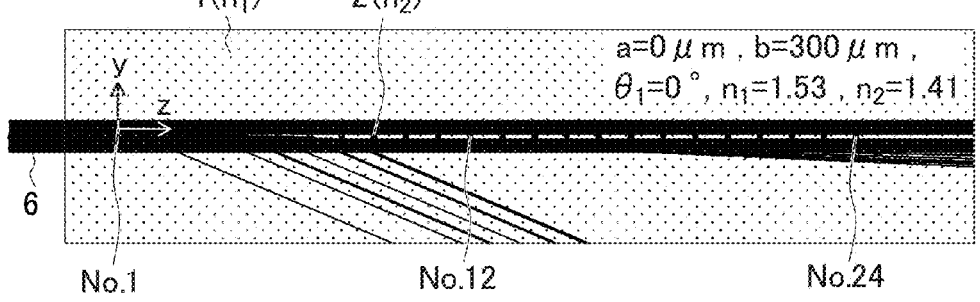
Figure 13A:
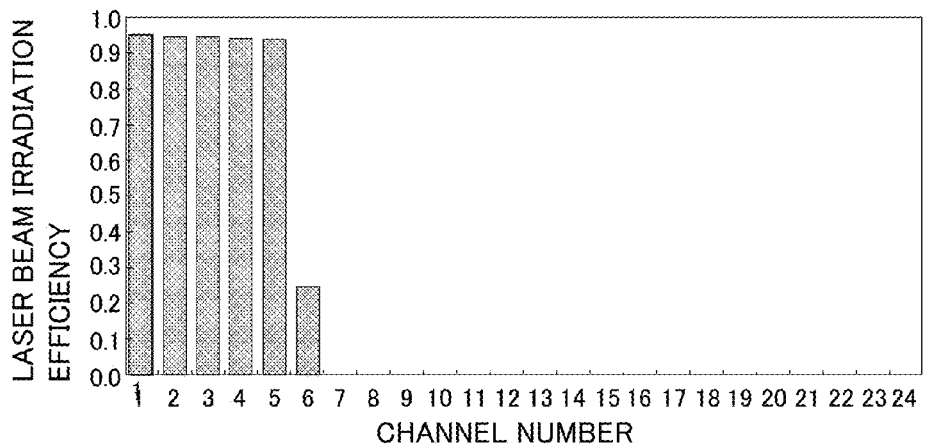
FIGS. 13(a) to 13(c) show diagrams indicating calculation results of irradiation efficiency of side-entry laser beams in microchips where $\theta_1=0°$, $n_2=1.41$, 24 channels.
Figure 13B:
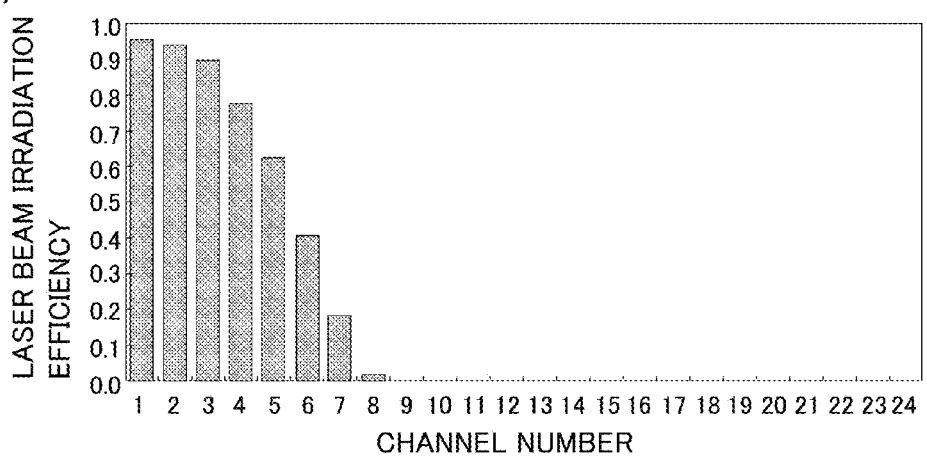
Figure 13C:
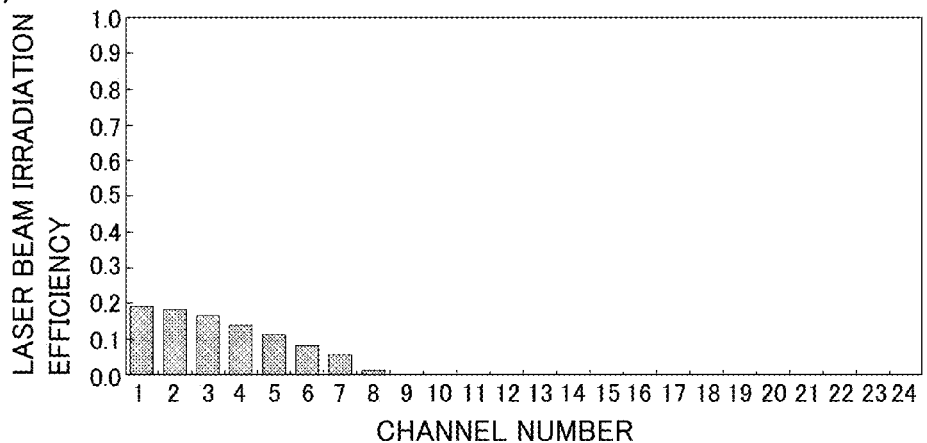

According to a condition of configuring $b=5$ μm of FIG. 12(a), a magnitude of $\epsilon_2$ was smaller than that in FIG. 6(a), or the refraction of the laser beam 6 by the channel 2 was reduced, and therefore, the laser beam 6 was rather gradually deviated from the array of the channel 2. As a result, as shown in FIG. 13(a), the number of channels which can be irradiated simultaneously is slightly increased from 4 of FIGS. 7(a) to 6. According to a condition of configuring $b=50$ μm of FIG. 12(b), similar to the case of FIG. 6(b), in comparison with FIG. 12(a), a change of the laser beam irradiation efficiency is dulled. According to the laser beam irradiation efficiency of FIG. 13(b), although the efficiency was equivalent to that of FIG. 7(a) at No. 1 channel 2, the efficiency was monotonously reduced at the channels 2 at No. 2 and thereafter, and the efficiency became zero at the channel 2 at No. 9 and thereafter. Similarly to FIG. 13(a), the number of channels which can simultaneously be irradiated is slightly increased. Even in a condition of configuring $b=300$ μm of FIG. 12(c), a similar tendency was observed. The laser beam irradiation efficiency of FIG. 13(c) was reduced to about one fifth of that in the case of FIG. 12(b) in all of the channels 2, and became zero at the channel 2 at No. 9 and thereafter.

FIGS. 14(a) to 14(c) and FIGS. 15(a) to 15(c) show each result of the light ray trace simulation in a case where the laser beam 6 is irradiated from the side of the microchip 1 by being inclined by $\theta_1=3°$ (>0°) to the beam side-entry axis 3 in accordance with FIG. 1(c). At this time, Equation (16) is satisfied. Further, a condition of satisfying Equation (17) is $\theta > 0.31°$, and also Equation (17) is satisfied. Further, a condition of satisfying Equation (9) is $\theta_1 < 9.74°$, and Equation (9) is also satisfied. On the other hand, a condition of satisfying Equation (15) is $\theta_1 < 2.68°$, and Equation (15) is not satisfied. Concerning FIGS. 14(a), 14(b), and 14(c), a position at which the center axis 5 of the laser beam 6 is incident on the side face of the microchip 1 is a position on a lower side of the beam side-entry axis 3, that is, in a direction of being remote from the lamination surface by distances of $a=45$ μm, 45 μm, and 160 μm, respectively. Thereby, concerning FIG. 14(a) and FIG. 14(b), the center axis of the laser beam 6 was made to irradiate substantially a center of No. 1 channel 2, and concerning FIG. 14(c), a vicinity of an upper end of the laser beam 6 was made to irradiate No. 1 channel 2. The other condition, displaying method, and the like of FIGS. 14(a) to 14(c) and FIGS. 15(a) to 15(c) are similar to those of FIGS. 12(a) to 12(c) and FIGS. 13(a) to 13(c).

Figure 14:
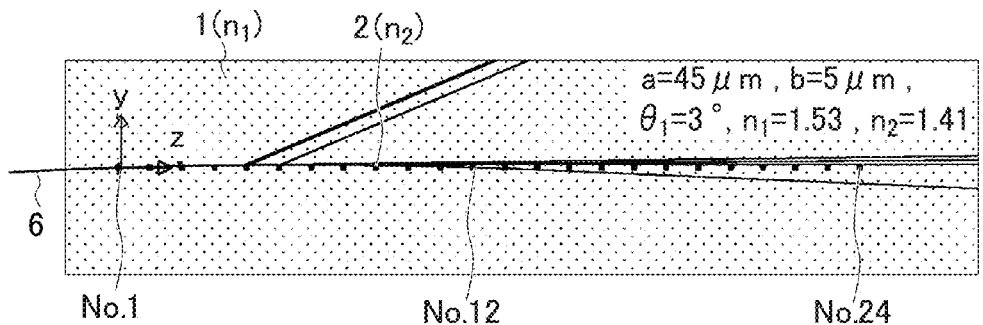
FIGS. 14(a) to 14(c) show diagrams indicating light ray trace simulation results of side-entry laser beams in microchips where $\theta_1=3°$, $n_2=1.41$, 24 channels.
Figure 14:
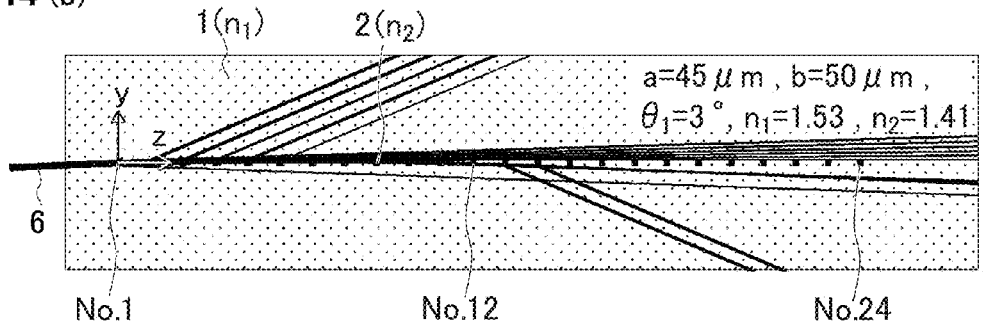
Figure 14:
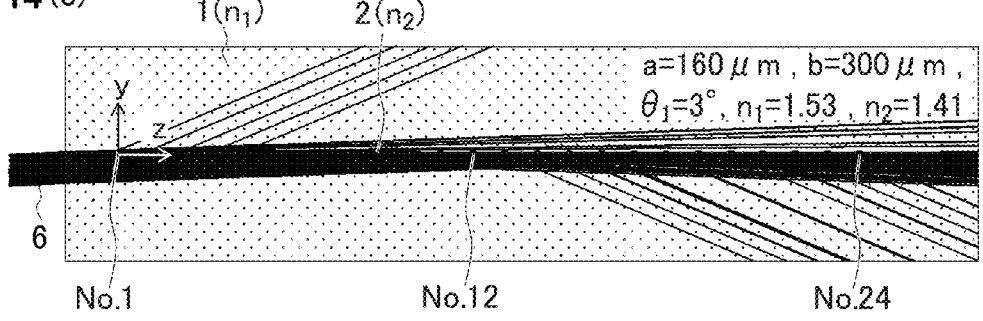
Figure 15:
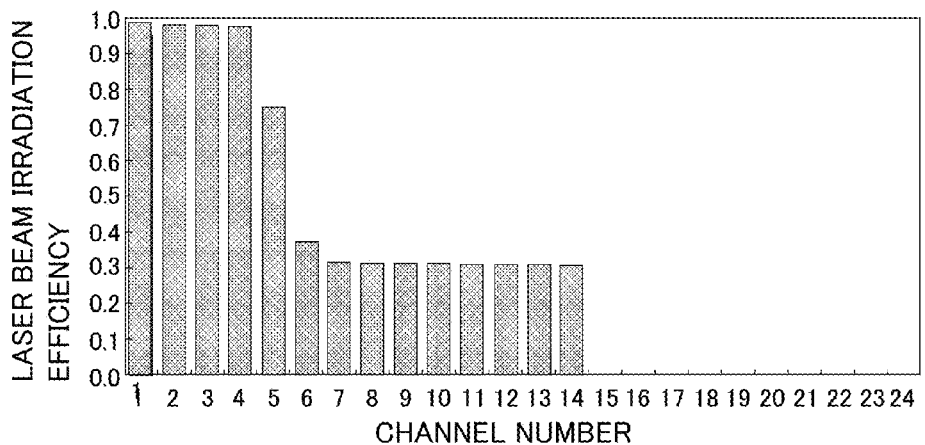
FIGS. 15(a) to 15(c) show diagrams indicating calculation results of irradiation efficiency of side-entry laser beams in microchips where $\theta_1=3°$, $n_2=1.41$, 24 channels.
Figure 15:
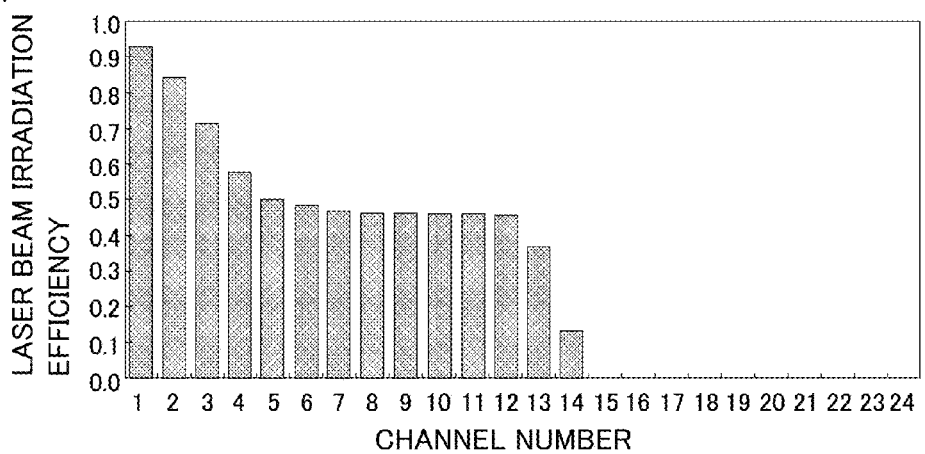
Figure 15:
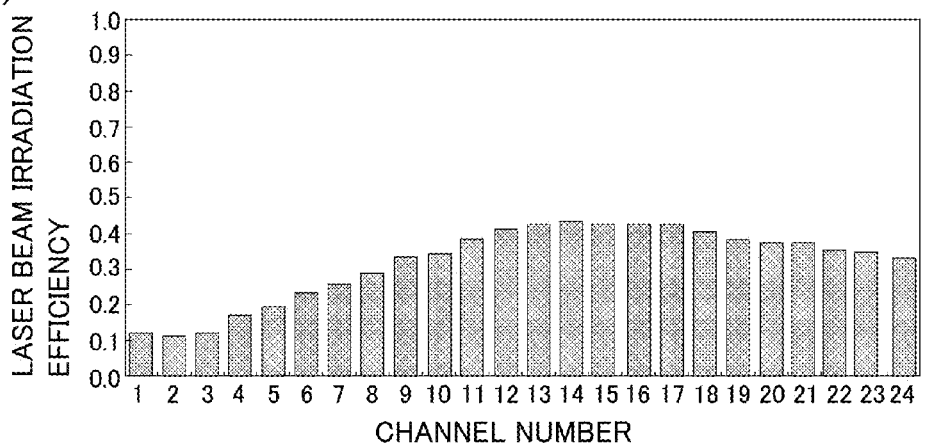

FIG. 14(a) shows that as a result of increasing a distance of the laser beam in the microchip in a direction of the beam side-entry axis 3 until the laser beam 6 is deviated from the array of the channels 2, the configuration of FIG. 14(a) contributes to irradiate the channels 2 more than those of FIG. 12(a). As shown in FIG. 15(a), 14 channels 2 of No. 1, through 14 can be irradiated, and in comparison with 6 channels of FIG. 13(a), the number of the channels which can simultaneously be irradiated is increased significantly. However, an average value of the laser beam irradiation efficiencies is reduced, and dispersion thereof is increased. FIG. 14(b) and FIG. 15(b) shows that in comparison with FIG. 12(b) and FIG. 13(b), the number of the channels which can simultaneously be irradiated is increased from 8 to 14. A particularly high effect is a point that the number of the channels which can obtain the laser beam irradiation efficiency of 30% or more is increased from 6 to 13. FIG. 14(c) and FIG. 15(c) show that in addition to a similar reason, the number of the channels 2 which are irradiated by any element first is increased by configuring $b=300$ μm and $\theta_1=3°$, and therefore, in comparison with FIG. 12(c) and FIG. 13(c), the number of the channels which can simultaneously be irradiated is increased from 8 to 24. A particularly high effect is a point that the number of channels which can achieve the laser beam irradiation efficiencies of 30% or more is increased from zero to 16. Here, when $\theta_1=3°$, $M=10$ by Equation (14), a condition of satisfying Equation (20) is $b>63$ μm, and Equation (20) is satisfied. On the other hand, a condition of satisfying Equation (19) is $b>362$ μm, and Equation (19) is not satisfied.

FIGS. 16(a) to 16(c) and FIGS. 17(a) to 17(c) show each result of the light ray trace simulation in a case where the laser beam 6 is irradiated from the side face of the microchip 1 by being inclined by $\theta_1=2°$ (>0°) to the beam side-entry axis 3 in accordance with FIG. 1(c). At this time, $\theta_1 > 0.0°$ of Equation (16), $\theta_1 > 0.31°$ of Equation (17), $\theta_1 < 9.74°$ of Equation (9), in addition thereto, $\theta_1 < 2.68°$ of Equation (15) are all satisfied. Thereby, in comparison with a case of FIG. 14 and FIG. 15, further efficient laser beam irradiation can be realized. Concerning FIGS. 16(a), 16(b), and 16(c), a position at which the center axis 5 of the laser beam 6 is incident on the side face of the microchip 1 is a position on a lower side of the beam side-entry axis 3, that is, at which the center axis 5 is remote from the beam side-entry axis 3 by distances of 30 µm, 30 µm, and 150 µm, respectively, in a direction of being remote from the lamination surface. Thereby, concerning FIG. 16(a) and FIG. 16(b), the center axis 5 of the laser beam 6 was made to irradiate substantially a center of No. 1 channel 2, concerning FIG. 16(c), a vicinity of an upper end of the laser beam 6 irradiated No. 1 channel 2. The other condition, the displaying method and the like of FIGS. 10 (a) to 10 (c) and FIGS. 11 (a) to 11(c) are similar to those in the case of FIGS. 14(a) to 14(c) and FIGS. 15(a) to 15(c).

Figure 16:
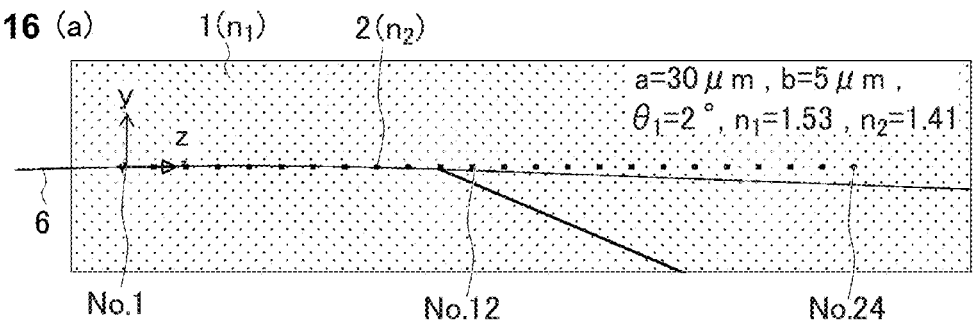
FIGS. 16(a) to 16(c) show diagrams indicating light ray trace simulation results of side-entry laser beams in microchips where $\theta_1=2°$, $n_2=1.41$, 24 channels.
Figure 16:
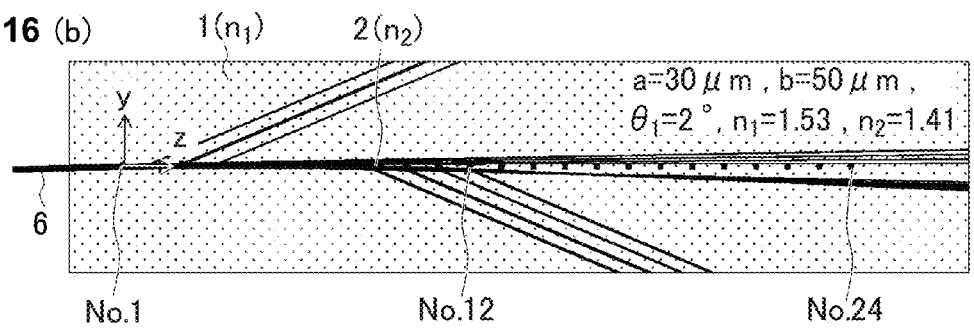
Figure 16:
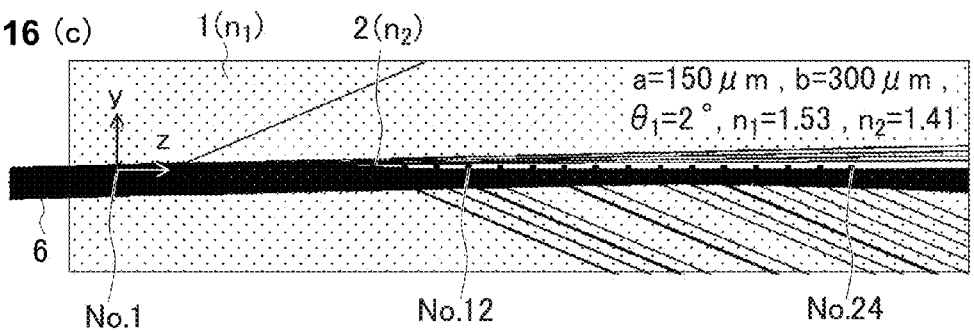
Figure 17A:
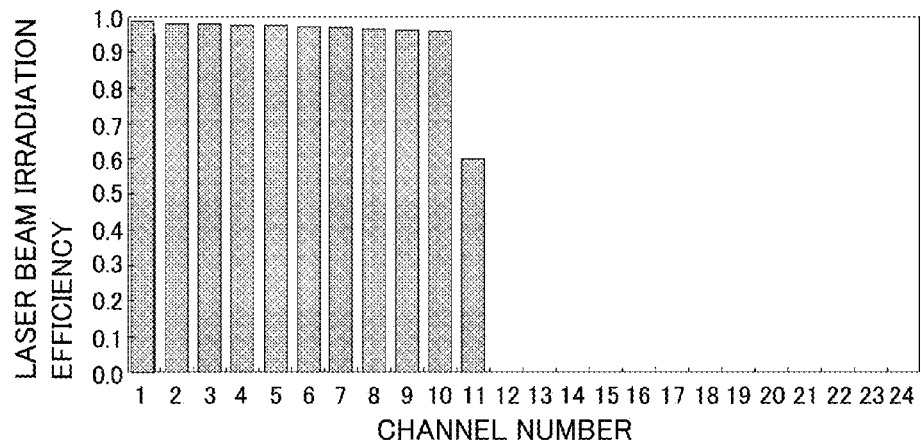
FIGS. 17(a) to 17(c) show diagrams indicating calculation results of irradiation efficiency of side-entry laser beams in microchips where $\theta_1=2°$, $n_2=1.41$, 24 channels.
Figure 17B:
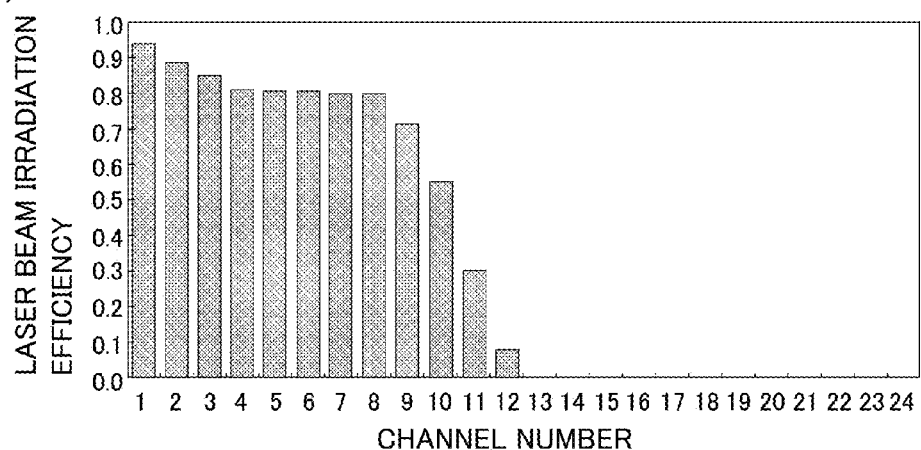
Figure 17C:
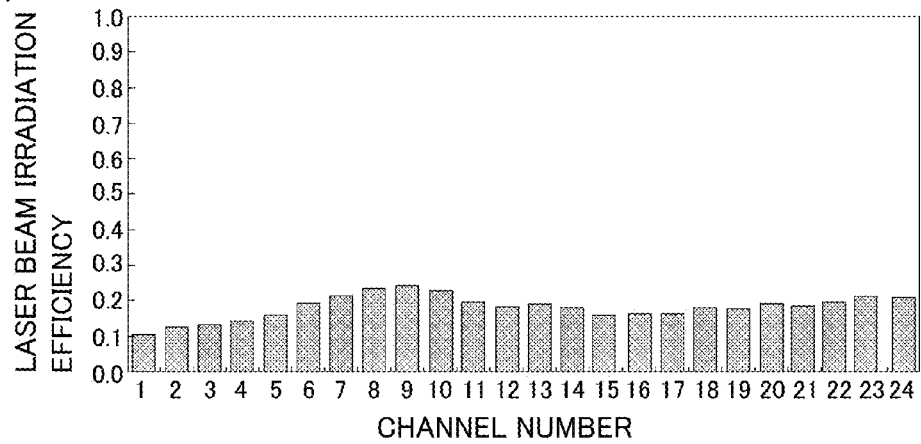

In FIG. 16(a) and FIG. 17(a), in comparison with FIG. 14(a) and FIG. 15(a), a condition which is suitable for beam side-entry is configured by also satisfying Equation (15), although the number of channels which can simultaneously be irradiated is only 11, an average value of the laser beam irradiation efficiencies is significantly improved, and at the same time, dispersion thereof is reduced. In FIG. 16(b) and FIG. 17(b), by a similar effect, in comparison with FIG. 14(b) and FIG. 15(b), the number of channels which can achieve the laser beam irradiation efficiency of 70% or more is increased from 3 to 9. This is important performance in executing a highly sensitive analysis at a number of channels. According to FIG. 16(c) and FIG. 17(c), in comparison with FIG. 14(c) and FIG. 15(c), although an average value of the laser beam irradiation efficiencies concerning 24 channels 2 is reduced from 32% to 18%, a CV value indicating dispersion thereof shows that an effect of reducing from 33% to 19% is achieved. This is important performance in executing a stable analysis at a number of channels. Here, when $\theta 1=2°$, M=7 by Equation (14), a condition of satisfying Equation (20) is b>105 µm, and Equation (20) is satisfied. Further, a condition of satisfying Equation (19) is b>240 µm, and also Equation (19) is satisfied.

According to the present embodiment, it is shown that, by irradiating the laser beam by inclining the laser beam by $\theta_1 > 0°$ to the beam side-entry axis 3, more channels can effectively be irradiated by using a microchip which is provided with plural channels having sections vertical to long axes in an isosceles trapezoidal shape, and irradiating the laser beam from the side face of the microchip, which can contribute to increase an efficiency of analysis and improve a throughput. Although according to the present embodiment, the description has been given by taking an example of a channel having a sectional shape vertical to a long axis in an isosceles trapezoidal shape, a similar effect can be achieved naturally by a trapezoidal shape which is not isosceles, even when a section is configured by a triangular shape, or when each side is configured by a triangular shape, or when each side is not configured by a linear line but a circular arc shape, or even when a corner of a trapezoidal shape or a triangular shape is rounded. Generally, a similar effect can be achieved for a microchip which is provided with plural channels having sections vertical to the long axis in a tapered shape.

Here, consider a case of introducing the laser beam 6 from a lower face of the microchip 1. By Equation (18), an angle of the laser beam 6 irradiated to No. 1 channel 2 relative to the beam side-entry axis 3 is $\theta_1 > 50°$ for any $\theta_0$. Therefore, both of $\theta_1 < 9.74°$ of Equation (9) and $\theta_1 < 2.68°$ of Equation (15) cannot be satisfied, and an efficient beam side-entry system cannot be realized. Therefore, according to the present embodiment, it is a necessary configuration that the laser beam 6 is not introduced from an upper face or a lower face of the microchip 1, but is introduced from the side face of the microchip 1.

[Third Embodiment]

FIGS. 18(a) to 18(c) show a system of carrying out an electrophoresis analysis of DNA included in an organism sample, FIG. 18(a) is a bird's eye view of the microchip 1, FIG. 18(b) is a schematic view showing a section including the beam side-entry axes 3 and 21 of the laser beam 6 and a laser beam 20 of the microchip 1, a section of the fluorescence detection optical systems 13 through 16, and a data analyzing device 17, and FIG. 18(c) shows the two-dimensional fluorescence image 18 provided by the two-dimensional sensor 16. A description will be given as follows centering on a point of FIGS. 18(a) to 18(c) different from FIGS. 15(a) to 15(c).

As shown in FIG. 18(a), the microchip 1 configured by the member of the refractive index $n_1$ is arranged in the medium 0 of the refractive index $n_0$, and the plural channels 2 filled with the member of the refractive index $n_2$ are arranged in the microchip 1. The inlet port 10, and the outlet port are provided at each of the respective channels 2. In order to be able to measure more kinds of fluorescence independently, the laser beam 6 of the wavelength 505 nm and the laser beam 20 of the wavelength 635 nm are introduced from the side face of the microchip 1, and irradiate the array of the channels 2. The laser beam 6 and the laser beam 20 respectively irradiate positions of the respective channels deviated in the long axes directions of the respective channels 2, that is, the beam side-entry axis 3 and the beam side-entry axis 21. In both of the beam side-entry axes, conditions of sectional shapes, array intervals, refractive indexes and the like of the respective channels are the same, and therefore, an equivalent beam side-entry system can be realized. Although generally, the refractive indexes of the respective members differ by the wavelength, and therefore, the differences may influence the performance of the beam side-entry system, wavelength dependencies of the refractive indexes of the respective members used in the present embodiment are small, and therefore, the influence is small. Further, in order to restrain dispersion among the channels 2 of the laser beam irradiation efficiencies, the laser beam 6 and the laser beam 20 are respectively divided into twos, and thereafter irradiates oppositely from the two side faces of the microchip 1. The use of the plural kinds of the laser beams, and introductions of the respective laser beams from the two side faces of the microchip may be carried out simultaneously as described above, or only one of them may naturally be carried out. The rest of the structure of the microchip 1 and the other irradiation conditions of the laser beam 6 and 20, for example, the laser beam widths b in a direction vertical to the array plane and the beam side-entry axis, and the other angle $\theta_1$ made by the center axis of the laser beam relative to the beam side-entry axis are equivalent to either of conditions indicated by the first embodiment or the second embodiment.

As shown in FIG. 18(b), the laser beams 6 and 20 emitted from laser light sources 12 and 22 are divided into twos by using a half-silvered mirror 23 and mirrors 24, thereafter, irradiated from the two side faces of the microchip 1. In FIGS. 18(a) and 18(b), for simplicity, it is expressed that the center axes of the laser beam 6 and the laser beam 20 introduced to the microchip 1 and the beam side-entry axis 3 and the beam side-entry axis 21 are respectively aligned or made to be in parallel with each other, accurately, as shown in the first embodiment or the second embodiment, these are provided with significant angles. A fluorophore-labeled DNA subjected to an electrophoresis in the respective channels 2 is excited in traversing positions irradiated with the laser beam 6 and the laser beam 20, and emit the fluorescence. The fluorescence emitted from the respective channels 2 is detected by the fluorescence detection optical system 13 through 16. That is, the fluorescence is made to be parallel light fluxes by the common condensing lens 13, transmit to a filter and diffraction gratings 14, and imaged on a sensor face of the two-dimensional sensor 16 by the condensing lens 15. The filter is provided for cutting off wavelengths of the laser beam 6 and the laser beam 20 which become background light in detecting fluorescence, and the diffraction gratings are provided for detecting multiple colors by subjecting the fluorescence to wavelength dispersion.

FIG. 18(c) is a schematic view showing a two-dimensional fluorescence image 18 provided by the two-dimensional sensor 16. A direction of the wavelength dispersion is parallel to long axes directions of the respective channels 2 (direction vertical to a sectional view of FIG. 18(b)), that is, vertical to the array direction of the plural channels 2, and therefore, wavelength dispersion images 19 of a laser beam scattering and the fluorescence from the channels 2 by an excitation of the laser beam 6, and wavelength dispersion images 25 of the laser beam scattering and the fluorescence from channels 2 by the excitation of the laser beam 20 are measured independently from each other. By the above-described configuration, a small amount of fluorescence can be identified by increasing the number of kinds of fluorescence which can simultaneously be detected at the respective channels 2, and accurately separating and detecting different fluorescence. According to the present embodiment, a throughput is improved by labeling different samples by respectively different fluorescent materials, and simultaneously analyzing the samples at the same channel.

Figure 25:
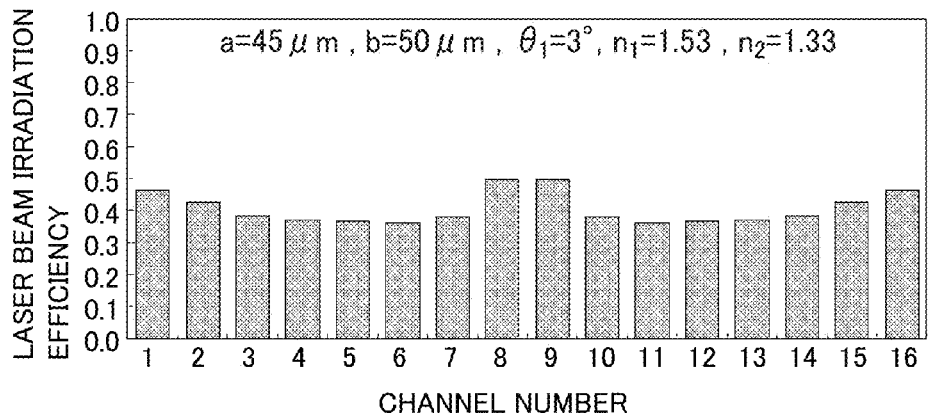
FIGS. 25(a) to 25(c) show diagrams indicating calculation results of irradiation efficiency in cases where two side-entry laser beams were incident from both sides of microchips.
Figure 25:
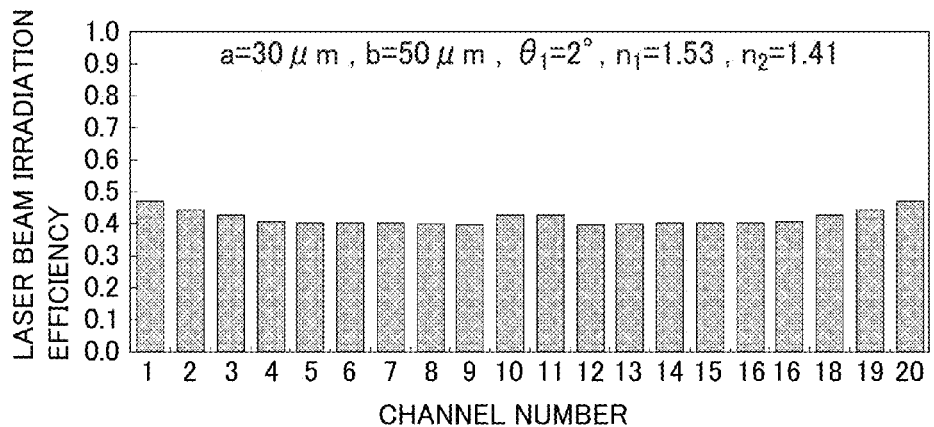
Figure 25:
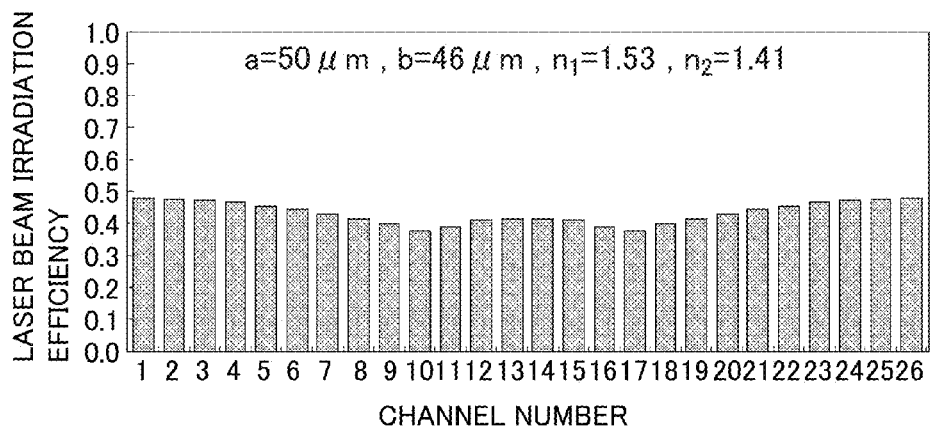

FIGS. 25(a) to 25(c) show an effect in a case of dividing the laser beam 6 in two and irradiating the laser beam 6 from the both side faces of the microchip 1. As shown below, the laser beam irradiation from the both side faces are means which is effective in acquiring uniform fluorescence detection sensitivity by reducing dispersion of the laser beam irradiation efficiencies among the channels 2 while increasing the number of the channels 2 which can simultaneously be irradiated.

Figure 18:
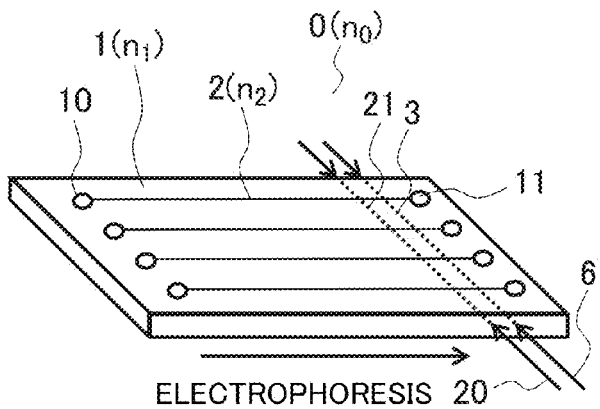
FIGS. 18(a) to 18(c) show outline explanatory views indicating an example of a multichannel analyzer according to the present invention.
Figure 18:
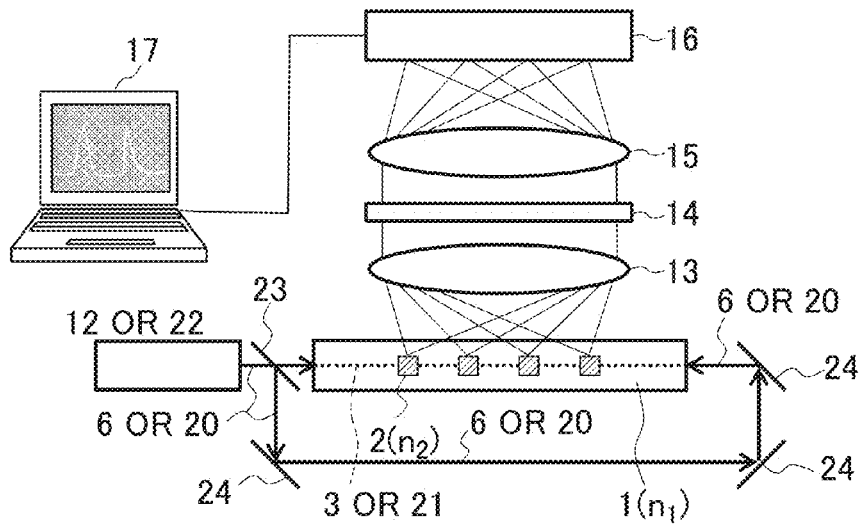
Figure 18:
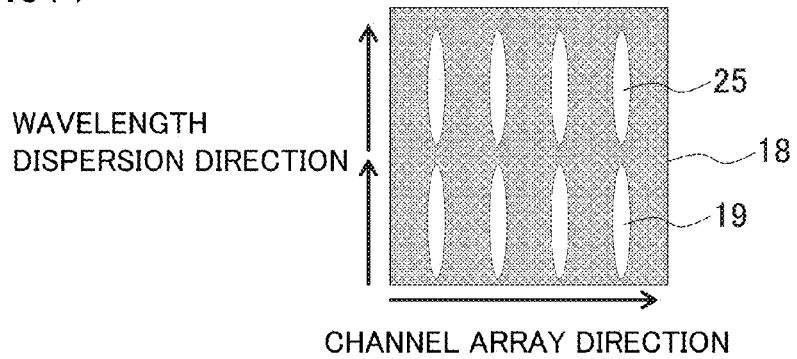

FIG. 25(a) shows laser beam irradiation efficiencies among the respective channels 2 in a case where the total number of the channels 2 is reduced from 24 to 16,and the laser beam 6 is divided in two and irradiated from the both side faces of the microchip 1 in accordance with FIG. 18 under a condition of FIG. 10(b): a=45 μm, b=50 μm, $\theta_1$=3°, $n_1$=1.53, $n_2$=1.33.Here, one of the laser beam 6 divided in two irradiates No. 1 channel 2 from the side face of the microchip 1 similar to FIG. 10(b), and the other irradiates No. 16 channel 2 from a side face on an opposed side of the microchip 1. The two laser beams 6 are symmetric with respect to a boundary by a face vertical to the beam side-entry axis 3 at a center of the channel array, that is, a center point of No. 8 channels 2 and No. 9 channel 2. According to FIG. 11(b), the total number of the channel 2 which can simultaneously be irradiated is 10, an average of the laser beam irradiation efficiencies of the 10 channels 2 is 65%, a standard deviation is 26%, and a CV value is 40%. In contrast thereto, according to FIG. 25(a), the total number of the channels 2 which can simultaneously be irradiated is increased to 16, an average of the laser beam irradiation efficiencies of the 16 channels 2 is as small as 41%, and however, as shown in the standard deviation 5%, and the CV value of 12%, uniform irradiation is enabled among the channels.

FIG. 25(b) shows laser beam irradiation efficiencies of the respective channels 2 in a case where a total number of the channels 2 is reduced from 24 to 20,the laser beam 6 is divided into two and irradiated from the both side faces of the microchip 1 in accordance with FIG. 18(b) in a condition of FIG. 15(b): a=30 μm, b=50 μm, $\theta_1$=2°, $n_1$=1.53, $n_2$=1.41.Similarly, the laser beams 6 divided into two for respectively irradiating No. 1 channel 2 and No. 20 channel 2 symmetrically with respect to a boundary by a face vertical to the beam side-entry axis 3 at a center of the channel array, that is, a center point of No. 10 channels 2 and No. 11 channels 2. According to FIG. 17(b), the total number of the channels 2 which can simultaneously be irradiated is 12, an average of the laser beam irradiation efficiencies of the 12 of the channel 2 is 70%, the standard deviation is 26%, and the CV value is 37%. In contrast thereto, according to FIG. 25(b), the total number of the channels 2 which can simultaneously be irradiated is increased to 20, an average of the laser beam irradiation efficiencies of the 20 channels 2 is as slightly small as 42%, however, the standard deviation is 2%, and the CV value is 6%, and uniform irradiation is enabled among the channels.

[Fourth Embodiment]

In the present embodiment, a description will be given of a case of arranging the plural channels 2 on a circular cylindrical face in accordance with FIG. 4. The microchip 1 in which the channel array is arranged on a curve in this way can be fabricated by several methods. One fabricating means is to design a mold previously such that a desired radius of curvature is obtained at a stage of fabricating parts of the microchip 1 on a lower side and an upper side of the lamination surface 4 in FIG. 4 respectively by the injection molding. The injection molding is good at bending a working surface in this way, and it is easy to bond parts having the same radius of curvature by thermocompression bonding or the like.

Figure 22:
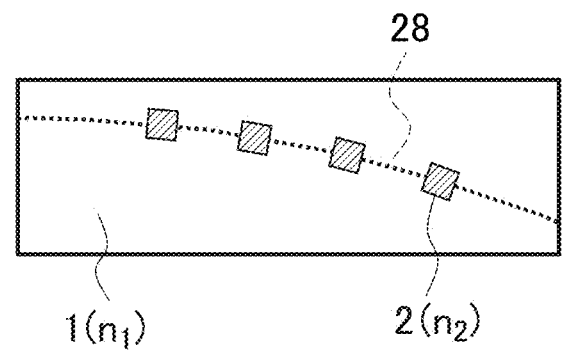
FIGS. 22(a) to 22(c) show configuring views of microchips in which plural channels are arranged on curves.
Figure 22:
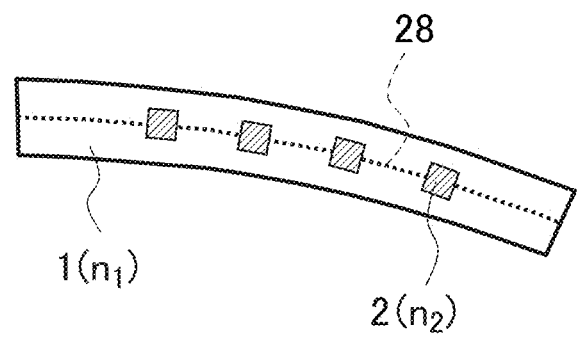
Figure 22:
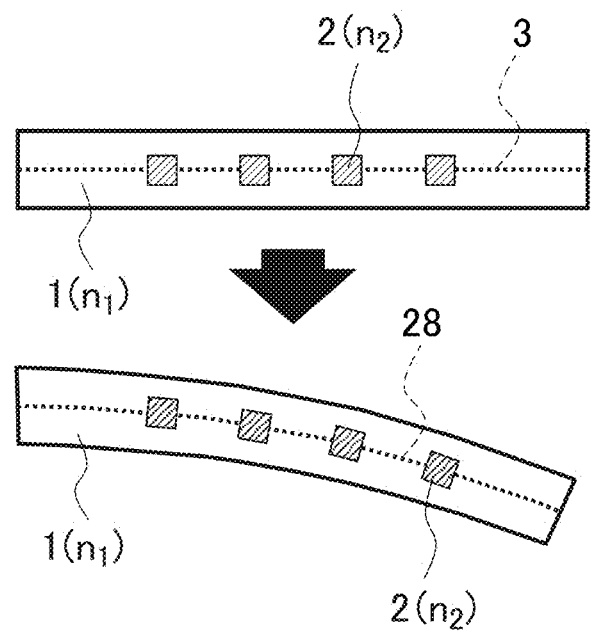

FIGS. 22(a) to 22(c) is a schematic sectional view of the microchip 1 in which the plural channels 2 are arranged on a circular arc of a desired radius of curvature, that is, arranged curvedly on a beam side-entry curve 28. The microchip shown in FIG. 22(a) shows an example in which similarly to FIG. 4, an upper face and a lower face of the microchip 1 are made to be in parallel with each other for the laser beam 6 introduced to the microchip 1. Such a microchip 1 is easy to be installed to an analyzer, and the laser beam 6 is also easy to be adjusted.

Figure 23:
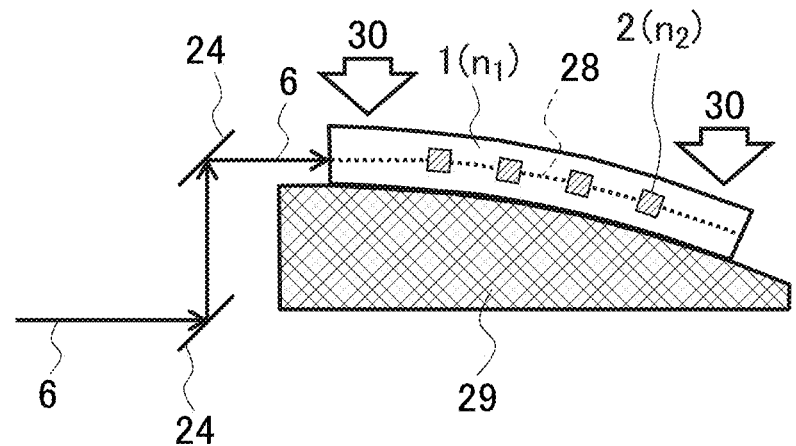
FIGS. 23(a) and 23(b) show explanatory views indicating a mechanism of controlling a radius of curvature of a curved surface on which plural channels are arranged.
Figure 23:
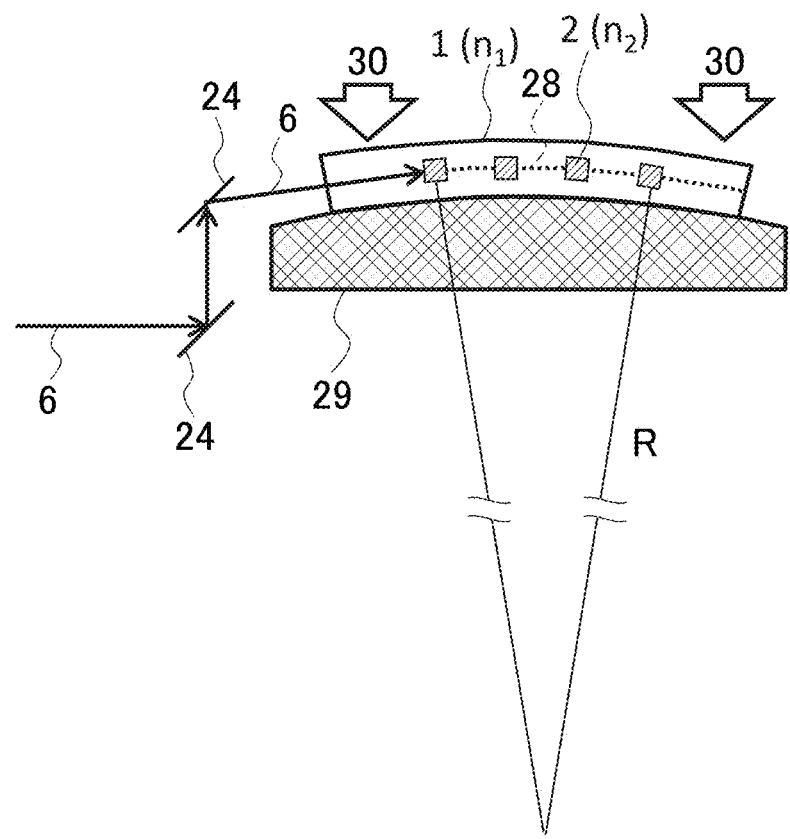

The microchip shown in FIG. 22(b) shows an example in which an upper face and a lower face of the microchip 1 are made to be curved faces having a radius of curvature substantially equivalent to that of the beam side-entry curve 28. In this case, as shown in FIG. 23(a) or FIG. 23(b), it is preferable that also a face of a stage 29 in contact with the microchip 1 for fixing the microchip 1 to an analyzer is made to be a curved face having a radius of curvature substantially equivalent to that of the beam side-entry curve 28. As shown in FIG. 23(a) and FIG. 23(b), it is effective to maintain a desired radius of curvature by pushing the microchip 1 to the stage 29 by applying a push force 30 to the microchip 1. As means for generating the push force, a force of fastening a screw, a force pushed by a motor and the like can be utilized.

According to another fabricating means, although parts on an upper side and a lower side of the microchip 1 are not bent at a stage of carrying out the injection molding, a desired radius of curvature is obtained as shown in FIG. 22(c) by applying a pressure of bending to the microchip 1 at a stage of bonding these, or at a stage after bonding. Further, such a deformation of the microchip 1 may be carried out on an analyzer immediately before a user uses it for measurement. In a case of generating a radius of curvature at a stage after injection molding, the microchip 1 may be designed to be easy to bend. For that purpose, it is effective to make thicknesses of parts of the microchip 1 on a lower side and an upper side of the lamination surface 4 as thin as possible.

In FIG. 4, plural grooves for forming the channel 2 are present at a part on a lower side of the lamination surface 4 of the microchip 1, and further, these are bent, and therefore, it is not easy to thin a thickness of the part. On the other hand, in FIG. 4, the grooves are not present at a part on an upper side of the lamination surface 4 of the microchip 1, and therefore, it is easy to thin a thickness of the part. For example, the part on the upper side can be made to be a resin sheet having a thickness of about 100 μm. On the other hand, in a case of generating a radius of curvature at a stage after injection molding, a draft angle D of each channel 2 can be more or less increased for absorbing a strain thereof. In that case, it is necessary to more or less reduce also a radius of curvature of a curve in accordance therewith. An amount of increasing the draft angle is about $\epsilon_2$ at maximum, and D>>$\epsilon_2$, and therefore, balancing in this way can be carried out. At any rate, it is preferable to design a radius of curvature in accordance with the draft angle at measurement.

It is preferable to design the microchip 1 and an analyzer such that a parameter prescribed in the above-described for realizing an efficient beam side-entry system of a radius of curvature R or the like of the beam side-entry curve 28 on which a center of each channel 2 is mounted becomes a desired value, or the plural channels 2 can sufficiently be irradiated with a laser beam by only installing the microchip 1 to an analyzer by a user. However, it is assumed that R or the like is deviated from a designed value by being caused by dispersion in a working accuracy, a deformation by deterioration or the like of the microchip 1, or a deformation or the like by an environmental factor of an analyzer. Therefore, it is effective to make R or the like near a design value by an adjustment, or provide an analyzer with a calibration mechanism to be able to irradiate the laser beam to the plural channels 2 further efficiently. For example, it is effective to control a degree of a curve of the microchip 1 by adjusting a magnitude of the push force 30 of FIG. 23(a) or FIG. 23(b) while monitoring a signal intensity from each channel 2 on an analyzer before starting to analyze a sample such that the above-described signal intensity is made to near a design value or such that the laser beam can be irradiated efficiently to the plural channels 2.

In this case, it is not necessarily needed that a contact face of the stage 29 for fixing the microchip 1 has a radius of curvature substantially equivalent to that of the beam side-entry curve 28 as in FIG. 23(a) or FIG. 23(b). Rather, it is effective to be able to control the radius of curvature of the beam side-entry curve 28 in a wide range including a radius of curvature which is considered to be optimum by providing the contact face with a radius of curvature substantially smaller than the radius of curvature which is considered to be optimum in design. It is also effective to execute such an adjusting method in a case where the microchip 1 is deformed by being caused by heat generation or the like, R or the like is changed by changing a refractive index of each member, or the optimum value of R or the like is changed in the midst of analysis. As the signal intensity, it is convenient to utilize a Raman scattering intensity or the like of water. It is also effective to previously incorporate a marker for calibration at an inner portion of the microchip 1 other than a channel used for analyzing a sample. For example, channels 31 for calibration are provided on both sides of an array of the channel 2 used for analysis as shown in FIG. 24(b). An inner portion of the channel 31 is filled with a medium which can emit a comparatively strong Raman scattering having a refractive index of $n_2$ similar to the channel 2. A pertinent radius of curvature R is obtained by controlling a magnitude of the push force 30 of FIG. 23(a) and FIG. 23(b) while monitoring the Raman scattering intensity provided from the channel 31. Further, light emission from the channel 31 can be measured simultaneous with and independently from light emission from the channels 2 by the fluorescence detection optical system of FIG. 5(b), and therefore, the push force 30 can also be controlled in real time while carrying out an analysis. This is effective as a method of dealing with a case where the microchip is deformed by, for example, a temperature rise or the like in the midst of an analysis.

Figure 19:
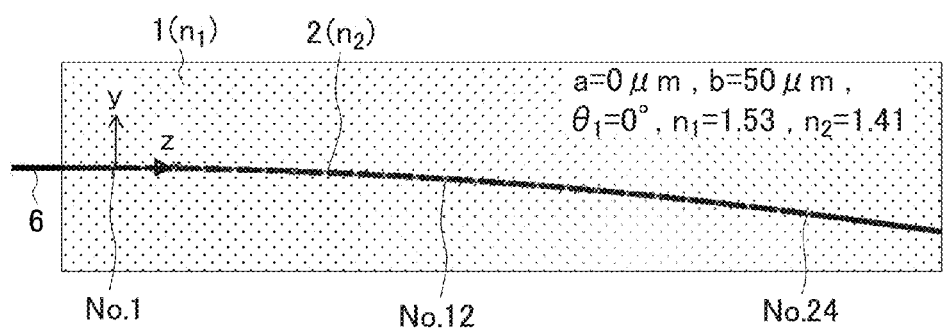
FIGS. 19(a) and 19(b) show diagrams indicating a light ray trace simulation result and irradiation efficiency calculation results of a side-entry laser beam in a microchip where 24 channels are arranged on a curve.
Figure 19:
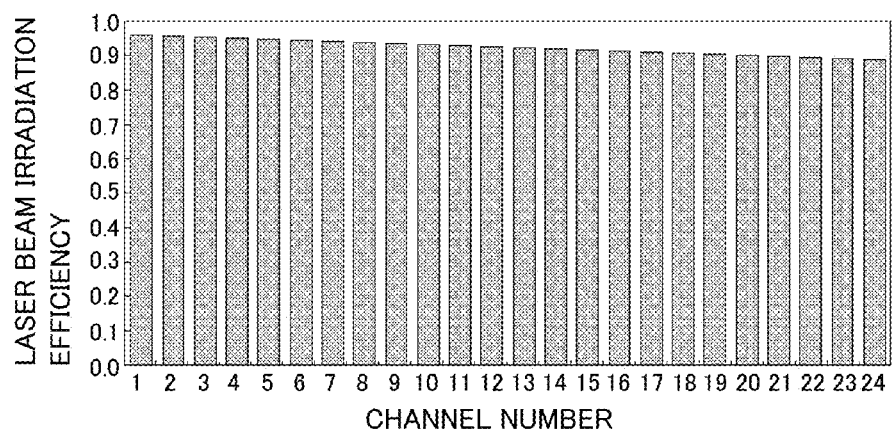

FIG. 19(a) shows a result of a light ray trace simulation in a case where the plural channels 2 are arranged on a curve at an inner portion of the microchip 1, and the laser beam 6 is made to be horizontally incident on the side face of the microchip 1 in accordance with FIG. 4. Unless particularly specified otherwise, a condition and a displaying method are similar to those of FIG. 12(b) and FIG. 13(b). A center axis 5 of the laser beam 6 incident on No. 1 channel irradiated a center of No. 1 channel, and it was made to be in parallel with an upper base and a lower base of an isosceles trapezoidal shape configuring a section of No. 1 channel 2. Center positions of the respective channels 2 of No. 1,through No. 24 were arranged on a beam side-entry curve having a radius of curvature R of about 55 mm. At this time, R=55 mm in Equation (21), and therefore, Equation (21) is generally satisfied. Further, Equation (22) is 27 mm<R<110 mm, Equation (23) is 46 mm <R<68 mm, and therefore, either of these is satisfied. Here, p=300 μm, $\epsilon_2$=−0.31°. The respective channels 2 were inclined along the beam side-entry curve such that the laser beam 6 was in parallel with an upper base and a lower base of an isosceles trapezoidal shape configuring sections of the respective channels 2. That is, an angle made by a direction of an upper base and a lower base of an isosceles trapezoidal shape configuring a section of No. 1 channel 2 and a direction of an upper base and a lower base of an isosceles trapezoidal shape configuring a section of No. N channel 2 was made to be (N−1)×|$\epsilon_2$|. Here, N is an arbitrary integer from 1 to 24.

As shown in FIG. 19(a), all of beam elements advanced along the beam side-entry curve 28, and were not deviated from the channel array at all. As a result, the laser beam irradiation efficiencies of all of the channels 2 from No. 1, to No. 24 were at extremely high levels as shown in FIG. 19(b). A small attenuation of the laser beam irradiation efficiencies in accordance with channel numbers is caused by a reflection loss of the laser beam 6 at the side faces of the channel 2 of the laser beam 6. Therefore, the laser beam irradiation efficiencies shown in FIG. 19(b) are an ideal result.

Figure 20A:
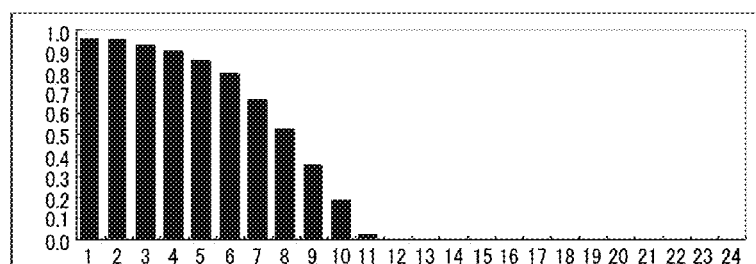
FIGS. 20(a) to 20(e) show diagrams indicating calculation results of irradiation efficiency of side-entry laser beams in microchips where 24 channels are arranged on various curves.
Figure 20B:
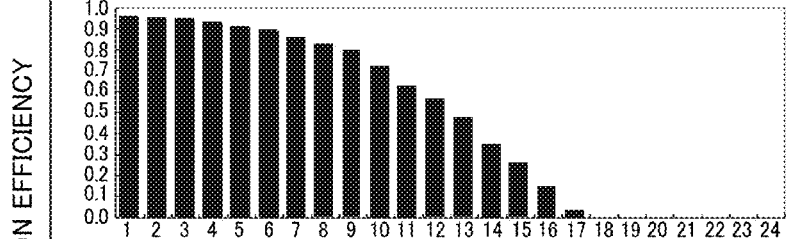
Figure 20C:
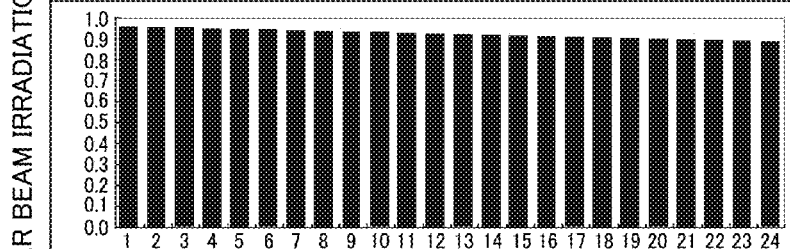
Figure 20D:
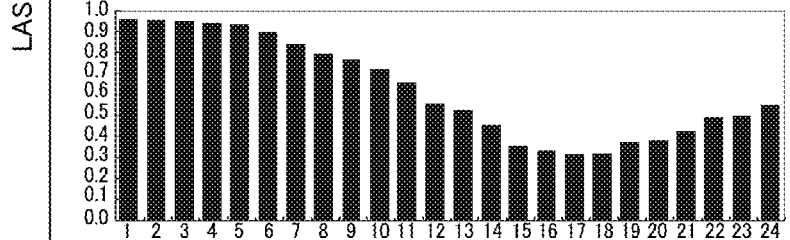
Figure 20E:
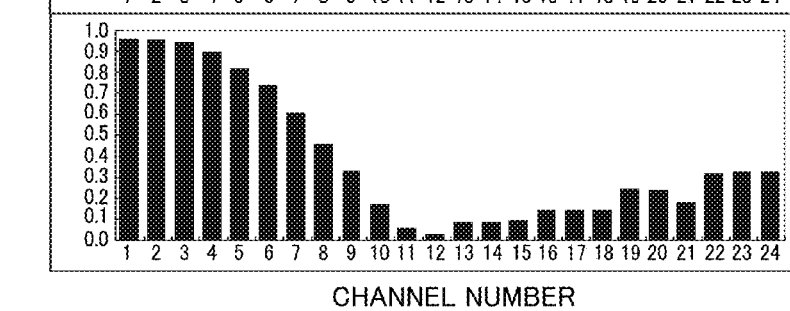

FIGS. 20(a) to 20(c) show results of carrying out a similar calculation concerning different radii of curvature R. FIGS. 20(a), 20 (b), 20(c), 20(d), and 20 (e) respectively show laser beam irradiation efficiencies of 24 channels 2 in a case of R=37 mm, 46 mm, 55 mm, 68 mm, and 110 mm, respectively. That is, a result of FIG. 20(c) is the same as a result of FIG. 19(b). In this way, the laser beam irradiation efficiencies were reduced in accordance with distance of R from 55 mm at which the radius of curvature R is an optimum value. In FIG. 20(d) and FIG. 20(e), a reason of reducing the laser beam irradiation efficiencies in accordance with channel numbers and thereafter turning to increase is that there are beam elements which are once deviated from the channel array by refraction by the channels 2 and irradiate again the channels 2 at a later stage which is arranged on a curve in the same direction. Although both of conditions of FIGS. 20(a) and 20(e) do not satisfy Equation (23), 27 mm<R<110 mm of Equation (22) is satisfied, and therefore, efficient laser beam irradiation can be realized in comparison with FIG. 13 (b). On the other hand, FIGS. 20(b) and 20(d) satisfy also 46 mm<R<68 mm of Equation (23) in addition to Equation (22), and therefore, further efficient laser beam irradiation can be realized.

FIG. 25(c) show laser beam irradiation efficiencies at the respective channels 2 in a case where in a condition of FIG. 20(b): b=50 μm, R=46 mm, $n_1$=1.53,$n_2$=1.41,the total number of the channels 2 is increased from 24 to 26,and the laser beam 6 is divided into two to irradiate from both side faces of the microchip 1 in accordance with FIG. 18. Here, one of the laser beam 6 divided into two irradiates No. 1 channel from a side face of the microchip 1 similarly to FIG. 20(b), the other irradiates No. 26 channel 2 from a side face on an opposed side of the microchip 1, symmetrically with respect to a boundary by a face vertical to the beam side-entry curve 28 at a center of the channel array, that is, a center point of No. 13 channels 2 and No. 14 channel 2. According to FIG. 20(b), the total number of the channels 2 which can be irradiated simultaneously is 17, an average value of the laser beam irradiation efficiencies of the 17 channels 2 is 66%, the standard deviation 31%, and the CV value is 46%. In contrast thereto, according to FIG. 25(c), the total number of the channels 2 which can simultaneously be irradiated is increased to 26, although an average of the laser beam irradiation efficiency of the 26 channels 2 is rather small as 43%, uniform irradiation can be carried out among channels with the standard deviation of 4%, and the CV value of 8%.

Fifth Embodiment

A side and a front face of the microchip are defined as follows. Consider a rectangular parallelepiped of a minimum size surrounding a total of a microchip. In a case where a microchip is configured by a rectangular parallelepiped, the microchip and the rectangular parallelepiped coincide with each other. Lengths of different 3 sides of the rectangular parallelepiped are made to be a, b, c, in turn from longer ones (a≥b≥c). Hereinafter, a surface of a microchip in contact with, (or proximate to) two rectangles of a×b of the rectangular parallelepiped is referred to as "front face", and a surface of a microchip in contact with (or proximate to) two rectangles of a×c and two rectangles of b×c are referred to as "side face". In a case of providing the plural channels at the inner portion of the microchip, the plural channels are frequently arranged in parallel with the front face. Further, although there is frequently a case where the front face and the side face are substantially vertical to each other, there is also a case where the front face and the side face are inclined in a range of 90°±45°.

When a microchip made of resin having a single channel was fabricated, and a side face irradiation system (beam side-entry system) of the laser beam was tried, it became newly apparent that there was a case where a laser intensity reaching the channel was considerably attenuated, in comparison with the laser intensity before being incident on the microchip, and the fluorescence detection sensitivity of the channel was reduced against expectation less than that in a front face irradiation system (a system of carrying out a laser beam irradiation and fluorescence detection both from the front face). When a cause thereof was investigated, the reason was that although the front face of the microchip is brought into a smooth surface, a surface roughness of the side face was large, and the side face was not brought into a smooth surface, and therefore, scattering when the laser beam was incident on the side face was large. As a result, simultaneously with attenuating an intensity of a laser incident on the microchip, a laser beam width at an inner portion of the microchip was enlarged in comparison with that before being incident, and an effective intensity of the laser irradiating the channel was significantly reduced.

When investigated further, it was predicted that a cause of bringing the microchip into such a state was in a step of fabricating the microchip by the injection molding. That is, as described later in reference to FIGS. 26(a) to 26(c), when a flat type resin substrate (in correspondence with the part 9 on an upper side of the lamination surface 4 of FIGS. 3(a) to 3(c)) and a recessed type resin substrate (in correspondence with apart 8 on a lower side of the lamination surface 4) of FIGS. 3(a) to 3(c) which became parts of the microchip made of resin were taken out from a mold, although a direction of moving the mold in contact with the front face of each substrate was vertical to the front face, a direction of moving the mold (not illustrated inFIGS. 3(a) to 3(c)) in contact with the side face of the microchip was in parallel with the side face, and therefore, it was considered that the side face was roughened. On the other hand, also in a case of cutting the microchip vertically to the front face (in parallel with the side face), the surface roughness of the side face was increased. Also in such a case, similarly, scattering was enlarged when the laser beam was incident on the surface.

It is a merit of microchips made of resin can be mass-produced at low cost by using a mold by injection molding, nanoimprinting or the like. Although cost and labor can be taken by including a method other than the injection molding or the nanoimprinting, it is easy to resolve the problem described above, thereby, the merit of the microchip made of resin is lost. Hence, according to the present embodiment, in order to resolve the problem described above without considerably increasing cost and labor of making a microchip, the surface roughness of the side face of the microchip made of resin is reduced, and the side face is smoothed. Thereby, an incidence efficiency of the laser beam from the side face is increased, the attenuation of the laser intensity and an enlargement of the laser beam width are restrained, and highly sensitive fluorescence detection of the channel can be carried out.

In the following, it is proposed to execute the above-described at a lower cost. Although in order to reduce the surface roughness, there are several means of grinding, polishing and the like, even when any of the means is used, if whole surfaces of all the side faces are smoothed, its step is complicated and requires time, and cost is increased. Hence, only a partial surface of a side face at a vicinity of the position at which the laser beam is incident is selectively smoothed. That is, in the side face of the microchip, an average of the surface roughness of an area of a side face including a position at which the laser beam is incident and a surrounding thereof is made to be smaller than an average of the surface roughness of the other area of the side face or the other side face. Thereby, a step which is needed by addition, and time are restrained to a minimum, and the problem can be resolved while restraining necessary cost. In addition, it is proposed that also a surface roughness of aside face at a vicinity of a position from which the laser beam is emitted from a side face on a side opposed to the side face on which the laser beam of the microchip is incident thereon is selectively reduced and smoothed. Thereby, laser beam scattering of the side face when the laser beam is emitted from the microchip is restrained, and a reduction of sensitivity of detecting fluorescence of a channel thereby can be avoided.

Although any method can be used for a method for smoothing the side face locally, as a specific example, the following three systems are proposed. As described later, the problem was resolved by any of the system, it was confirmed by experiments that the effect was achieved.
(1) when a resin substrate is subjected to injection molding, a mold in contact with the faces is escaped in a vertical direction, and the mold is separated
(2) after subjecting the resin substrate to injection molding, the side faces are smoothed by grinding, polishing or the like
(3) after subjecting the resin substrate to injection molding, glass windows or the like are adhered to the side faces Any material of a resin may be used in the present invention. As materials suitable for a microchip, there are known acrylic resin (PMMA), polycarbonate (PC), polystyrene (PS), cycloolefin polymer (COP), cycloolefin copolymer (COC) and the like, and any of these may be used. According to the present invention, COP was selected as an example, and ZEONOR of Nippon Zeon (Co.) which was a commodity thereof was used.

Figure 26:
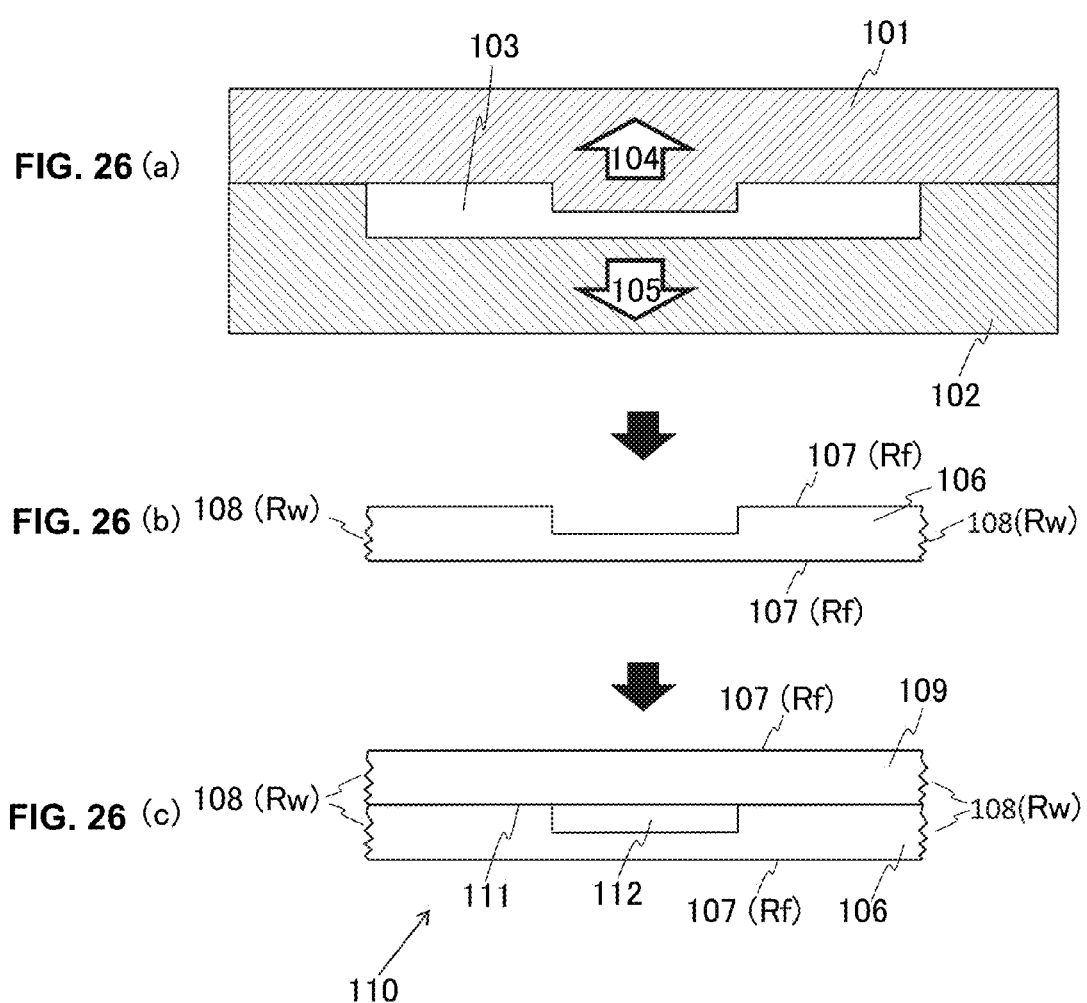
FIGS. 26(a) to 26(c) show explanatory views of a comparative example of a procedure of fabricating a microchip made of resin by injection molding.

FIGS. 26(a) to 26(c) show a procedure of fabricating a microchip made of resin by the injection molding as a comparative example. FIG. 26(a) shows sectional views of a core mold 101 (in correspondence with the mold 7 of FIG. 3(a)) and a cavity mold 102, showing a state of closing the two molds. A resin melted by heat is made to flow into a space 103 surrounded by the two molds, and the resin is cooled to be cured. The molds are opened by moving the core mold 101 in a direction of an arrow 104, and the cavity mold 102 in a direction of an arrow 105. As a result, as shown by a sectional view in FIG. 26(b), a molded recessed shape resin substrate 106 (in correspondence with the part on the lower side of the lamination surface 4 of FIG. 3(b)) is obtained. Here, according to both of the upper and lower front faces of the recessed resin substrate 106, the core mold 101 contacting with the upper front face and the cavity mold 102 contacting with the lower front face are separated in a direction vertical to both of the front faces 107, and therefore, a surface roughness Rf of the front faces 107 are small and a smooth surface can be brought about. Naturally, faces in contact with the front faces 107 of the respective molds need to be brought into a smooth surface previously.

On the other hand, according to both left and right side faces 108 of the recessed resin substrate 106, the cavity mold 102 contacting with the both side faces is separated in a direction in parallel with the both side faces 108, and therefore, surfaces of the both side faces 108 are roughened, at that occasion, a surface roughness Rw of the side face 108 is large, and a smooth surface cannot be brought about. That is, a relationship Rf<Rw is established. This is unavoidable even when a face in contact with the side face 108 of the cavity mold 102 is previously brought into a smooth surface. Hereinafter, in the sectional view of the microchip, it is expressed that a surface of a face indicated by a straight line is smoothed, and a surface face indicated by a wave line is not smooth.

The microchip 110 is obtained as shown by a sectional view in FIG. 26(c), by fabricating a flat type resin substrate 109 (in correspondence with the part 9 on the upper side of the lamination surface 4 of FIG. 3(c)) is also fabricated by the injection molding similarly, and pasting the flat type resin substrate 109 with the recessed type resin substrate 106 by configuring a boundary by the lamination surface 111. A recess provided at the front face of the recessed type resin substrate 106 forms a channel 112 at an inner portion of the microchip 110. Although in FIG. 26(c) a procedure of fabricating the microchip 110 having a single channel 112 is shown, a microchip having plural channels can be fabricated by a similar procedure.

FIGS. 27(a) and 27(b) are explanatory views showing a laser scattering by the surface roughness of the side face of the microchip. FIG. 27(a) is a front view in a case where the laser beam 115 is introduced to the microchip 110 of FIG. 26(c) from the side face 108 in parallel with the front face 107, and FIG. 27(b) shows a cross-sectional view thereof. Since the surface roughness Rw of the side face 108 is large, the laser beam 115 brings about a laser scattering 116 considerably at the side face 108, and the intensity of the laser incident on the inner portion of the microchip 110, that is, an intensity of a laser reaching the channel 112 is small. Hereinafter, the side face 108 indicates a portion of the side face of the microchip 110 on which the laser beam 115 is incident, and a portion thereof at which the laser beam 115 is emitted. The other portion of the side face is referred to as a side face 114. Further, a surface roughness of the side face 108 is referred to as Rw, and a surface roughness of the side face 114 is referred to as Rs. In a state of FIGS. 27(a) and 27(b), naturally, a relationship of Rf<Rw≈Rs is established. Hereinafter, Rf, Rw, and Rs are made to be average values of the surface roughness at object areas.

FIGS. 28(a) and 28(b) are explanatory views in a case of adopting means for "(1) escaping and separating the molds in contact with the side faces in a vertical direction when a resin substrate is subjected to the injection molding" as means for "effectively reducing only the surface roughness of the side face at a vicinity of the position on which the laser beam is incident to be smooth", showing a procedure of fabricating a microchip made of resin by the injection molding. FIG. 28(a) is provided with a slide mold 117 in addition to the core mold 101, and the cavity mold 102, unlike FIG. 26(a). The slide mold 117 is moved in an arrow direction 119 by being interlocked with moving the core mold 101 in the direction of the arrow 104. That is, as shown in a sectional view of FIG. 28(b), according to a portion (made to be side face 108) in contact with the slide mold 117 in FIG. 28(a), the slide mold 117 contacting with the side face 108 is separated in a vertical direction to the side face 108, and therefore, similar to the surface roughness Rf of the front face 107, the surface roughness Rw of the side face 108 can be made to be small to bring about a smooth surface (Rf≈Rw). Naturally, a face in contact with the side face 108 of the slide mold 117 needs to be brought into a smooth surface previously.

Figure 30:
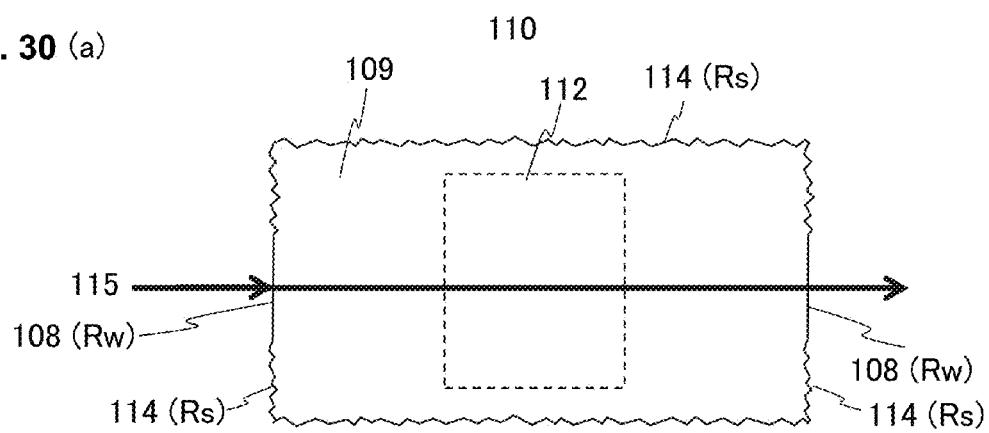
FIGS. 30(a) and 30(b) show views indicating an example of irradiating a laser beam on a smoothed surface of a microchip.
Figure 30:
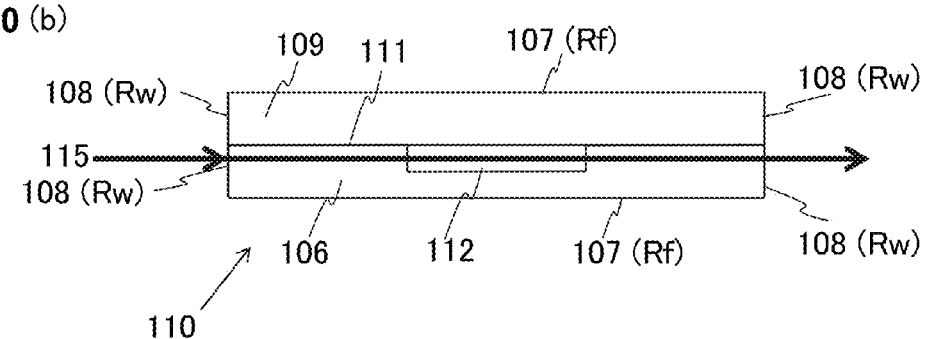

Here, although not shown in FIG. 28(b), a side face 114 disposed on a front side or on a reverse side FIG. 28(b) is not brought into contact with the slide mold 117, and therefore, a surface roughness Rs stays to be large similar to FIG. 27(b) (refer to FIG. 30(b)). Although in FIG. 28(a), an example of a mold structure of an injection molding for smoothing the side face 108 is shown, naturally, the recessed shape resin substrate 106 and the microchip 110 having a similar characteristic may be fabricated by the other method.

The microchip 110 having a smooth side face 108 can be obtained as shown in a sectional view of FIG. 28(c) by fabricating also the flat shape resin substrate 109 by similar method and pasting together with the recessed shape resin substrate 106 by configuring a boundary by the lamination surface 111.

Figure 29:
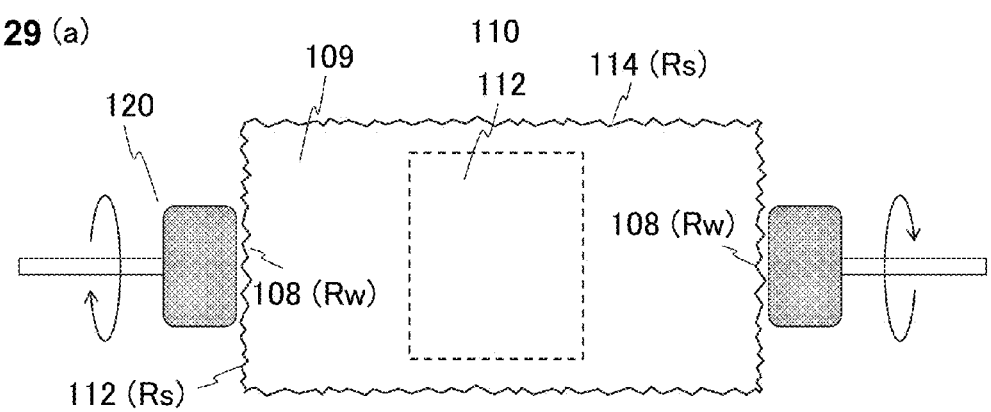
FIGS. 29(a) and 29(b) show views indicating an example of locally grinding a side face of a microchip.
Figure 29:
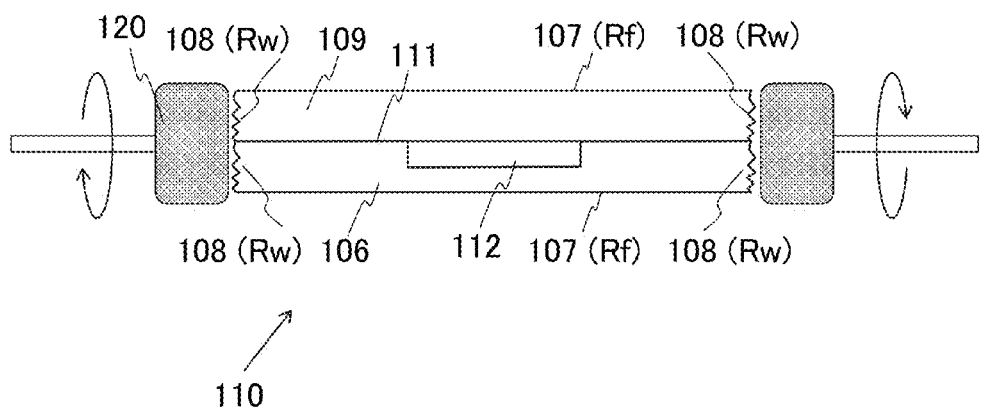

FIGS. 29(a) and 29(b) are explanatory views in a case of adopting means for "(2) smoothing the side faces by grinding, polishing or the like after subjecting a resin substrate to an injection molding" as means for "selectively reducing to smooth only a surface roughness of the side face at a vicinity of a position on which the laser beam is incident", showing an example of selectively polishing the side face 108 of the microchip 110 shown in FIGS. 27(a) and 27(b). FIG. 29(a) shows a front view, and FIG. 29(b) shows a cross-sectional view thereof.

Here, there is shown an example in which a polishing buff is attached to a front end of a grinder to rotate, and polishing the side face 108 by bringing into contact with the side face 108. Naturally, the side face 108 may be polished or ground by the other means. However, a whole surface of the side faces of the microchip 110 is not polished or ground but only part surfaces of the side faces 108 on which the laser bean is incident and from which the laser beam is emitted are polished or ground.

FIGS. 30(a) and 30(b) are schematic views in a case of introducing the laser beam 115 to the microchip 110 fabricated by the means of FIGS. 28(a) and 28(b) and FIGS. 29(a) and 29(b) in parallel with the front face 107. FIG. 30(a) shows a front view, and FIG. 30(b) shows a cross-sectional view thereof. Unlike a case of FIGS. 27(a) and 27(b), the surface roughness Rw of the side face 108 is small, and therefore, the laser beam 115 is not considerably scattered at the side face at which the laser beam 115 is incident on the microchip 110, and an intensity of the laser incident on an inner portion of the microchip 110, that is, an intensity of the laser reaching the channel 112 is high. Further, the laser beam 115 is not considerably scattered even at the side face 108 at which the laser beam 115 is emitted from the microchip 110, and therefore, scattered light does not increase an intensity of background light in detecting fluorescence. Here, although similar to the surface roughness Rf of the front face of the microchip 110, the surface roughness Rw of the side face 108 on which the laser beam 115 is incident and from which the laser beam 115 is emitted is small, the surface roughness Rs on the other part of the side face 114 stays to be large. That is, a relationship of Rf≈Rw<Rs is established.

Highly sensitive fluorescence detection of the channel configured at an inner portion can be carried out by using the microchip 110 made of resin which can be fabricated at low cost by the above-described configuration. Further, although in FIGS. 28(a) and 28(b), FIGS. 29(a) and 29(b), and FIGS. 30(a) and 30(b), an example of smoothing both of the side face 108 on which the laser beam is incident, and the side face 108 from which the laser beam is emitted is shown, a similar effect can be improved without necessarily smoothing the side face 108 from which the laser beam is emitted.

Generally, the channel 112 is present not on a side of the flat shape resin substrate 109 but on a side of the recessed shape resin substrate 106, and therefore, as shown in FIGS. 30(a) and 30(b), it is efficient to introduce the laser beam 115 from the side face 108 on the side of the recessed shape resin substrate 106. Therefore, as shown in FIG. 31(a), the microchip 110 may be fabricated by smoothing only the side face 108 of the recessed type resin substrate 106 without smoothing the side face 108 of the flat shape resin substrate 109. Further, the side face 108 is not necessarily vertical to the front face 107, but there is also a case where the side face 108 is inclined. Also in such a case, even when the surface roughness of the side face 108 is similarly reduced, as shown in FIGS. 31(b) and 31(c), when an inclination of a center axis of the laser beam 115 before being incident on the microchip 110 is controlled in consideration of refraction at the side face 108, the channel 112 can be irradiated from a desired direction by a strong laser intensity while avoiding laser scattering at the side face 108.

FIGS. 32(a) and 32(b) are explanatory views in a case of adopting means for "(3) adhering glass windows or the like on the side faces after subjecting a resin substrate to the injection molding", as means for "selectively reducing to smooth only the surface roughness of the side face at a vicinity of a position on which the laser beam is incident". According to the present embodiment, a glass window 122 is adhered to the side face 108 of the microchip 110 shown in FIGS. 27(a) and 27(b) via an adhering agent 121. The glass window 122 is a small piece of a glass plate previously smoothing the both front faces (in FIGS. 32(a) and 32(b), left and right faces of the glass window 122) and the both front faces are in parallel with each other. FIG. 32(a) shows a front view, and FIG. 32(b) shows a cross-sectional view thereof. As shown in FIGS. 32(a) and 32(b), whereas the adhering agent 121 absorbs the surface roughness by entering small recesses and protrusions on the surface of the side face 108, the free front face of the glass window 122 is smooth, and therefore, substantially, in the side faces, only the side face 108 can selectively be smoothed. That is, here, it is a characteristic that a relationship of Rf≈Rw<Rs is established.

By the above-described, an intensity of a laser incident on the inner portion of the microchip 110, that is, an intensity of a laser reaching the channel 112 is increased without being scattered considerably at the side face 108 at which the laser beam 115 is incident on the microchip 110. Further, the laser beam 115 is not scattered considerably even at the side face 108 at which the laser beam 115 is emitted from the microchip 110, and therefore, the scattered light does not increase the intensity of background light in detecting fluorescence. As a result, highly sensitive fluorescence detection of the channel configured at the inner portion can be carried out by using the microchip 110 made of resin which can be fabricated at low cost. Further, although in FIGS. 32(a) and 32(b), an example of smoothing both of the side face 108 on which the laser beam is incident and the side face 108 from which the laser beam is emitted is shown, a similar effect can be achieved without smoothing necessarily the emitting side face 108.

It is preferable that viscosity of the adhering agent 121 is low at least in a state before curing such that the adhering agent 121 enters fine recesses and protrusions of the surface of the side face 108, and air bubbles or the like do not enter the adhering agent 121. It is preferable that the viscosity of the adhering agent 121 before curing is made to be, preferably, 1000 mPa*s or smaller, further preferably, 100 mPa*s or smaller. On the other hand, it is preferable that the adhering agent 121 after curing is solid such that the glass window 122 does not come off from the side face 108. As a material of the glass window 122, for example, quartz excellent in an optical property is selected. As the material of the microchip 110, for example, ZEONOR is used. In this case, whereas a refractive index of quartz is 1.46, a refractive index of ZEONOR is 1.53, and a big difference is present between the refractive indexes of the both. In such a case, it is preferable that the refractive index of the adhering agent 121 is made to be a vicinity of the refractive index of either of the both, or a refractive index at a middle of the both.

Whereas a surface of the glass window is smooth, the side face 108 of the microchip 110 is not comparatively smooth, recesses and protrusions of the surface are large, and therefore, it is further preferable that the refractive index of the adhering agent 121 is made to be not near the refractive index of the glass window 122 but near the refractive index of the microchip 110. Naturally, it is further preferable that the refractive indexes of the glass window 122 and the microchip 110 are made to be nearer. For example, a slide glass (Matsunami, S1111) for a microscope can be used. The slide glass is fabricated from crown glass, a refractive index thereof is 1.52, and therefore, the refractive index of crown glass is very near the refractive index 1.53 of ZEONOR. Further, not the glass window, but a resin window may be configured. In that case, as a material of a resin, it is preferable to use a material the same as that of the microchip 110. However, it is necessary that the both front faces of the resin window is made to be smooth previously. For example, the adhering agent 121 which is cured by irradiating UV agrees with the above-described.

Figure 31:
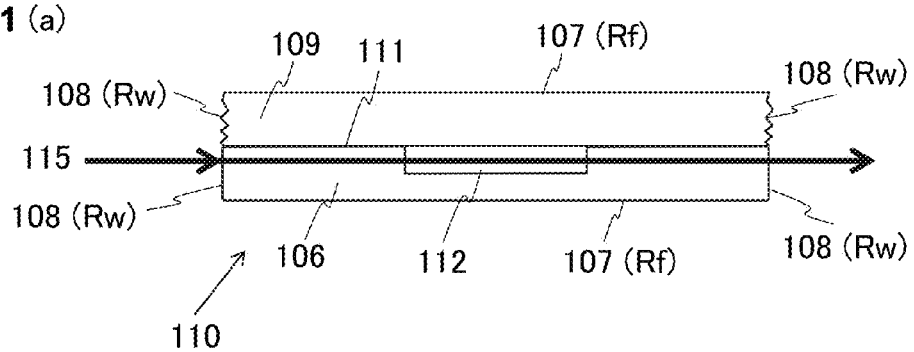
FIGS. 31(a) to 31(c) show views showing examples of irradiating laser beams to side faces of microchips.
Figure 31:
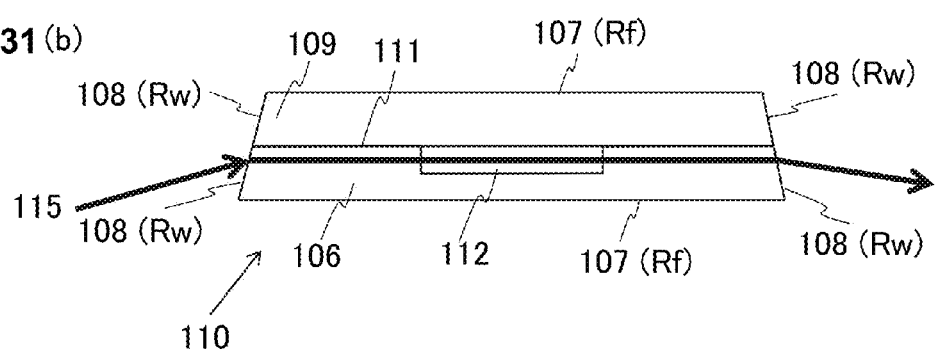
Figure 31:
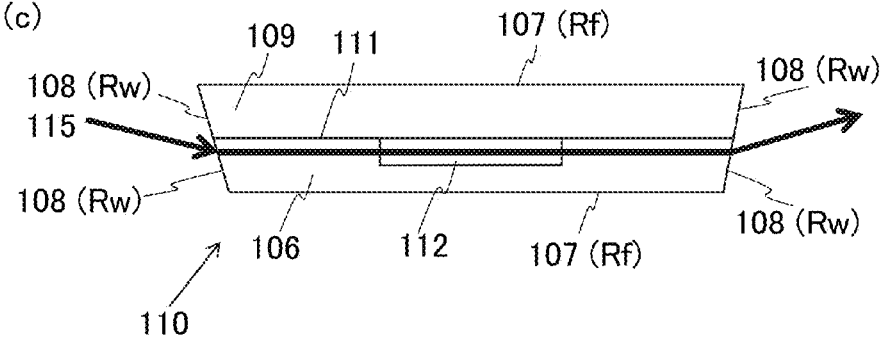
Figure 32:
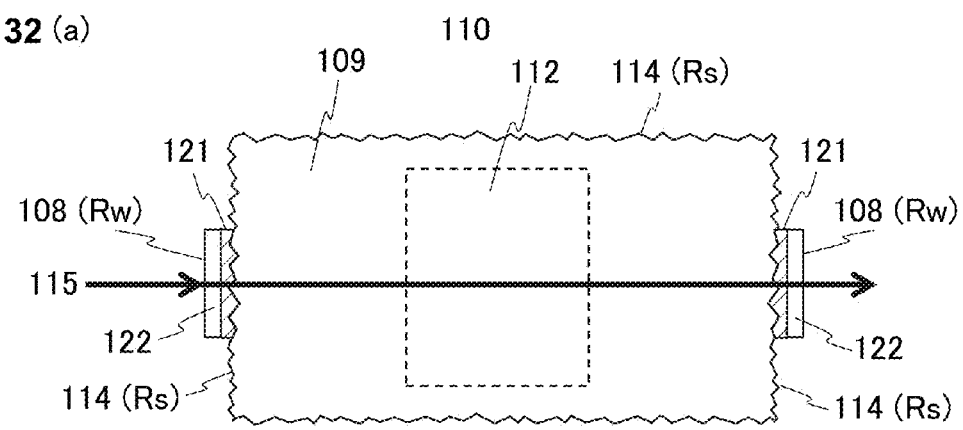
FIGS. 32(a) and 32(b) show views indicating an example of irradiating a laser beam to a glass-window adhered side face of a microchip.
Figure 32:
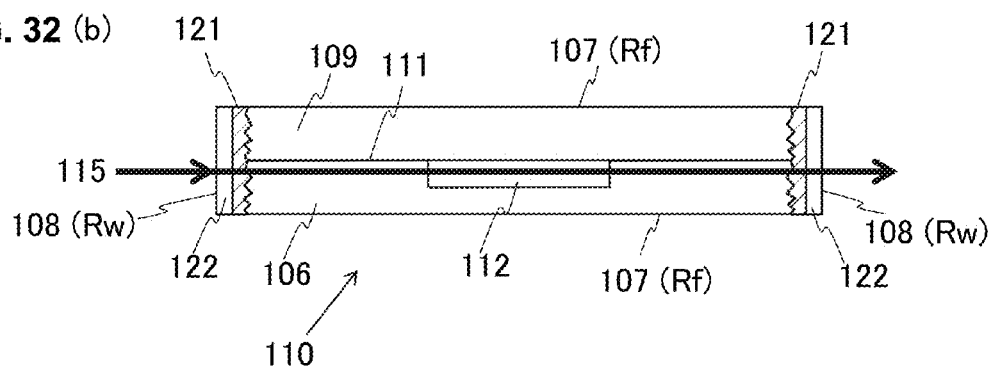

In the means shown in FIG. 32(*a*), similar to FIG. 31(*a*), the microchip 110 may be fabricated by pasting the glass window to the side face 108 of the recessed shape resin substrate 106 without pasting to the side face 108 of the flat shape resin substrate 109. Further, there is also a case where the side face 108 is not necessarily vertical to the front face 108, but is inclined thereto. In such a case, similar to FIGS. 31(*b*) and 31(*c*), the microchip 110 maybe fabricated by pasting the glass window to the inclined side face 108. Thereby, when the surface roughness of the side face 108 is similarly reduced, similarly to FIGS. 31(*b*) and 31(*c*), if an inclination of the center axis of the laser beam 115 before being incident on the microchip is controlled in consideration of the refraction at the side face 108, the channel 112 can be irradiated by a strong laser intensity from a desired direction while avoiding laser scattering on the side face 108.

[Sixth Embodiment]

According to the present embodiment, the surface roughness shown in the fifth embodiment is shown more quantitatively. A microchip having a material of ZEONOR was fabricated by the injection molding. As shown by a front view in FIG. 33, a size of a front face of the microchip 110 is made to be 20 mm×90 mm, and a thickness thereof was made to be 1.5 mm. Only one channel 112 having a section of 40 μm square was provided at an inner portion of the microchip. An inlet port 123 and an outlet port 124 are provided at both ends of the channel 112. Both of front faces of the microchip were smooth, and brought into a smooth surface. ZEONOR is optically transparent, and therefore, an object disposed on an opposed side by interposing the front faces of the microchip was brought into a state of being seen through. In contrast thereto, neither of side faces of the microchip was smooth, and neither was brought into a smooth surface. Since a surface of the side face was smoked, and therefore, an object disposed on an opposed side by interposing the side faces of the microchip could not be seen.

FIG. 34 respectively shows images (images of an area of height 212 μm×width 283 μm) observing respectively the side face and the front face of the microchip by using an object lens having 100 magnification of a laser microscope (KEYENCE CORPORATION, VK-8700), and a surface roughness RMS derived from the images. Here, as the surface roughness RMS, the surface roughness RMS in an arbitrary height 50 μm×width 50 μm area was calculated in the area of height 212 μm×width 283 μm described above, and the surface roughness RMS was indicated by a minimum value thereof. The surface roughness calculated in this way, for excluding an influence of a particular flaw or dirt. Here, the size of height 50 μm×width 50 μm was set so as to substantially align with a diameter of an introduced laser beam. As is apparent from the laser microscope image, it is found that whereas the front face is smooth, the side face is roughened. Whereas the surface roughness of the side face was as large as 0.44 μm, the surface roughness of the front face was 0.07 μm, 6 times as small.

FIG. 35 shows surface observation images of the laser microscope and surface roughness RMS of the side faces of the microchips under various conditions, showing that the side faces are brought into an untreated state (data the same as that of the side face of FIG. 34), a state of grinding the side face by emery paper, a state of grinding the side face by a diamond paste, and a state of adhering a glass window to the side face. Here, the glass window was fabricated by cutting a slide glass (Matsunami, S1111) by 3 mm square.

Figure 28:
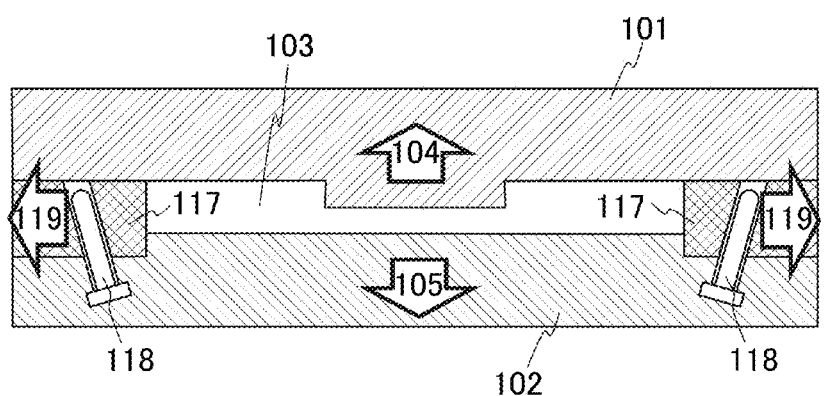
FIGS. 28(a) to 28(c) show explanatory views indicating a procedure of fabricating a microchip made of resin by injection molding.
Figure 28:
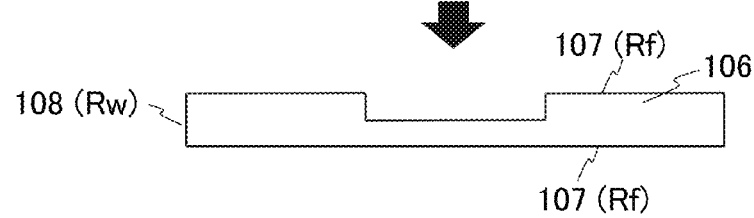
Figure 28:
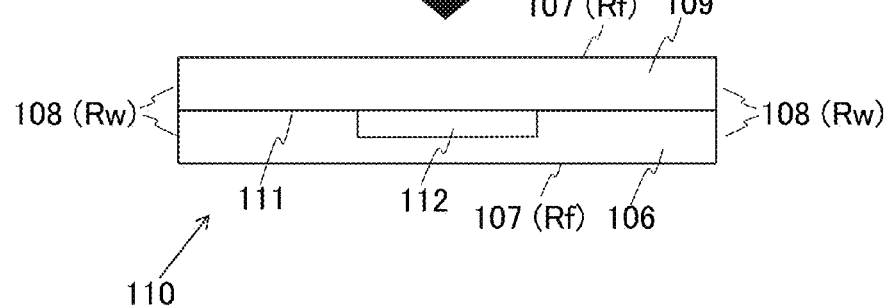

It was found from the surface observation image that the surface was further smoothed in the above-described order, and it was found that the surface roughness RMS was successively small such that 0.44 μm, 0.24 μm, 0.14 μm, and 0.06 μm, respectively, in correspondence therewith. A method of deriving the surface roughness RMS is similar to that of FIG. 34. Also the roughness of the front face of the microchip was 0.07 μm as shown in FIG. 34, which was equivalent to the surface roughness 0.06 μm of the side face adhered with the slide glass as shown in FIG. 35, and therefore, it could be confirmed again that the front face of the microchip was brought into a smooth surface. This signifies that the side face 108 can be brought into the smooth surface at a stage after the injection molding by using the method as shown in FIGS. 28(*a*) and 28(*b*). Further, the surface roughness obtained by the emery paper grinding and the diamond paste grinding in this case show only a result of grinding by an unskilled person manually, and when a skilled person carries out grinding, or the grinding is carried out by using a machine, the surface roughness can be smaller, and a smooth surface equivalent to that of the glass window or higher can naturally be brought about.

Figure 33:
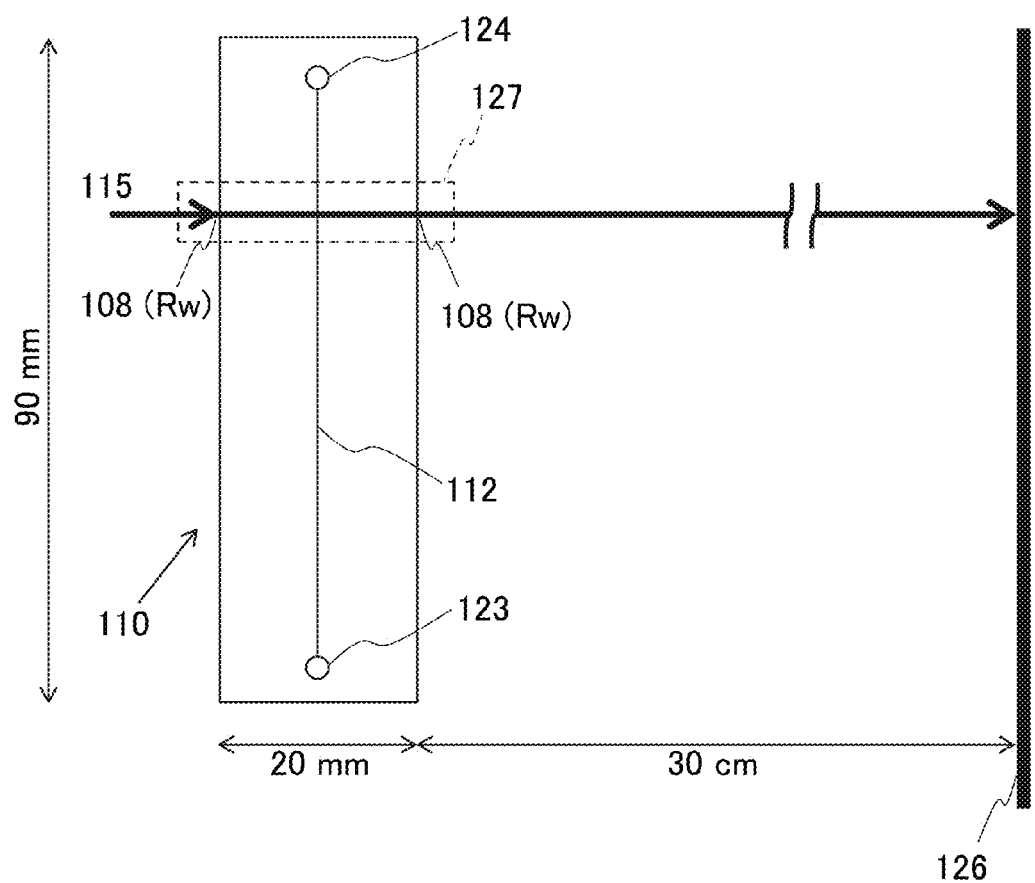
FIG. 33 is a diagram showing an evaluation experiment system of side-entry laser beams in microchips.

Successively, efficiencies of the beam side-entry irradiation of the microchips having the side faces under various conditions shown in FIG. 35 were evaluated by experiments. FIG. 33 is a figure showing experimental methods. However, a contraction scale display of FIG. 33 differs from that of an actual case. A front face view of the microchip 110 configuring a horizontal width 20 mm is shown. The laser beam 115 having a wavelength of 505 nm was introduced substantially vertically from the side face 108 on a left side of the microchip 110 after adjusting a diameter thereof to about 50 μm, and a laser intensity thereof to 14.85 mW, and the laser beam 115 was made to transmit to the microchip 110 having a width 20 mm, and was emitted from the side face 108 on the right side. Here, a position of a center axis of the laser beam 115 in a direction vertical to the front face 107 of the microchip 110 (direction vertical to paper face of FIG. 33) was adjusted such that although the laser beam 115 transmitted through the microchip 110, the laser beam 115 did not irradiate and transmit through the channel 112. This is for persistently evaluating performance of the laser 115 of transmitting the microchip 110 by excluding an influence on laser intensity by irradiating and transmitting the channel 112 by the laser beam 115. As shown in FIG. 36, images observed in a direction vertical to the front face 107 (a direction vertical to paper face of FIG. 33, images of image taking areas 127 as shown in FIG. 33), in which the laser beams 115 transmitted through inner portions of the microchips 110, were acquired by a digital camera. Next, the laser beam 115 emitted from the microchip 110 was made to collide substantially vertically to a screen 126 in a flat plate shape provided at a position remote from the microchip 110 by about 30 cm, and a spot of the laser beam 115 was formed on the screen 126. As shown in FIG. 36, images of the spots observed from a direction oblique to the screen 126 were acquired under respective conditions by the digital camera. The images by the above-described digital camera are acquired through protection glasses for cutting the laser beam to avoid the saturation of the images since in any of cases, intensity of the laser beam images was excessively strong as they were. Further, the laser intensity at a center position of the spot of the laser beam 115 on the screen 126 was measured by a power meter having a sensor area of about 1 cm area.

FIG. 36 summarizes an evaluation result described above. A side face state of untreated, emery paper grinding, diamond paste grinding, and glass window corresponded to respective conditions of FIG. 35. However, here, both of the side face on which the laser beam was incident, and the side face from which the laser beam was emitted were made to be under the same condition. In the respective laser beam transmitting images, similarly to FIG. 33, the laser beam is incident on the microchip from the left side, and emitted from the right side. Here, the images of the laser beams are observed only at portions of transmitting through the inner portions of the microchips, and the images of the laser beams are not observed at the other portions (left and right of the microchips).

In the untreated state, the diameter of the laser beam incident from the side face on the left side of the microchip was enlarged by the laser scattering at the side face as the laser beam advanced through the inner portion of the microchip. The laser beam emitted from the side face on the right side of the microchip was further diverged by the laser scattering at the side face, and formed a broad spot on the screen. The screen is configured by a shape of a black plate as shown in FIG. 36. A laser intensity at a center position of the spot was only 0.17 mW and a rate thereof as compared with the laser intensity 14.85 mW before being incident on the microchip (hereinafter, referred to as transmittance of laser beam) was only 1%. It was apparent that the laser beam scattering at the side face was restrained, and transmitting performance was improved in accordance with a reduction in the surface roughness of the side face from the untreated state, to the emery paper grinding, the diamond paste grinding, and the glass window. In a state of the diamond paste grinding, a clear spot was formed on the screen, and the transmittance of the laser beam was improved to 38%. Further, in the state of the glass window, similarly to a case where the microchip is not present, a sharp spot was formed on the screen, and the transmittance of the laser beam reached 72%. Further, in the state of the glass window, the diameter of the laser beam advancing through the inner portion of the microchip was not enlarged, and about 50 μm before incidence was maintained.

Figure 37:
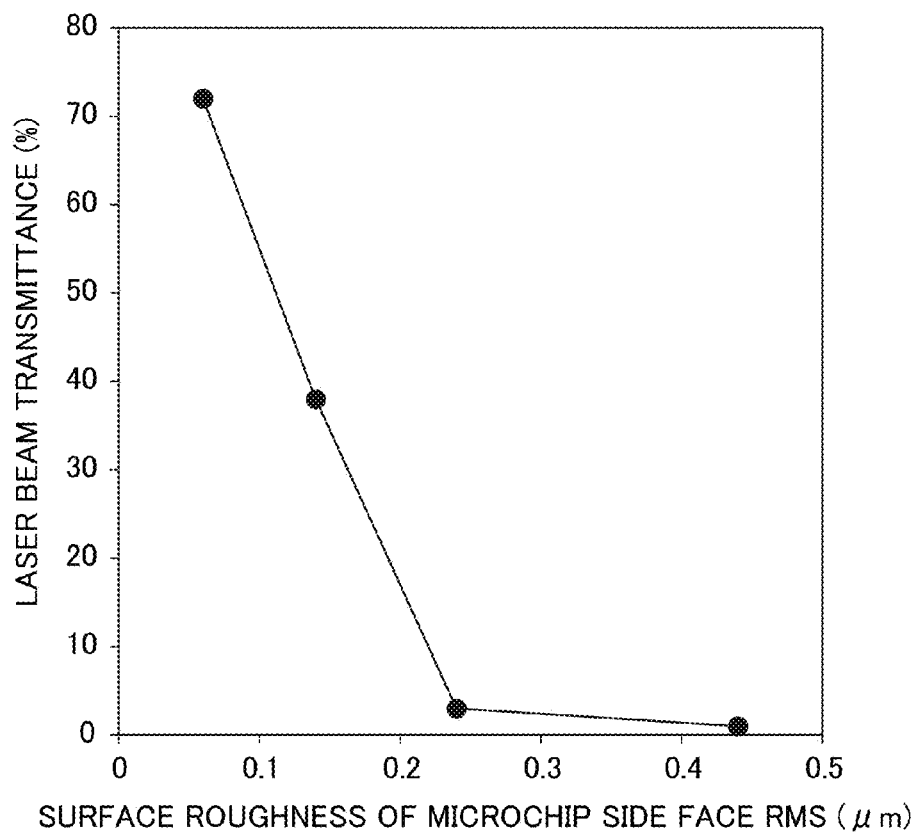
FIG. 37 is a diagram showing a relationship between surface roughness of side faces of microchips and transmittance of side-entry laser beams.

FIG. 37 expresses a relationship between the surface roughness RMS of the side face of the microchip and the transmittance of the laser beam obtained from results of FIG. 35 and FIG. 36. It was found from the results that there was an extremely high correlation between the surface roughness of the face on which the laser beam was incident, and the surface from which the laser beam was emitted and the laser beam transmittance. It was apparent that the smaller the surface roughness, that is, the smoother the surface and the nearer the surface to the smooth surface, the more improved the transmittance of the laser beam, as a result, scattering of the laser beam at the side faces was restrained, an intensity of the laser reaching a single or plural channel(s) at the inner portion of the microchip was increased, and highly sensitive fluorescence detection at the respective channels could be carried out. It was found from the result of FIG. 37 that although the smaller the surface roughness, the better, it was effective to make the surface roughness equal to or smaller than 0.24 μm in the RMS particularly. It was found that, further preferably, the surface roughness of the RMS was made to be equal to or smaller than 0.1 μm. Further, it was found that a significant improvement was achieved in the transmittance of the laser beam by reducing to smooth a surface of an arbitrary surface state at least by 0.1 μm in the RMS.

States of a side face and a front face after fabricating a microchip shown in FIG. 34 show only examples. Respective surface roughnesses are naturally changed by a method fabricating a microchip. The fabricating method is not limited to a method of using a mold of the injection molding or the like, and there is also a case of carrying out machining after the injection molding. According to other example of fabricating a microchip by the injection molding, the surface roughness RMS was 0.08 μm at the front face and 0.41 μm at the side face. Further, according to the other example of fabricating a microchip by the injection molding, the surface roughness RMS was 0.11 μm at the front face, and 1.37 μm at the side face. However, even when a microchip is fabricated by any of the methods, tendencies shown in FIGS. 34 through 37 are common. That is, the surface roughness of the side face is larger than the surface roughness of the front face, laser scattering at the side face is reduced by smoothing at least a portion of the side face, the laser beam introduced from the side face is made to reach a channel at an inner portion of the microchip by a strong intensity, and highly sensitive fluorescence detection can be carried out at the channel.

[Seventh Embodiment]

Figure 38:
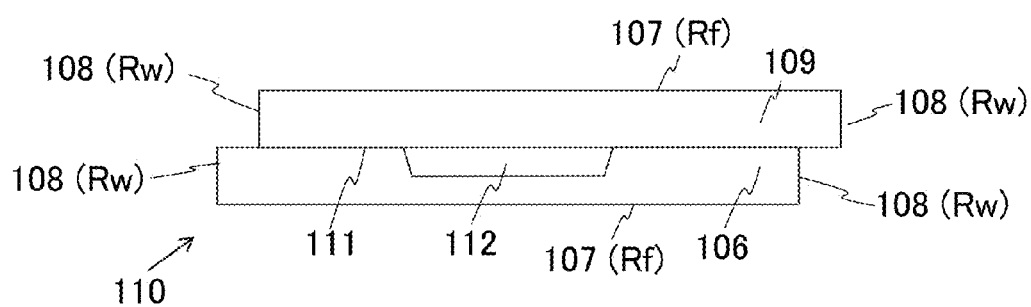
FIG. 38 is a view showing an example of a level difference on a side face of a microchip at lamination surface position.

There was a case of bringing about a next new problem in addition to the problem of the surface roughness of the side face shown in the fifth embodiment and the sixth embodiment described above. FIG. 38 shows a sectional view of the microchip 110 in a case where the recessed shape resin substrate 106 and the flat shape resin substrate 109 are pasted together in a state of deviating respective side faces 108 in a direction in parallel with the front face 107, and a level difference is brought about between the two side faces. There is a case which the level difference is brought about by an error in pasting, and there is also a case of bringing about the level difference intentionally. Although FIG. 38 shows a case where horizontal widths of the recessed type resin substrate 106 and the flat shape resin substrate 109 are equal, there is also a case where the horizontal widths differ from each other before pasting the substrate. Such a case necessarily brings about a similar level difference.

Figure 39:
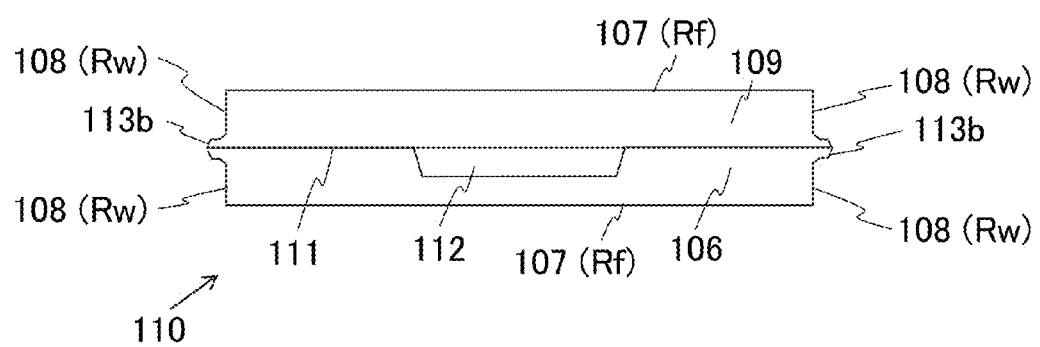
FIG. 39 is a view showing an example of a buildup on a side face of a microchip at lamination surface position.
Figure 40:
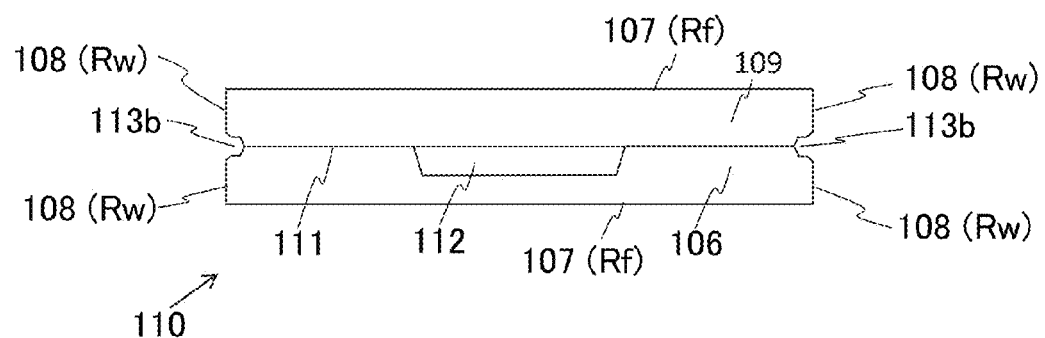
FIG. 40 is a view showing an example of a depression on a side face of a microchip at lamination surface position.

FIG. 39 shows a sectional view of the microchip 110 in a case where a buildup 113a is brought about at a portion of the lamination surface 111 on the side face 108 in the step of pasting together the recessed shape resin substrate 106 and the flat shape resin substrate 109. FIG. 40 shows a sectional view of the microchip 110 in a case where a depression 113b is brought about at a portion of the lamination surface 111 on the side face 108 inversely to FIG. 39. It seems that these were brought about while deforming corners of the recessed shape resin substrate 106 and the flat shape resin substrate 109 before being pasted together, or by being influenced by a pressure or heat at the pasting step.

Figure 27:
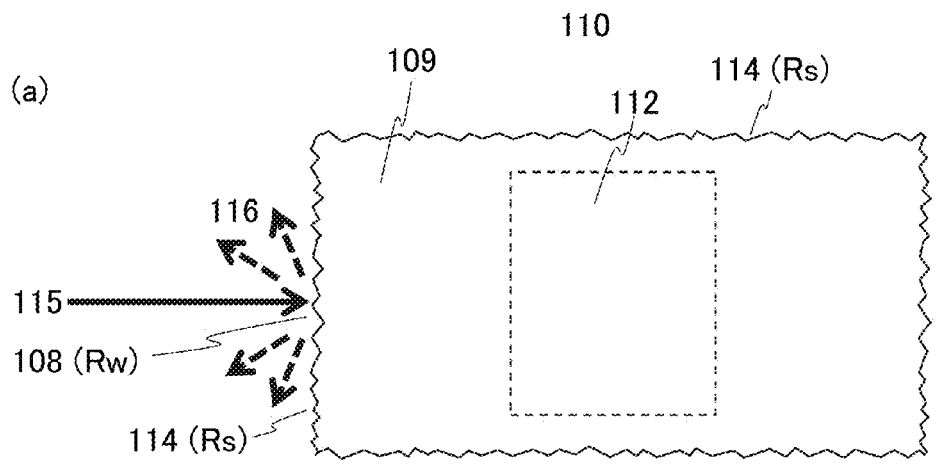
FIGS. 27(a) and 27(b) show explanatory views indicating a laser scattering by a surface roughness of a side face of a microchip.
Figure 27:
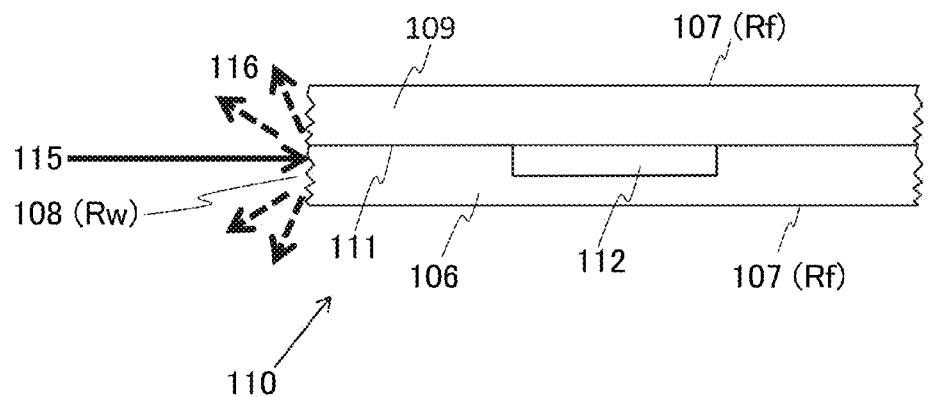

Although the above-described is brought about simultaneously with a problem of the large surface roughness of the side face 108 as shown in FIGS. 27(*a*) and 27(*b*), according to the present embodiment, a case where the surface roughness of the side face 108 is small is considered (FIG. 38 through FIG. 40 are shown also in such a way).

As has been explained above, it is a conventional common sense that in a case where the laser beam is made to be horizontally incident on a microchip having single or plural channel(s), a center axis of the laser beam is made to be in parallel with the front face 107, the lamination surface 111, and the array plane in a case of arranging the plural channels. That is, when a distance between the center axis of the laser beam and the lamination surface 111 is made to be x, and a depth of the channel 112 (a width of the channel 112 in a direction vertical to the lamination surface 111) is made to be y, x=y/2. On the other hand, when a width of the laser beam irradiating the channel 112 is made to be φ, in a case of carrying out highly sensitive fluorescence detection, although it is preferable to configure φ≈y, actually, frequently, φ≥y is configured. Further, although φ is defined by a width by which a laser intensity is $1/e^2$ (13.5%) of a peak value, a laser intensity smaller than the above laser intensity is present by a width higher than 100. That is, a portion of the laser beam is overlapped at a position of intersecting the side face 108 and the lamination surface 111. Therefore, when the side face 108 is brought into a state of any of FIG. 38 through FIG. 40 (level difference, buildup, or depression), the laser beam is scattered considerably at the side face 108, and a laser having a sufficient intensity cannot be made to reach the channel 112. Hence, a description will be successively given to three resolution schemes for FIG. 38 through FIG. 40.

Figure 41:
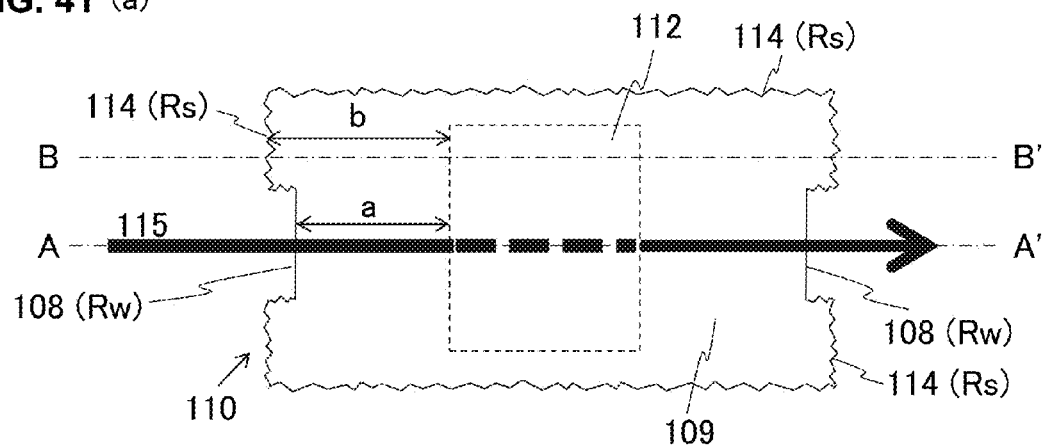
FIGS. 41(a) to 41(c) show views indicating an example of irradiating a laser beam to a part of a microchip side face where is machined and smoothed.
Figure 41:
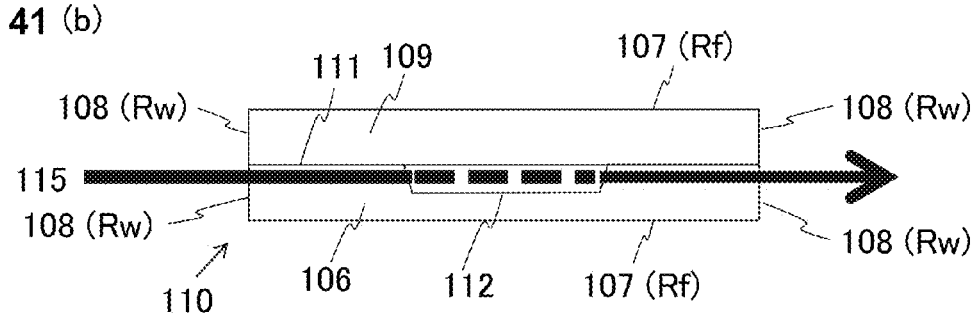
Figure 41:
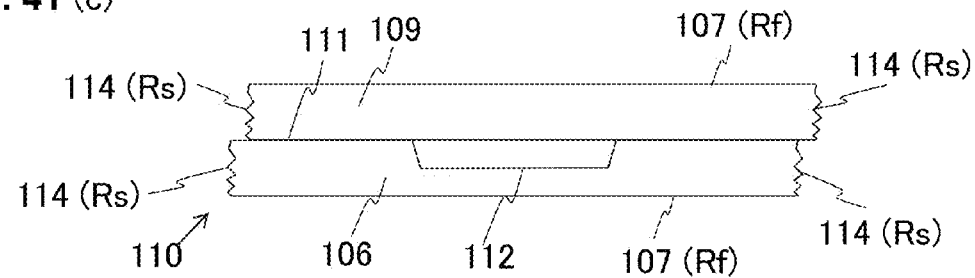

FIGS. 41(*a*) to 41(*c*) show a first resolution scheme. Whereas in FIGS. 29(*a*) and 29(*b*) and FIGS. 30(*a*) and 30(*b*), the side face 108 was ground for the microchip 110 which has been pasted together, a structure more depressed to an inner side than the surrounding was configured by subjecting the side faces 108 on which the laser beam 115 was incident and from which the laser beam 115 was emitted to machining and grinding. That is, as shown in the front face of FIG. 41(*a*), when a distance between the side face 108 subjected to machining and grinding and the channel 112 is a, and a distance between the side face 114 which is not subjected to machining and grinding and the channel 112 is b, a<b, and it is a characteristic to provide a machining distance c=b−a>0. Here, assume a case where the side face 108 before being subjected to machining and grinding and the side face 114 are respectively substantially in parallel with the side face of the channel 112. In a case where these are not in parallel with each other, a and b described above are not defined, but only a machining distance c of the side face 108, that is, a distance between the side face 108 after having been subjected to machining and grinding and the side face 114 is defined. c may be larger than a size of the level difference, the buildup, or the depression in FIG. 38 through FIG. 40, and it is preferable that c is at least equal to or larger than 5 μm, preferably equal to or larger than 50 μm.

As a result as described above, as shown in an AA' sectional view of FIG. 41(*b*), at a section of the side face 108 on which the laser beam 115 was irradiated, the level difference, the buildup, or the depression was resolved on the side faces 108 of the recessed shape resin substrate 106 and the flat shape resin substrate 109, further, the surface roughness Rw was small, and therefore, scattering of the laser beam 115 at the side face 108 is reduced, and a laser beam having a strong intensity could be made to reach the channel 112. On the other hand, as shown in a BB' sectional view of FIG. 41(*c*), at a section of the side face 114 on which the laser beam 115 was not irradiated, the level difference, the buildup, or the depression remained on the side faces of the recessed shape resin substrate 106 and the flat shape resin substrate 109, (in FIG. 41(*c*), a case where the level difference remains was illustrated), and a state in which the surface roughness Rs stayed to be large was brought about. In this way, in the side faces, only the side faces 108 of portions on which the laser beam 115 is incident and from which the laser beam 115 is emitted are machined and ground by which the above-described problem is resolved, and the microchip is made to be able to fabricate at low cost.

Figure 46:
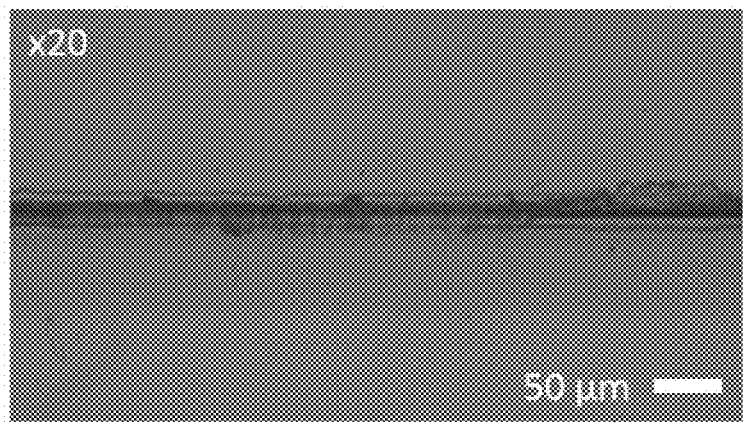
FIGS. 46(a) and 46(b) show diagrams indicating examples of optical microscope images of a microchip side face with a buildup at lamination surface position, and the microchip side face where the buildup was removed by machining and grinding.
Figure 46:
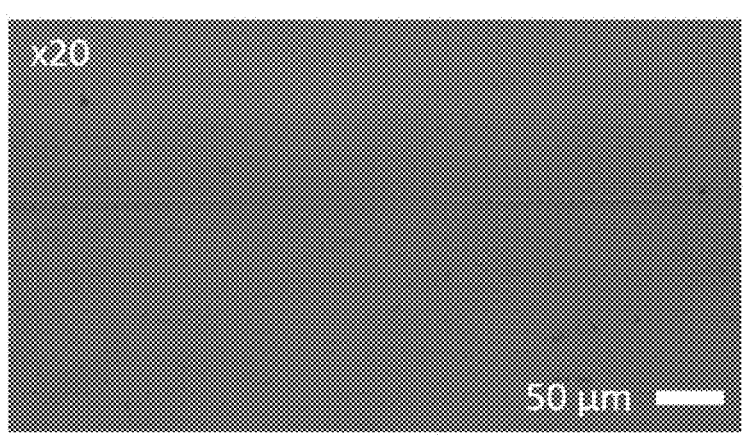

FIGS. 46(*a*) and 46(*b*) show an actual example of the microchip 110 in a case where the buildup 113*a* is brought about at a portion of the side face 108 intersecting with the lamination surface 111 of the recessed shape resin substrate 106 and the flat shape resin substrate 109 as shown in FIG. 39, and a case where the side face 108 is machined and ground as shown in FIGS. 41(*a*) to 41(*c*). FIG. 46(*a*) shows an image observed by an optical microscope (object lens× 20) from a side face direction. A bold straight line extended in a horizontal direction at a center of FIG. 46(*a*) expresses a buildup along the lamination surface. An upper side of the bold straight line indicates the side face of the flat shape resin substrate, and a lower side thereof indicates the side face of the recessed shape resin substrate. The buildup described above was brought about at a step of pasting together the two substrates, and was provided with a size of about 50 μm in a direction vertical to the lamination surface (longitudinal direction of FIG. 46(*a*)), and a size of about 50 μm in a direction vertical to a side face (a direction vertical to paper face of FIG. 46(*a*)). This significantly hampers an introduction of the laser beam from the side face. FIG. 46(*b*) is an optical microscope observation image of the side face which is ground to be a smooth surface by machining the side face by about 100 μm by a grinding stone attached to the grinder. Although a line extended thinly in a horizontal direction at a center of FIG. 46(*b*) indicates the lamination surface, an influence thereof is inconsiderable, and an efficient introduction of the laser beam could be carried out by avoiding scattering of the laser beam at the side face.

Figure 42:
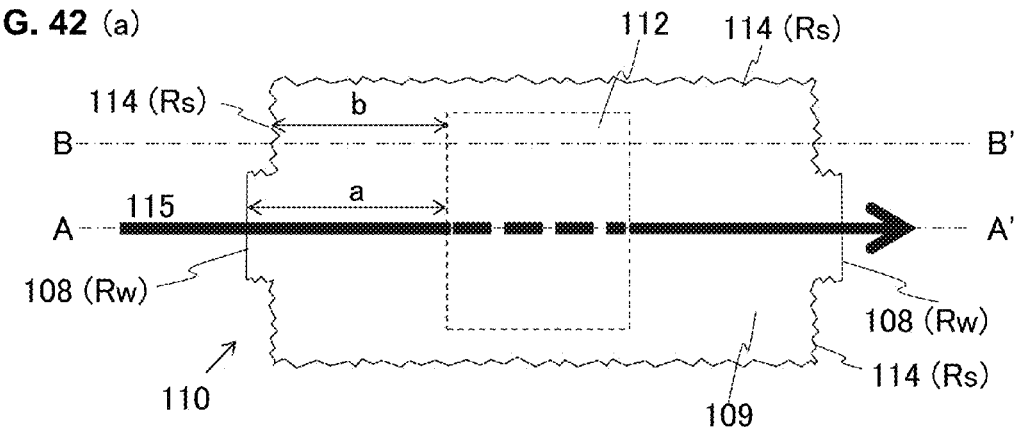
FIGS. 42(a) to 42(c) show views indicating an example of irradiating a laser beam to a part of a microchip side face where is accumulated with a transparent substance and smoothed.
Figure 42:
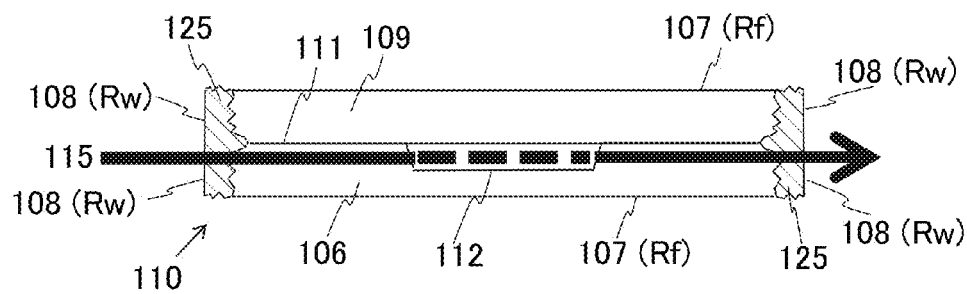
Figure 42:
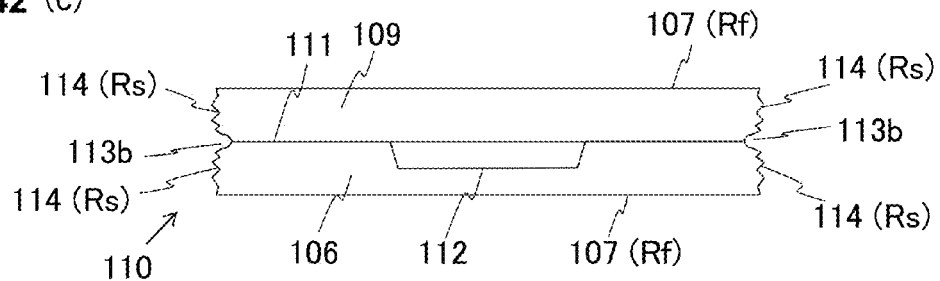

FIGS. 42(*a*) to 42(*c*) show a second resolution scheme. For a microchip which has been pasted together, a structure of being projected to an outer side more than the surrounding was configured by accumulating a transparent substance 125 of a resin or the like at the side faces 108 on which the laser beam 115 was incident and from which the laser beam 115 was emitted conversely to FIGS. 41(*a*) to 41(*c*), and the side face 108 (a surface of the transparent substance 125 on a side opposed to and in parallel with the side face 108 before accumulating the transparent substance 125) was smoothed. That is, as shown in a front face view of FIG. 42(*a*), when a distance between the side face 108 which is subjected to accumulating and smoothing and the channel 112 is a, and a distance between the side face 114 which is not subjected to accumulating and smoothing the channel 112 is b, a>b, and it is a characteristic that an accumulation distance c=a−b>0 is provided. Here, in this case, the side face 108 before being subjected to accumulating and smoothing and the side face 114 are substantially in parallel with the side face of the channel 112 respectively. In a case where these are not in parallel, a and b described above are not defined, but only the accumulation distance c of the side face 108, that is, a distance between the side face 108 after having been subjected to accumulating and smoothing and the side face 114 is defined. It is preferable that c is larger than a size of the level differences, the buildups, or the depressions in FIG. 38 through FIG. 40, and it is preferable that c is equal to or larger than at least 5 μm, preferably, equal to or larger than 50 μm.

As a result as described above, as shown in an AA' sectional view of FIG. 42(b), at a section of the side face 108 on which the laser beam 115 is irradiated, the level difference, the buildup, or the depression was resolved on the side faces 108 of the recessed shape resin substrate 106 and the flat shape resin substrate 109 (in FIG. 42(b), a case of resolving the depression was illustrated), further, the surface roughness Rw was small, and therefore, scattering of the laser 125 at the side face 108 was reduced, and a laser beam having a strong intensity could be made to reach the channel 112. On the other hand, as shown in a BB' sectional view of FIG. 42(c), at a section of the side face 114 on which the laser beam 115 is not irradiated, the level difference, the buildup, or the depression remains at the side faces 108 of the recessed shape resin substrate 106 and the flat shape resin substrate 109 (in FIG. 42(c), a case where the depression 113 remained was illustrated), and a state in which the surface roughness Rs stays to be large was brought about. In this way, the above-described problem is resolved by accumulating and smoothing only portions of the side faces 108 on which the laser beam 115 is incident and from which the laser beam 115 is emitted in the side faces, and the microchip is made to be able to be fabricated at low cost.

Figure 44:
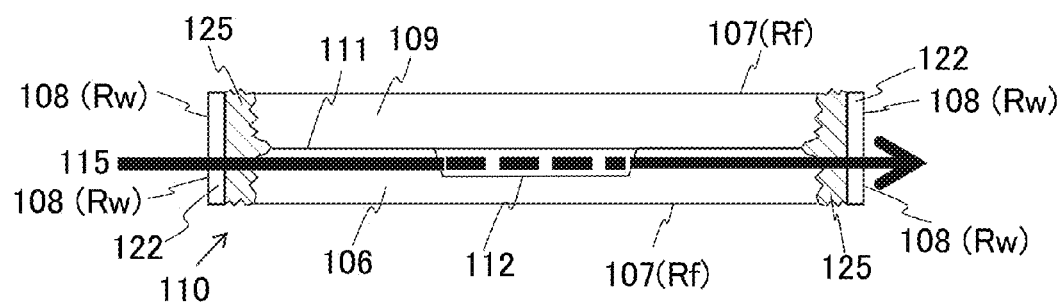
FIG. 44 is a view showing an example of irradiating a laser beam to a part of a microchip side face of a microchip where is accumulated with a transparent substance and pasted with a window.

A resin having a curing property, for example, an adhering agent 121 shown in FIGS. 32(a) and 32(b) may be used for the transparent substance 125 accumulated on the side face 108. In FIGS. 42(a) to 42(c), unlike FIGS. 32(a) and 32(b), the transparent substance 125 resolves not only a reduction in the surface roughness Rw of the side face 108, but any of the level difference, the buildup, or the depression present at the lamination surface 111 of the recessed shape resin substrate 106 and the flat shape resin substrate 109. Further, in order to realize the resolution, there is brought about a characteristic that the accumulation distance c of the transparent substance 125 is larger than a size of the level difference, the buildup, or the depression. Further, as shown in an AA' sectional view of FIG. 44, a transparent plate member smoothing the side face 108 as in the glass window 122 may be pasted on the side face 108 of the transparent substance 125.

Figure 43:
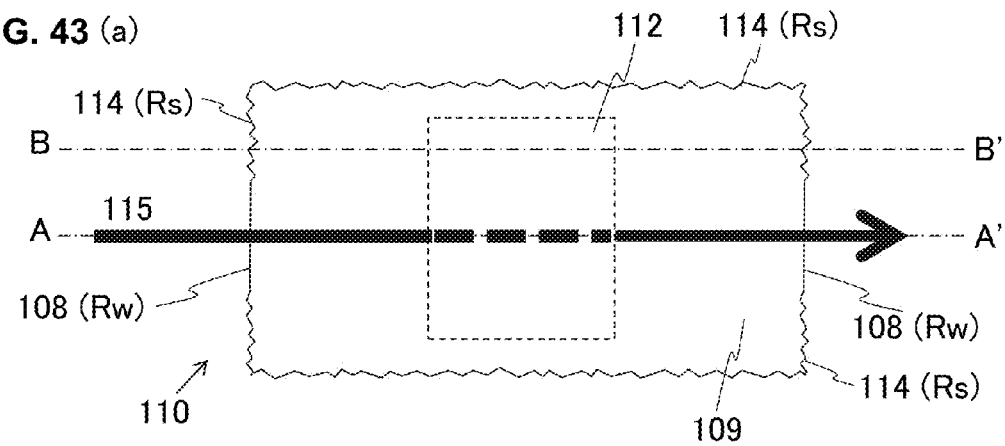
FIGS. 43(a) to 43(c) show views indicating an example of obliquely irradiating a laser beam to a part of a microchip side face where is smoothed.
Figure 43:
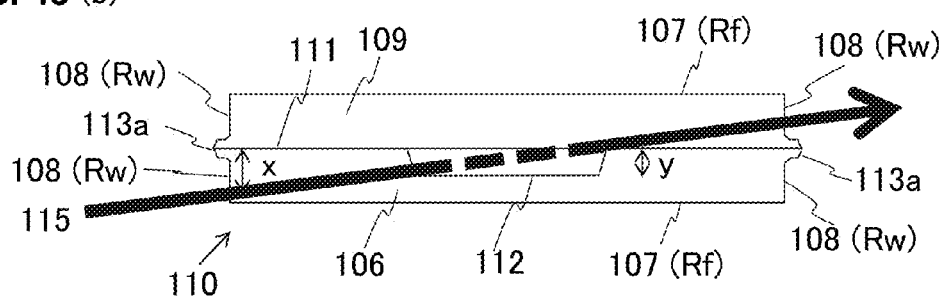
Figure 43:
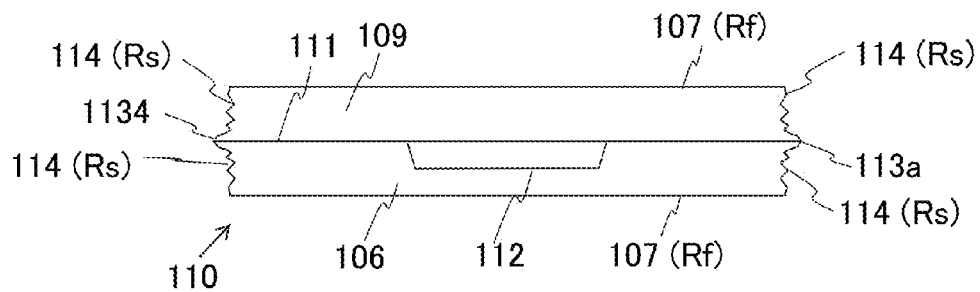

FIGS. 43(a) to 43(c) shows a third resolution scheme. FIG. 43(a) is a front view, FIG. 43(b) is an AA' sectional view of FIG. 43(a), and FIG. 43(c) is a BB' sectional view thereof. When a distance between a center axis of the laser beam 115 and the lamination surface 121 on the side face 108 was x, and a depth of the channel 112 (a width of the channel 112 in a direction vertical to the lamination surface 111) was y, as described above, conventionally, x=y/2, and the laser beam 125 was irradiated from the side face 108 in parallel with the lamination surface 111 (parallel irradiation). In contrast thereto, in FIGS. 43(a) to 43(c), the laser beam 115 was irradiated from the side face 108 to the microchip 110 which had been pasted together by being inclined to the lamination surface 111 after smoothing the side face 108 (oblique irradiation).

Thereby, as shown in FIG. 43(b), at a section of the side face 108 on which the laser beam 115 is irradiated, the level difference, the buildup, or the depression present at the side faces 108 of the recessed shape resin substrate 106 and the flat shape resin substrate 109 was avoided when the laser beam 115 is irradiated on the side face 108 (in FIG. 43(b) middle stage (b), a case of avoiding a buildup was illustrated), further, the surface roughness Rw was small, and therefore, scattering of the laser beam 115 at the side face 108 was reduced, and a laser having a strong intensity could be made to reach the channel 112. In a case where a width of the laser beam was 100=y, conventionally, in x=y/2 (parallel irradiation), a laser intensity of $1/e^2$ (13.5%) was present at a position of intersecting the side face 108 and the lamination surface 111, and therefore, a scattering intensity thereof could not be disregarded. In contrast thereto, when x>3*y/4 (oblique irradiation) is configured, the above laser intensity is made to be equal to or smaller than 1%, and can be disregarded substantially. Further, the laser intensity is made to be equal to or smaller than 0.01% by configuring x>y (oblique irradiation).

On the other hand, as shown in FIG. 43(c), at a section of the side faces 114 on which the laser beam 115 is not irradiated, the level difference, the buildup, or the depression remained at the side faces 114 of the recessed shape resin substrate 106 and the flat shape resin substrate 109 (in FIG. 43(c), a case where the buildup 113a remained was illustrated), and a state in which the surface roughness Rs stayed to be large was brought about. In this way, the above-described problem is resolved by smoothing only portions of the side faces 108 on which the laser beam 115 is incident and from which the laser beam 115 is emitted in the side faces, and the microchip is made to be able to be fabricated at low cost. Although in FIG. 43(c), the laser beam 115 is made to be incident from the side face 108 of the recessed shape resin substrate 106, a similar effect is achieved even when the laser beam 115 is incident from the side face 108 of the flat shape resin substrate 109. However, also in this case, a condition of x>3*y/4, or x>y is complied with.

Figure 45:
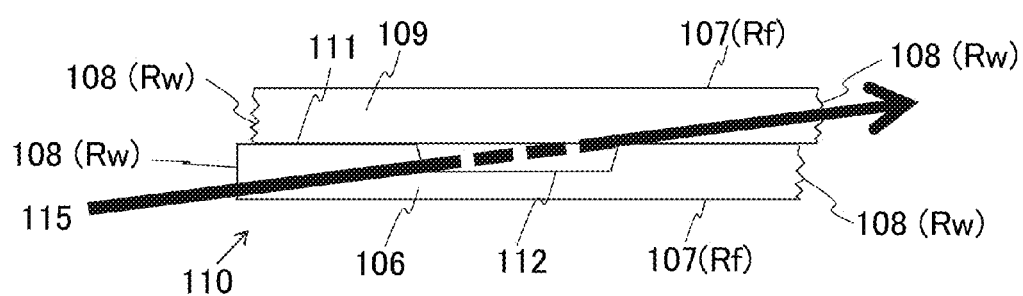
FIG. 45 is a view showing an example of obliquely irradiating a laser beam to a part of one side substrate of a microchip where is smoothed.

FIG. 45 shows a modified example of FIGS. 43(a) to 43(c). FIG. 45 is a view in correspondence with an AA' sectional view of FIG. 43(a). Although in FIG. 43(b), any of the surface roughness Rw of the side faces 108 on both left and right sides of the recessed shape resin substrate 106, and the side faces 108 on both left and right sides of the flat shape resin substrate 109 is reduced and smoothed, it is not necessarily needed to smooth all of the four portions. For example, in FIG. 45, only the side face 108 on the left side of the recessed shape resin substrate 106 on which the laser beam 115 is incident is smoothed. Further, in FIG. 45, a case of bringing about level difference at the recessed type resin substrate 106 and the flat type resin substrate 109 is illustrated. Scattering of the laser beam is restrained also by such a method, further, fabrication of the microchip 110 can be simplified and cost thereof can be made to be low.

Although in the embodiment described above, thicknesses of the recessed shape resin substrate 106 and the flat shape resin substrate 109 are illustrated substantially equally, generally, there is also a case where the thicknesses are not equal. For example, there is a case where the flat shape resin substrate 109 is thinner than the recessed shape resin substrate 106, and is configured by a film-like shape. It is comparatively difficult to smooth a side face of such a thin substrate, and therefore, a method of smoothing one of the side faces of the substrates is more effective as shown in FIG. 45.

As described above, although a case of subjecting the both side faces on the ingoing side and on the outgoing side of the laser beam to a treatment of machining, accumulating, smoothing or the like was mainly shown, there is a case where the treatment is not necessarily needed concerning the side face of the outgoing side. Further, although the number of the channel 112 configured in the microchip 110 was single, the similar effect can naturally be achieved by the same means even in a case of the plural channels 112.

[Eighth Embodiment]

As described above, when fluorescence is detected highly sensitively by irradiating the laser beam to the channel, if a laser beam diameter is made to be to a degree the same as that of, or larger than the channel depth, the laser beam is efficiently irradiated to an inner portion of the channel effectively by aligning the laser beam center axis with the channel center. Ordinarily, the lamination surface and the two front faces of the microchip are in parallel with each other, and also a center axis of the laser beam introduced from the side face is in parallel with these. When the laser beam diameter is made to be φ, a distance between the lamination surface on the side face of the microchip and the laser beam center axis is made to be x, and a depth of each channel is made to be y, the above-described is expressed as φ≥y, x=y/2.

However, at this time, at least a portion of the laser beam transmits through a lamination surface (a face between the flat shape resin substrate and the recessed shape resin substrate configuring the microchip made of resin), and therefore, depending on a situation of finishing the lamination surface, it was apparent that the laser beam was scattered when the laser beam was transmitted through the lamination surface. Although when the flat shape resin substrate and the recessed shape resin substrate are formed completely by the same quality and are homogeneous at the lamination surface, the scattering cannot be brought about, at an ordinary pasting step, mixing of air bubbles or a change in a density is brought about at a vicinity of the lamination surface. That is, although scattering of the laser beam at the side face of the microchip is avoided, the laser beam scattering is independently generated at the lamination surface of an inner portion of the microchip, as a result, an intensity of a laser reaching the channel was considerably attenuated, and a problem of reducing fluorescence detection sensitivity of the channel was posed. Further, there is a case where the lamination surface is bent by a strain in the injection molding or the pasting step, and in such a case, it was found that the laser beam scattering at the lamination surface in an inner portion of the microchip described above was further increased.

According to the present embodiment, means for resolving the problems is proposed without considerably increasing cost or labor of fabricating a microchip. A center axis of the laser beam is made to be remote from the lamination surface more than in an ordinary case for reducing the laser beam scattering at the lamination surface in the inner portion of the microchip. Thereby, transmission of the laser beam through the lamination surface can be avoided before reaching the channel, or at least a degree or a rate of the transmission can be reduced.

Figure 47:
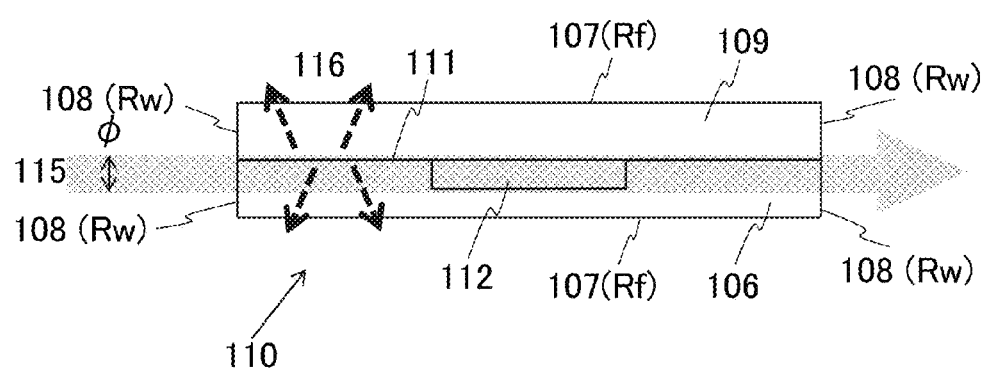
FIG. 47 is an explanatory view showing an example of laser scattering at a lamination surface of a microchip.

FIG. 47 shows a state in which even in a case of smoothing the side face 108 of the microchip 110, depending on a state of the lamination surface 111 pasting together the flat shape resin substrate 109 and the recessed shape resin substrate 106, the laser beam 115 incident on the inner portion of the microchip is subjected to the laser scattering 116 in transmitting through the lamination surface 111, as a result, an intensity of the laser reaching the channel 112 is reduced.

Although in respective drawings until this paragraph, only the center axis of the laser beam 115 is shown, in FIG. 47 through FIG. 50(b), the laser beam 115 is shown by a size near an actual diameter. In FIG. 47, φ≈y is configured, and the center axis of the laser beam 115 is introduced from the side face 108 in parallel with the front face 107. At this time, a distance x between the lamination surface 111 (or a plane extending the lamination surface 111) on the side face 108 of the microchip 110 and the laser beam center axis is x≈y/2. At this time, at least a portion of the laser beam 115 transmits through the lamination surface 111, and the laser scattering 116 is brought about depending on a situation of finishing the lamination surface.

Figure 48:
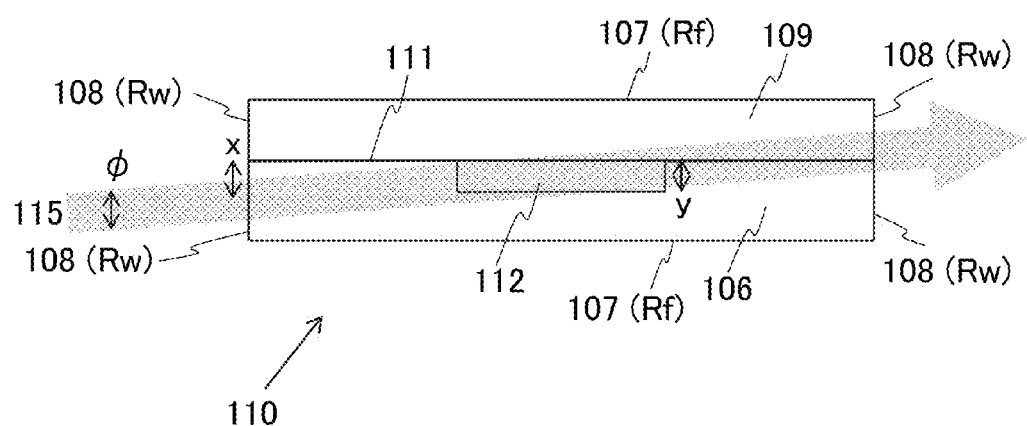
FIG. 48 is a view showing an example of obliquely irradiating a laser beam to a side face of a microchip.

FIG. 48 shows means for avoiding or reducing the laser scattering 116 shown in FIG. 47. A state is shown in which a distance between the laser beam center axis and the lamination surface 111 on the side face 108 of the microchip 110 is increased at the inner portion of the microchip 110 by configuring x>y/2, further preferably, by configuring x>y, and therefore, the transmission of the laser beam 115 through the lamination surface 111 is avoided or reduced at an interval from the side face 108 until reaching the channel 112. At this time, as shown in FIG. 48, the center axis of the laser beam is not made to be in parallel with the front face 107 and the lamination surface 111 for aligning the laser beam center axis with the channel center. As a result, an intensity of a laser reaching the channel 112 can be increased, and fluorescence can be detected highly sensitively at the channel 112.

Figure 49:
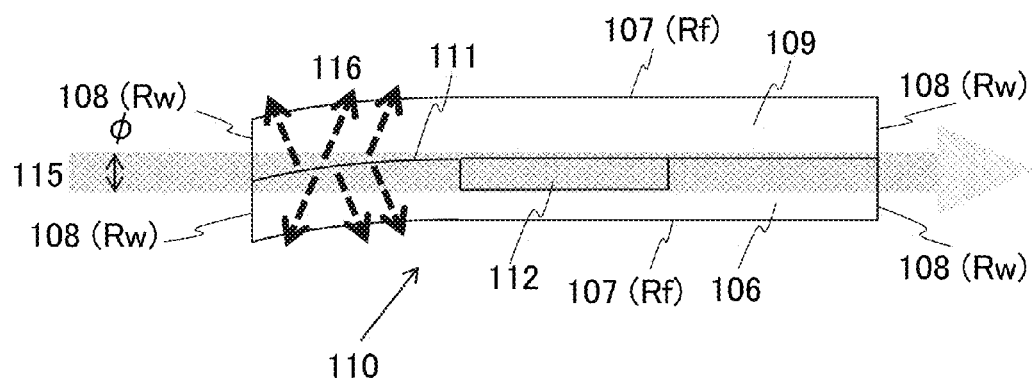
FIG. 49 is an explanatory view showing an example of laser scattering at a lamination surface of a microchip which is curved.
Figure 50:
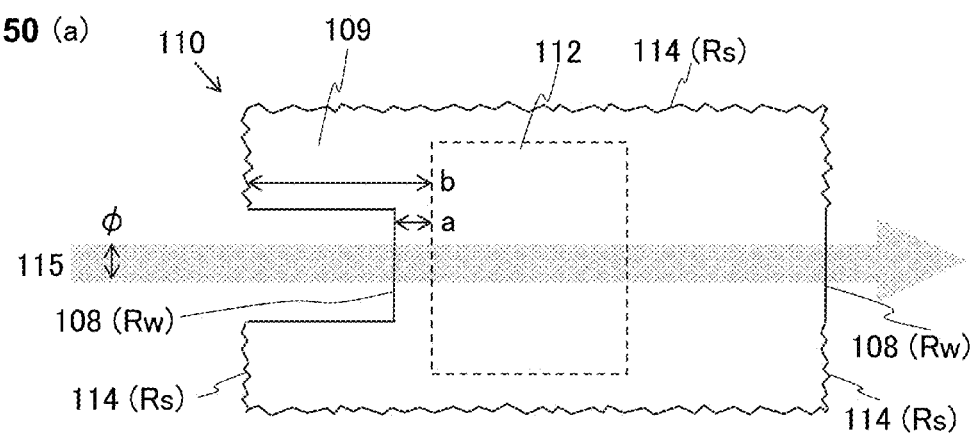
FIGS. 50(a) and 50(b) show explanatory views indicating an example of irradiating a laser beam to a part of a microchip side face where is machined and smoothed.
Figure 50:
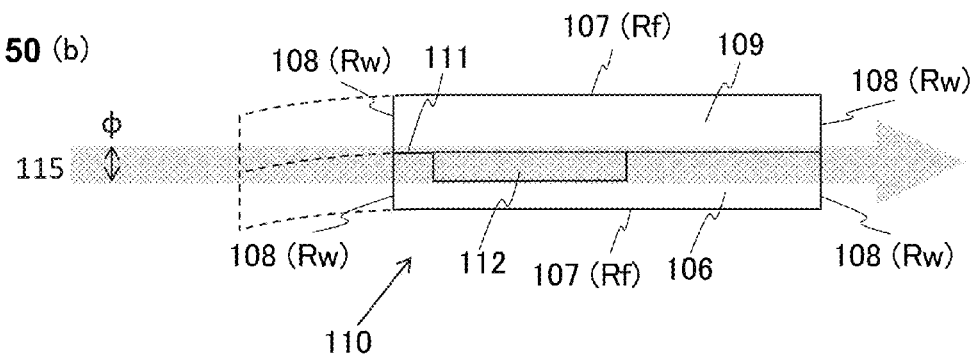

FIG. 49 shows a state in which even in a case of smoothing the side face 108 of the microchip 110, the laser scattering 116 is brought about when the laser beam 115 incident on the inner portion of the microchip 110 transmits through the lamination surface 111 by bending the lamination surface 111 of pasting together the flat shape resin substrate 109 and the recessed shape resin substrate 106, as a result, the intensity of the laser reaching the channel 112 is reduced.

FIGS. 50(a) and 50(b) show means for avoiding or reducing the laser scattering 116 shown in FIG. 49. FIG. 50(a) shows a front view of the microchip 110, FIG. 50(b) shows a cross-sectional view thereof including the laser beam 115. As shown in FIGS. 50(a) and 50(b), a distance between the side face 108 and the channel 112 is shortened by partially machining a neighboring area of a position of the laser beam irradiation on the side face 108, and the area as a result thereof is smoothed by any means described above. On the other hand, in FIG. 50(a), areas on an upper side and a lower side of the side face 108 are not machined, that is, a distance between the side face 114 and the channel 112 is not shortened. That is, when a distance between the side face 108 and the channel 112 is a, and a distance between the side face 114 and the channel 112 is b, a<b is configured. Such a configuration is constructed for totally maintaining a mechanical strength of the microchip 110, ensuring an easiness of handling, or maintaining a function present at areas on an upper side and a lower side of the side face 108. Here, a case where the side face 108 before being subjected to machining and the side face 114 are respectively substantially in parallel with the side face of the channel 112. In a case where these are not in parallel with each other, a and b described above are not defined, and only a machining distance c of the side face 108, that is, a distance between the side face 108 and the side face 114 after machining is defined.

By constructing the configuration described above, as shown in FIGS. 50(a) and 50(b), the transmission of the laser beam 115 through the lamination surface 111 between the side face 108 and the channel 112 can be avoided or reduced. As a result, an intensity of the laser reaching the channel 112 can be increased, and highly sensitive fluorescence detection at the channel 112 can be carried out. In FIGS. 41(a) to 41(c), it was made to be preferable by configuring the machining distance c=b−a>0, and at least c≥5 μm, preferably, c 50 μm. In contrast thereto, in FIGS. 50(a) and 50(b), it was found by an experiment that it was preferable to configure c≥10 mm, and a≤10 mm.

Although as described above, c=b−a>0 was realized by machining a portion of the microchip, c=b−a>0 may be realized by a method other than machining. In such a case, c is defined not as a machining distance, but as a recessing distance. For example, the flat shape resin substrate 109 and the recessed shape resin substrate 106 shown in FIGS. 50(a) and 50(b), that is, the respective substrates satisfying c=b−a>0 may be fabricated at a stage of the injection molding. The side face 108 of the recessed portion may be smoothed in the injection molding, may be smoothed by grinding, or may be smoothed by pasting a glass window.

Although in the description described above, the number of the channel 112 configured by the microchip 110 is single, even in a case of the plural channels 112, a similar effect can naturally be achieved by the same means.

Ninth Embodiment

A microchip having a material of ZEONOR was fabricated by the injection molding. As shown by a front view in FIG. 51, a size of a front face of the microchip 110 was made to be 40 mm×135 mm, and a thickness thereof was made to be 1.5 mm. However, FIG. 51 is not to scale.

15 channels 112 having a section of 40 μm square were arranged in parallel with the front face of the microchip 110 at an inner portion of the microchip 110. The respective channels 112 were provided with individual inlet ports and a common outlet port 124. While an array interval of the respective channels 112 was made to be large at the inlet port 123, the array interval was made to be small at the outlet port 124. An area of illustrating the laser beam 115 was provided at a vicinity of the outlet port 124, and the array interval of the respective channels 112 was made to be 0.2 mm at the area. A width of the 15-channel arrays at the area was made to be 0.2 mm×(15-1)=2.8 mm.

Figure 51:
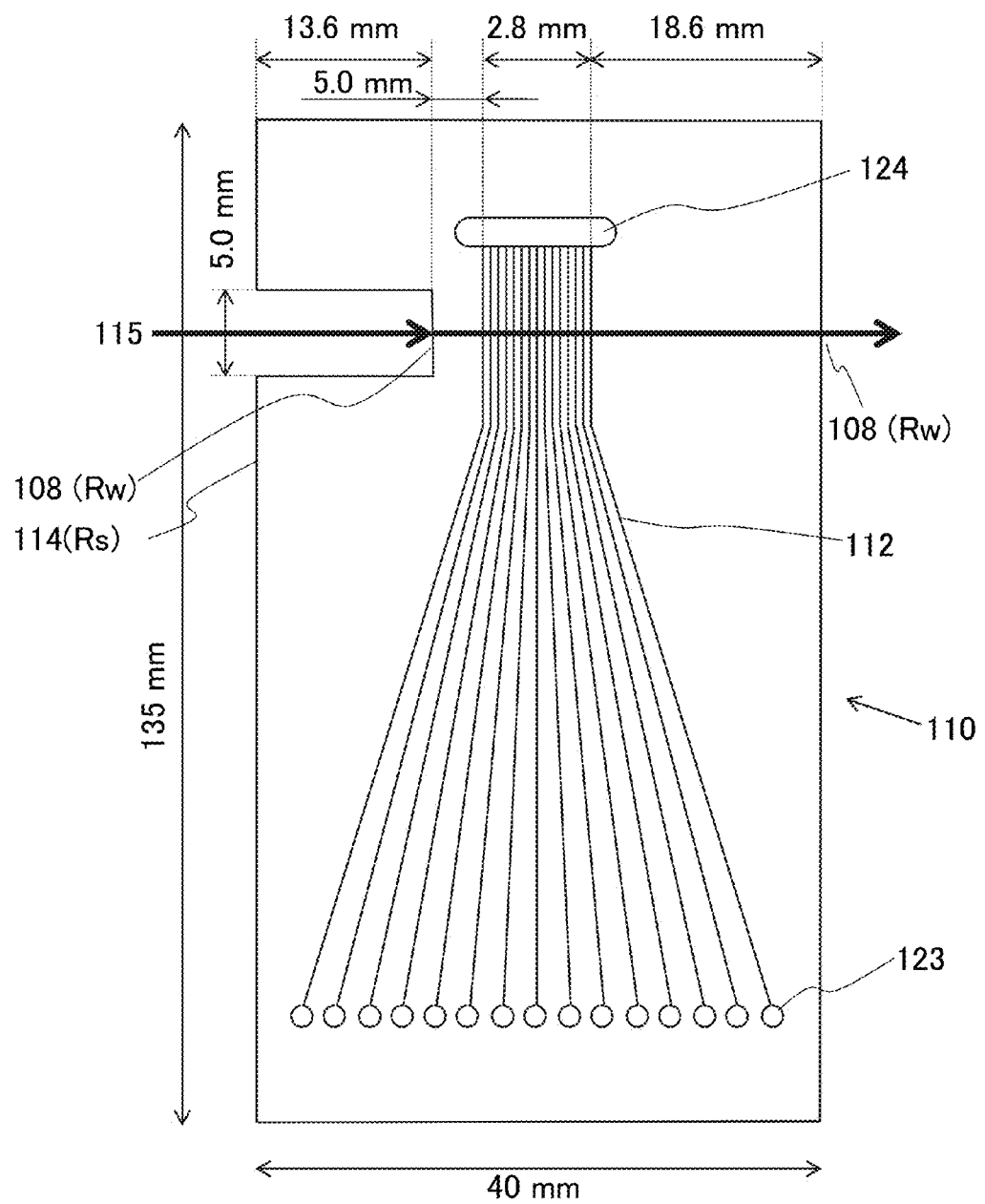
FIG. 51 is a view showing an example of a microchip having 15 channels.

On the other hand, as shown in FIG. 51, a shape of the front face of the microchip 110, in a rectangle of 40 mm×135 mm, a portion with a width of 5.0 mm and a length of 13.6 mm on which the laser beam 115 was incident was recessed. As a result, a distance between the side face 108 on which the laser beam 115 was incident on the microchip 110 and the channel 112 on which the laser beam 115 was first irradiated (the channel 112 which is arranged on the leftmost side in FIG. 51) was made to be 5.0 mm. Further, a distance between the channel 112 on which the laser beam 115 was irradiated last (the channel 112 arranged on the rightmost side in FIG. 51) and the side face 108 from which the laser beam 115 was emitted from the microchip 110 was made to be 18.6 mm.

The fabrication of such a microchip 110 was realized by the injection molding, and machining was not used. Further, the surface roughness Rw of the side face 108 was made to be smaller than the surface roughness Rs of the side face 114 of other portion by using a mold mechanism as shown in FIGS. 28(a) and 28(b). However, in FIG. 51, for simplicity, the face having the large surface roughness Rs was illustrated not by a wavy line but a straight line. Actually, when the surface roughness Rw of the side face 108 was measured, the surface roughness Rw is 0.07 μm in the RMS, and the side face 108 was brought into a smooth surface equivalent that of the front face.

Although as described above, mainly a sectional shape of the channel 112 was approximately expressed by a square or a rectangle, accurately, the sectional shape of the channel is a trapezoid. However, in FIG. 38 through FIG. 45, the sectional shape of the channel was illustrated by the trapezoid. When a description is given by using FIGS. 26(a) to 26(c), if a tapered shape is not provided to a protruded portion of the core mold 101, it is difficult to separate the core mold 101 from the recessed shape resin substrate 106. The tapered shape described above is transcribed also to the recessed portion of the recessed shape resin substrate 106 as it is. As a result, it is general that the channel 112 is configured by a trapezoid having a tapered shape of lower base<upper base. At this time, an angle subtracting 90° from a base angle of the trapezoid is referred to as draft angle, and there is frequently a case where a draft angle of at least 5° is provided. According to the present embodiment, a lower base (hereinafter, referred to as short base) of each channel was 40 μm, a height thereof was 40 μm, and draft angles on both left and right sides were 7°. At this time, the upper base (hereinafter, referred to as long base) is made to be about 50 μm.

When the laser beam is made to be incident on such a channel having a section in a trapezoidal shape in parallel with the long base and the short base, a refractive index nA of an aqueous solution for analysis filling the inner portion of the channel is smaller than a refractive index nC of a resin, and therefore, the laser beam transmits through the channel by being refracted in a direction of being directed from the long base to the short base of the channel. Therefore, when the laser beam is made to be incident on an array of plural channels having an equivalent shape in parallel with the array plane, the laser beam is deviated from the channel array by the refraction described above, and the laser beam cannot irradiate the plural channels efficiently and simultaneously. As means for resolving such a new problem, there was devised a system of configuring plural channels by alternately arranging A channels filled with the aqueous solution for analysis having the refractive index of nA (<nC) and B channels filled with a laser beam control solution having the refractive index of nB (>nC). That is, according to the system, by satisfying a relationship of nA<nC<nB, while at the A channel, the laser beam is refracted in a direction of being directed from the long base to the short base of the channel section, at the B channel, the laser beam is refracted in a direction of being directed from the short base to the long base of the channel section, thereby, the refraction of the both is canceled, the laser beam is advanced in a zigzag manner and pass through the plural channels, as a result, the plural channels are simultaneously and effectively irradiated.

Figure 52:
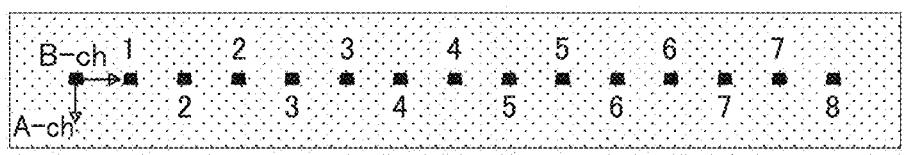
FIG. 52 shows diagrams indicating light ray trace simulation results of side-entry laser beams in a microchip having 15 channels.
Figure 52:
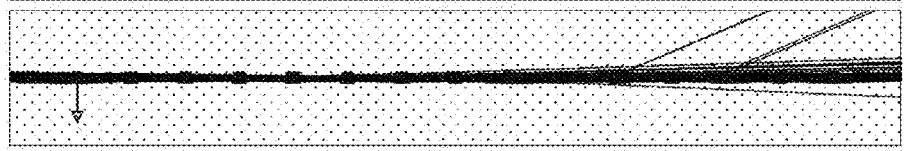
Figure 52:
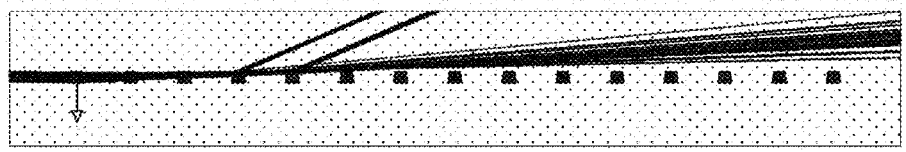

FIGS. 52(a) to 52(c) show results of confirming the effect of the system described above by light ray trace simulation. FIGS. 52(a) to 52(c) show sectional views of 15 channels and light ray trace simulation results of the laser beams at portions of irradiating the laser beams. However, here, FIGS. 52(a) to 52(c) show such that a long base of a channel section becomes a lower base, and a short base thereof becomes an upper base (by inverting an upper side and a lower side of the description described above). In FIGS. 52(a) to 52(c), the laser beams are introduced from left sides. The 15 channels are named such that A-ch1, B-ch1, A-ch2, B-ch2, . . . , A-ch7, B-ch7, A-ch8 in turn from a left side. Here, "A−" signifies A channel, and "B−" signifies B channel. That is, 8 A channels and 7 B channels were alternately arranged by configuring both sides of the channel array by A channels.

FIG. 52(a) is a diagram in which trace of a light ray of the laser beam is not displayed, and positions and shapes of respective channels can be grasped. FIG. 52(b) shows a light ray trace simulation result of the laser beam in a case of configuring nA=1.41, nC=1.53, nB=1.66 (that is, nA<nC<nB). As expected as described above, all of 15 channels were simultaneously and effectively irradiated by the laser beam introduced from the left side. This shows that the refraction in a direction of being directed from a long base (lower base) to a short base (upper base) of a channel section by the respective A channels, and the refraction in a direction of being directed from a short base (upper base) to a long base (lower base) of a channel section by B channels can be counterbalanced by each other. On the other hand, FIG. 52(c) shows a light ray trace simulation result of the laser beam in a case of configuring nA=1.41, nC=1.53, nB=1.41 (that is, nA=nB<nC). Unlike the case of FIG. 52(b), at both of A channel and B channel the refraction in a direction of being directed from a long base (lower base) to a short base (upper base) of a channel section, and therefore, the laser beam introduced from the left side was deviated to an upper side from the channel array axis, and all of the channels could not be irradiated simultaneously.

Successively, an experiment of laser beam irradiation and fluorescence detection was carried out by using a fabricated microchip. By configuring the condition of nA=1.41, nC=1.53, nB=1.66 of FIG. 52(b), a constant concentration of a fluorescent material (100 nM of dR110) was mixed only to a filling solution of A channel. First, in FIG. 51, the laser beam 115 was introduced from the side face 108 of the right side of the microchip 110 opposedly to an illustrated direction in parallel with the front face of the microchip and the channel array plane. Here, the side face 108 on the right side was previously smoothed. That is, a distance between the center axis of the laser beam 115 and the lamination surface was x=y/2=40 μm/2=0.02 mm. The laser beam 115 was configured to have a wavelength 505 nm, intensity 14.85 mW, and a diameter 50 μm. A fluorescence detection optical system and a data analyzer used were made to be equivalent to those shown in FIGS. 5(a) to 5(c). However, a fluorescence intensity detected by each channel 112 was smaller than expected. A fluorescence intensity obtained by the rightmost side channel 112 irradiated first by the laser beam 115 (A-ch8 according to the naming described above) was only about 10% of the fluorescence intensity obtained under the same condition by using one channel 112 of the microchip 110 of FIG. 33. When investigated in details, it was found as a cause thereof that the microchip 110, and the lamination surface of the flat shape resin substrate and the recessed shape resin substrate of FIG. 51 were bent, the laser beam was scattered in transmitting the lamination surface described above, and laser intensity was attenuated.

As a countermeasure thereagainst, as shown in FIG. 51, a recessed structure was provided at a position of introducing the laser beam 115 in the microchip 110, a distance between the side face 108 on which the laser beam 115 introduced from the left side was incident, and the leftmost side channel 112 (A-ch1 according to the naming described above) irradiated first by the laser beam 115 was shortened from 18.6 mm to 5.0 mm, and the side face 108 was smoothed. Also in this case, the laser beam 115 was introduced in parallel with the lamination surface, and a distance between the center axis of the laser beam 115 and the lamination surface was made to be x=y/2=40 μm/2=0.02 mm. As a result, the laser scattering at the lamination surface was restrained. However, the fluorescence intensity obtained at the A-ch1 remained to be about 50% of a fluorescence intensity obtained under the same condition by using one channel 112 of the microchip 110 of FIG. 33.

Hence, a next device was carried out in accordance with the above-described. At the side face 108 on which the laser beam 115 is incident, the distance between the center axis of the laser beam 115 and the lamination surface was enlarged from 0.02 mm to 0.09 mm. Here, a position of the laser beam center axis at the side face 108 was moved from the lamination surface to a side of the recessed shape resin substrate. Then, the laser scattering at the lamination surface described above was substantially nullified, and the fluorescence intensity obtained at A-ch1 was made to be equivalent to a fluorescence intensity obtained under the same condition by using one channel 112 of the microchip 110 of FIG. 33.

Figure 53:
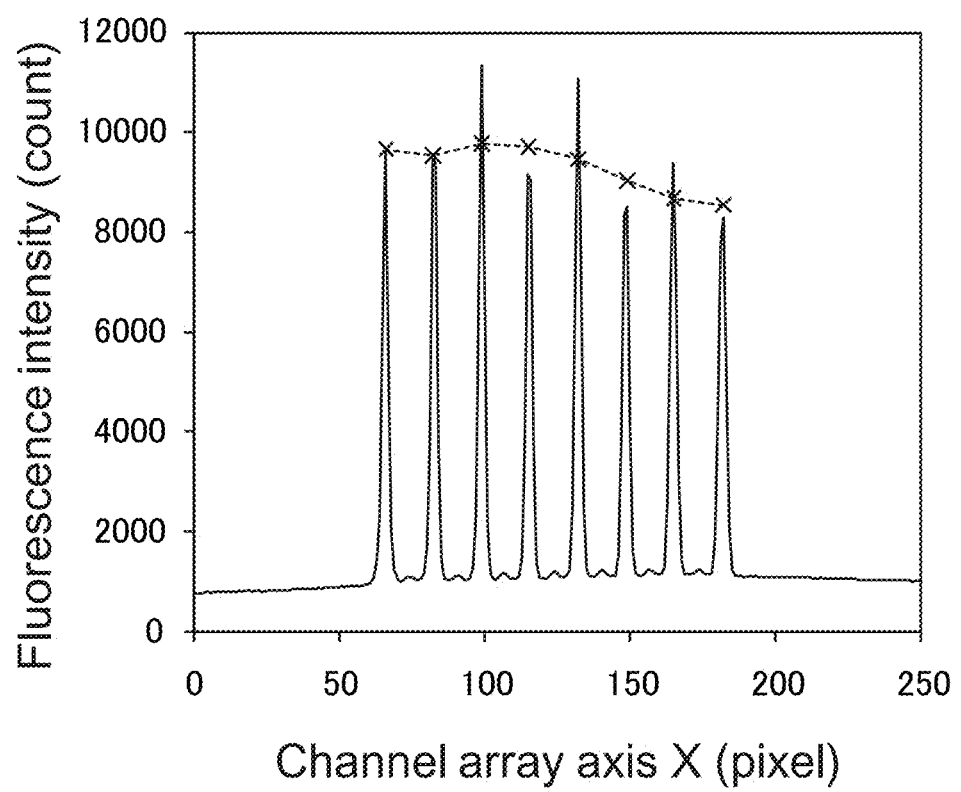
FIG. 53 is a diagram showing an experimental result of fluorescence intensity distribution along eight A channels.

FIG. 53 shows distribution of fluorescence intensities obtained by 8 A channels in the experiment under conditions described above. 8 peaks shown by solid lines indicate fluorescence intensities of 8 A channels, expressing fluorescence intensities of A-ch1, A-ch2, . . . , A-ch8 respectively from the left side. On the other hand, plots of X and a broken line show a result of calculating fluorescence intensities obtained by the respective channels based on the light ray trace result shown in FIG. 52 (b). The experimental result and the calculation result excellently agree with each other, and therefore, by satisfying a relationship of nA<nC<nB, it was verified that the refractions by A channels and B channels were counterbalanced by each other, and plural channels could simultaneously and effectively be irradiated by advancing the laser beam in a zigzag manner in the channel array. Although in FIG. 53, the fluorescence intensity is little smaller at A channels on the righter side, this is caused by reflection losses of the laser beam at respective A channels and B channels and a boundary face of the microchip. However, the attenuation is made to be able to be restrained at an extremely low level. A fluorescence intensity obtained by 8 A channels is equivalent to a fluorescence intensity obtained under the same condition by using one channel 112 of the microchip 110 of FIG. 33, and therefore, it was found that highly sensitive fluorescence detection can be carried out by 8 A channels.

In order to carry out highly sensitive fluorescence detection at the respective channels as described above, it is effective to make the surface roughness of the side face of the microchip on which the laser beam is incident lower than that of the side face of the other portion. Further, it is effective to shorten a distance between the side face of the microchip on which the laser beam is incident and the channel which is irradiated first by the laser beam. Further, it is effective to enlarge a distance between the center axis of the laser beam and the lamination surface of the microchip on the side face of the microchip on which the laser beam is incident.

According to any of the above-described embodiments, examples are configured by electrophoresis analysis using microchips, however, naturally, the present invention can also be applied to other analysis using a microchip. For example, it is possible that PCR of plural samples is carried out at different plural channels, simultaneous fluorescence detection is carried out by making a laser beam horizontally incident on these, and object DNA segments included in the plural samples can be quantitatively determined highly sensitively. Further, a microTAS or a Lab on a Chip can be configured by integrating pretreatment steps to a microchip to which the present invention is applied. For example, the present invention can be applied to a system in which after injecting a human blood sample to a microchip, blood cell separation, genome extraction or the like is carried out in the microchip, the sample is divided and introduced to plural channels, presence of plural DNA segments associated with a particular disease is quantitatively determined highly sensitively by PCR, and a gene diagnosis of the particular disease is carried out based on the results. In such an application, it is necessary that a microchip can be mass-produced at low cost and can be made to be disposable for preventing contamination among samples, thus the effect of the present invention is particularly achieved. As other examples, the present invention can be applied to various applications of an immunity analysis, a flow cytometer, a single cell analysis, a microreactor and so on carried out on a microchip.

Although in the above-described embodiments, as shown in FIGS. 5(a) to 5(c) and FIGS. 18(a) to 18(c), fluorescence emitted from each channel 2 was measured by a common fluorescence detection system, there maybe constructed independent multiple fluorescence detection systems for respective channels from a direction vertical to an array flat face or an array curved face of each channel. By constructing such a configuration, cross talk among channels can further be reduced. Further, a light reflection preventing film may be formed on an outer surface of the microchip 1 in a direction opposed to a direction of detecting fluorescence relative to an array plane or an array curve of each channel. Although it is not necessarily needed to directly bond the reflection preventing film to the outer surface of the microchip 1, for example, a member absorbing light may be arranged in contact with the outer surface of the microchip 1. By constructing such a configuration, the possibility can be reduced in which a component of fluorescence emitted from each channel advancing in a direction on a side opposed to the fluorescence detection system is reflected by the outer surface of the microchip 1 or an outside portion, the reflected light is detected by the fluorescence detection system, and cross talk is brought about thereby.

Further, the present invention is not limited to the above-described embodiments, but includes various modified examples. For example, the above-described embodiments have been explained in details for explaining the present invention to be easy to understand, and the present invention is not necessarily limited to what includes all of the configurations explained. Further, a portion of a configuration of a certain embodiment can be replaced by a configuration of other embodiment, further, a configuration of other embodiment can also be added to a configuration of a certain embodiment. Further, other configuration can be added, deleted, or replaced concerning a portion of a configuration of each embodiment.

LIST OF REFERENCE SIGNS

0: medium of surrounding of microchip, 1: microchip, 2: channel, 3: beam side-entry axis, 4: lamination surface, 5: center axis of laser beam, 6: laser beam, 7: mold of injection molding, 8: part of microchip including groove on surface, 9: part of microchip not including groove on surface, 10: inlet port of channel, 11: outlet port of channel, 12: laser light source, 13: condensing lens, 14: filter and diffraction grating, 15: imaging lens, 16: two-dimensional sensor, 17: data analyzer, 18: two-dimensional fluorescence image, 19: wavelength dispersion image of fluorescence from channel by exciting laser beam, 20: laser beam, 21: beam side-entry axis, 22: laser light source, 23: half-silvered mirror, 24: mirror, 25: wavelength dispersion image of fluorescence from channel by exciting laser beam, 26: adjusting mechanism of position and angle of mirror and stage, 27: stage of flat face shape fixing microchip, 28: beam side-entry curve, 29: stage of curved face shape fixing microchip, 30: push force in stage direction applying to microchip, 31: channel for calibration, 101: core mold, 102: cavity mold, 103: space, 106: recessed shape resin substrate, 107: front face, 108: side face (portion on which laser beam is incident and portion from which laser beam is emitted), 109: flat shape resin substrate, 110: microchip, 111: lamination surface, 112: channel, 113a: buildup, 113b: depression, 114: side face (portion on which laser beam is not incident and portion from which laser beam is not emitted), 115: laser beam, 116: laser scattering, 117: slide mold, 118: pin, 120: grinding buff, 121: adhering agent, 122: glass window, 123: inlet port, 124: outlet port, 125: transparent substance, 126: screen, 127: image taking area, $n_0$: refractive index of medium at surrounding of microchip, $n_1$: refractive index of member of microchip, $n_2$: refractive index of member at inner portion of channel and channel for calibration, $\theta_0$: angle made by laser beam approaching microchip and beam side-entry axis, $\theta_1$: angle made by laser beam approaching No. 1, channel and beam side-entry axis, $\theta_2$: angle made by laser beam approaching No. 2 and beam side-entry axis, $\epsilon_2$: refraction angle of laser beam by channel, R: radius of curvature of beam side-entry curve

The invention claimed is:

1. A multichannel analyzer comprising:
a microchip in which a plurality of channels filled with a member having a refractive index $n_2$ are arranged at an inner portion of a transparent solid member having a refractive index $n_1$ such that long axes of the respective channels are substantially in parallel with each other at at least a portion of an area;
a laser light source;
an irradiation optical system for making a laser beam generated from the light source incident from a side face of the microchip substantially vertically to the long axes of the plurality of channels arranged substantially in parallel with each other; and
a light detection optical system for respectively separating and detecting light emission from the plurality of channels by irradiating the laser beam,
wherein an angle $\theta_1$ made by the laser beam approaching the channel F which is irradiated first by the laser beam in the plurality of channels relative to a plane including the respective long axes of the channel F and the channel L which is irradiated last by the laser beam in the plurality of channels is in a relationship of $\theta_1 > 0$.

2. The multichannel analyzer according to claim 1, wherein sections vertical to the long axes of the plurality of channels are in a tapered shape,
wherein $n_1 > n_2$, and
wherein in the section of the channel F, when the laser beam is directed in a direction of widening a width of the tapered shape, a sign of the angle $\theta_1$ is made to be positive.

3. The multichannel analyzer according to claim 1,
wherein the microchip includes a first part and a second part pasted together by respective lamination surfaces,
wherein the lamination surface of the first part is provided with a plurality of grooves configuring the plurality of channels, wherein the lamination surface of the second part is not provided with the groove, and
wherein when the laser beam is directed in a direction of the second part from the first part, a sign of the angle $\theta_1$ is made to be positive.

4. The multichannel analyzer according to claim 1,
wherein the long axes of the plurality of channels are arranged on the same plane.

5. The multichannel analyzer according to claim 4,
wherein sections vertical to the long axes of the plurality of channels are configured by the trapezoidal shapes, and
wherein when $D_L$ and $D_R$ are $0°<D_L<90°$ and $0°<D_R<90°$, and averages of two base angles of a plurality of the trapezoidal shapes are $90°+D_L$ and $90°+D_R$, if $D=(D_L+D_R)/2$, $\epsilon_2=\sin^{-1}[\sin\{2D-\sin^{-1}(\sin(D)\times n_1/n_2)\}\times n_2/n_1]-D$ are established, $\theta_1+\epsilon_2>0$ is satisfied.

6. The multichannel analyzer according to claim 4,
wherein an average of an array interval of the plurality of channels is p, and sections vertical to the long axes are configured by the trapezoidal shapes, and
wherein when $D_L$ and $D_R$ are $0°<D_L<90°$, and $0°<D_R<90°$, and averages of two base angles of a plurality of the trapezoidal shapes are $90°+D_L$ and $90°+D_R$, and an average of heights of the plurality of trapezoidal shapes is d, if $D=(D_L+D_R)/2$, $\epsilon_2=\sin^{-1}[\sin\{2D-\sin^{-1}(\sin(D)\times n_1/n_2)\}\times n_2/n_1]-D$ are established, $p\times\tan(\theta_1+\epsilon_2)<d$ is satisfied.

7. The multichannel analyzer according to claim 6,
wherein when a width in a direction of the laser beam approaching the channel F in a direction vertical to the same plane is b, and
when the number of the channels irradiated by the laser beam in the plurality of channels is L, $b>p(L-1)\tan\theta_1$ is satisfied.

8. The multichannel analyzer according to claim 4,
wherein an average of array intervals of the plurality of channels is p, and sections vertical to long axes are configured by the trapezoidal shapes; and
wherein when $D_L$ and $D_R$ are $0°<D_L<90°$ and $0°<D_R<90°$, and averages of two base angles of a plurality of the trapezoidal shapes are $90°+D_L$ and $90°+D_R$, an average of heights of the plurality of trapezoidal shapes is d, if $D=(D_L+D_R)/2$, $\epsilon_2=\sin^{-1}[\sin\{2D-\sin^{-1}(\sin(D)\times n_1/n_2)\}\times n_2/n_1]-D$ $M=\text{int}(-\theta_1/\epsilon_2+1)$ are established, $p\times\tan(\theta_1+\epsilon_2)+p\times\tan(\theta_1+2 6\epsilon_2)+\ldots+p\times\{\theta_1+(M-1)\epsilon_2)\}<d$ is satisfied.

9. The multichannel analyzer according to claim 8,
wherein when a width of the laser beam approaching the channel F in a direction vertical to the same plane is b, and
when the number of the channels irradiated by the laser beam in the plurality of channels is L, $b>p(L-2M)\tan\theta_1$ is satisfied.

10. The multichannel analyzer according to claim 1,
wherein sections vertical to the long axes of the plurality of channels are configured by a tapered shape, and
wherein the long axes of the plurality of channels are arranged on a circular cylinder face having a radius of curvature R.

11. The multichannel analyzer according to claim 10,
wherein when an average of array intervals of the plurality of channels is p, and sections vertical to the long axes are configured by the trapezoidal shape, and
when $D_L$ and $D_R$ are $0°<D_L<90°$, and $0°<D_R<90°$, and averages of two base angles of the plurality of the trapezoidal shapes are $90°+D_L$ and $90°+D_R$, if $D=(D_L+D_R)/2$, and $\epsilon_2=\sin^{-1}[\sin\{2D-\sin^{-1}(\sin(D)\times n_1/n_2)\}\times n_2/n_1]-D$ are established, $p/|2\epsilon_2|<R<p/|\epsilon_2/2|$ is satisfied.

12. The multichannel analyzer according to claim 10,
wherein when an average of array intervals of the plurality of channels is p, and sections vertical to the long axes are configured by the trapezoidal shape, and
when $D_L$ and $D_R$ are $0°<D_L<90°$, and $0°<D_R<90°$, and averages of two base angles of the plurality of the trapezoidal shapes are $90°+D_L$ and $90°+D_R$, if $D=(D_L+D_R)/2$, $\epsilon_2=\sin^{-1}[\sin\{2D-\sin^{-1}(\sin(D)\times n_1/n_2)\}\times n_2/n_1]-D$ are established, $p/|1.2\epsilon_1|<R<p/|0.8\ \epsilon_2|$ is satisfied.

13. The multichannel analyzer according to claim 10,
wherein when an average of array intervals of the plurality of channels is p, and sections vertical to the long axes are configured by the trapezoidal shape, and
when $D_L$ and $D_R$ are $0°<D_L<90°$, and $0°<D_R<90°$, and averages of two base angles of a plurality of the trapezoidal shapes are $90°+D_L$ and $90°+D_R$, if $D=(D_L+D_R)/2$, $\epsilon_2=\sin^{-1}[\sin\{2D-\sin^{-1}(\sin(D)\times n_1/n_2)\}\times n_2/n_1]-D$ are established, $R=p/|\epsilon_2|$ is substantially satisfied.

14. The multichannel analyzer according to claim 10,
wherein a mechanism of changing the radius of curvature R is provided.

15. The multichannel analyzer according to claim 1,
wherein a mechanism of changing the angle $\theta_1$ is provided.

16. The multichannel analyzer according to claim 1,
wherein in the side face of the microchip, an average of a surface roughness of an area of the side face of the microchip including a position on which the laser beam is incident and a surrounding thereof is smaller than an average of a surface roughness of the remaining area.

17. The multichannel analyzer according to claim 16,
wherein in the side face of the microchip, an average of a surface roughness RMS of at least a portion of the side face of the microchip on which the laser beam is incident is equal to or smaller than 0.24 µm.

18. The multichannel analyzer according to claim 16, wherein in the side face of the microchip, at least a portion of the side face of the microchip on which the laser beam is incident is constructed by a structure recessed to an inner side than the surrounding.

19. The multichannel analyzer according to claim 16, wherein in the side face of the microchip, at least a portion of the side face of the microchip on which the laser beam is incident is constructed by a structure protruded to an outer side than the surrounding.

20. The multichannel analyzer according to claim 1, wherein in addition to a plurality of first channels in which a first member of the refractive index $n_2$ is filled in an inner portion of a transparent solid member of the refractive index $n_1$, second channels filled with second members of a refractive index $n_3$ are alternately arranged, and a relationship of $n_2 < n_1 < n_3$ is satisfied.

21. A multichannel laser beam irradiating method for making a laser beam generated from a laser light source incident from a side face of a microchip in which a plurality of channels whose sections vertical to long axes are configured by a tapered shape are aligned such that the long axes of the respective channels are substantially in parallel with each other at least a portion of an area substantially vertically to the long axes of the plurality of channels arranged in parallel with each other, the laser beam irradiating method comprising:

a step of setting an angle $\theta_1$ using one of a lens and a stage adjuster, a mirror adjuster, and the stage adjuster, said angle $\theta_1$ being made by the laser beam approaching a channel F which is irradiated first by the laser beam, from a laser light source, in the plurality of channels relative to a plane including respective long axes of the channel, F and a channel L which is irradiated last by the laser beam, from the laser light source, in the plurality of channels is in a relationship $\theta_1 > 0$, when the laser beam is directed in a direction from a side of a narrow width to a side of a wide width of the tapered shape; and a step of irradiating the laser beam from the laser light source to the plurality of channels from the side face of the microchip.

22. A microchip, wherein a plurality of channels filled with a member having a refractive index $n_2$ are aligned at an inner portion of a transparent solid member having a refractive index $n_1$ such that long axes of the respective channels are substantially in parallel with each other at at least a portion of an area,
wherein sections vertical to long axes of the plurality of channels are configured by a tapered shape, and
wherein the long axes of the plurality of channels are arranged on a circular cylinder face having a radius of curvature R.

23. A microchip, wherein a plurality of channels are arranged such that long axes of the respective channels are substantially in parallel with each other at at least a portion of an area in an inner portion of a transparent solid member, and
wherein an average of a surface roughness of at least a portion of a side face of the microchip is smaller than an average of a surface roughness of the remaining portion.

24. The microchip according to claim 23, wherein the average of the surface roughness RMS of the one portion of the side face of the microchip is equal to or smaller than 0.24 μm.

25. The microchip according to claim 23, wherein the portion of the side face of the microchip is constructed by a structure recessed to an inner side than a surrounding.

26. The microchip according to claim 23, wherein the portion of the side face of the microchip is constructed by a structure protruded to an outer side than a surrounding.

* * * * *